US008406893B2

(12) United States Patent
Krause et al.

(10) Patent No.: US 8,406,893 B2
(45) Date of Patent: Mar. 26, 2013

(54) INTERFERENCE MITIGATION FOR IMPLANTABLE DEVICE RECHARGING

(75) Inventors: Paul G. Krause, Shoreview, MN (US); William T. Donofrio, Andover, MN (US); Gerald P. Arne, Long Lake, MN (US); James D. Reinke, Maple Grove, MN (US); David J. Peichel, Minneapolis, MN (US); Timothy Davis, Coon Rapids, MN (US); John E. Burnes, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 685 days.

(21) Appl. No.: 12/610,053

(22) Filed: Oct. 30, 2009

(65) Prior Publication Data

US 2010/0114216 A1 May 6, 2010

Related U.S. Application Data

(60) Provisional application No. 61/110,131, filed on Oct. 31, 2008.

(51) Int. Cl.
*A61N 1/08* (2006.01)

(52) U.S. Cl. .......................................................... 607/61

(58) Field of Classification Search ................. 607/5, 34, 607/59, 61, 112
See application file for complete search history.

(56) References Cited

U.S. PATENT DOCUMENTS

| 4,374,382 A | 2/1983 | Markowitz |
|---|---|---|
| 4,886,064 A | 12/1989 | Strandberg |
| 4,987,897 A | 1/1991 | Funke |
| 5,113,859 A | 5/1992 | Funke |
| 5,117,824 A | 6/1992 | Keimel et al. |
| 5,261,400 A | 11/1993 | Bardy |
| 5,292,338 A | 3/1994 | Bardy |
| 5,545,186 A | 8/1996 | Olson et al. |
| 5,755,736 A | 5/1998 | Gillberg et al. |
| 5,897,575 A | 4/1999 | Wickham |
| 6,134,470 A | 10/2000 | Hartlaub |
| 6,188,926 B1 | 2/2001 | Vock |
| 7,387,610 B2 | 6/2008 | Stahmann et al. |
| 2001/0001126 A1 | 5/2001 | Cammilli et al. |
| 2003/0045906 A1 | 3/2003 | Stroebel et al. |
| 2003/0078634 A1 | 4/2003 | Schulman et al. |
| 2004/0199082 A1 | 10/2004 | Ostroff et al. |
| 2005/0149133 A1 | 7/2005 | Libbus et al. |
| 2005/0197680 A1 | 9/2005 | DelMain et al. |
| 2006/0031378 A1 | 2/2006 | Vallapureddy et al. |

(Continued)

FOREIGN PATENT DOCUMENTS

| EP | 1060762 A2 | 12/2000 |
|---|---|---|
| WO | 2009055579 A1 | 4/2009 |

OTHER PUBLICATIONS

Budgett et al. "Novel Technology for the Provision of Power to Implantable Physiological Devices", Journal of Applied Physiology, vol. 102, No. 104, Apr. 2007, pp. 1658-1663. International Search Report and Written Opinion from PCT/US2009/062833, dated Dec. 22, 2010, 17 pp.

(Continued)

*Primary Examiner* — Brian T Gedeon
(74) *Attorney, Agent, or Firm* — Carol F. Barry

(57) ABSTRACT

A therapy or monitoring system may implement one or more techniques to mitigate interference between operation of a charging device that charges a first implantable medical device (IMD) implanted in a patient and a second IMD implanted in the patient. In some examples, the techniques may include modifying an operating parameter of the charging device in response to receiving an indication that a second IMD is implanted in the patient. The techniques also may include modifying an operating parameter of the second IMD in response to detecting the presence or operation of the charging device.

50 Claims, 14 Drawing Sheets

U.S. PATENT DOCUMENTS

| | | |
|---|---|---|
| 2006/0095080 A1 | 5/2006 | Libbus et al. |
| 2006/0241699 A1 | 10/2006 | Libbus et al. |
| 2007/0150011 A1 | 6/2007 | Meyer et al. |
| 2007/0239215 A1 | 10/2007 | Bhunia et al. |
| 2007/0239229 A1 | 10/2007 | Masoud et al. |
| 2007/0260283 A1 | 11/2007 | Li |
| 2008/0015659 A1 | 1/2008 | Zhang et al. |
| 2008/0021507 A1 | 1/2008 | Libbus et al. |
| 2008/0125826 A1 | 5/2008 | Belalcazar et al. |
| 2008/0147140 A1 | 6/2008 | Ternes et al. |
| 2008/0167696 A1 | 7/2008 | Cates et al. |
| 2008/0215118 A1 | 9/2008 | Goetz et al. |
| 2009/0012416 A1 | 1/2009 | Belalcazar et al. |
| 2009/0026201 A1 | 1/2009 | Hall et al. |
| 2009/0112291 A1 * | 4/2009 | Wahlstrand et al. ............ 607/61 |

OTHER PUBLICATIONS

U.S. Appl. No. 61/110,131, filed Oct. 31, 2008 entitled "Interference Mitigation for Implantable Device Recharging", by Krause et al.

U.S. Appl. No. 61/110,117, filed Oct. 31, 2008 entitled "Interdevice Impedance", by Burnes et al.

U.S. Appl. No. 12/362,895, filed Jan. 30, 2009, entitled "Interdevice Impedance", by Burnes et al.

U.S. Appl. No. 61/110,144, filed Oct. 31, 2008, entitled "Interference Mitigation for Implantable Device Recharging", by Donofrio et al.

U.S. Appl. No. 12/610,025, filed Oct. 30, 2009, entitled "Interference Mitigation for Implantable Device Recharging", by Donofrio et al.

International Preliminary Report on Patentability from international application No. PCT/2009/062833, dated May 12, 2011, 12 pp.

* cited by examiner

INTERFERENCE MITIGATION FOR IMPLANTABLE DEVICE RECHARGING

This application claims the benefit of U.S. Provisional Application No. 61/110,141, entitled, "INTERFERENCE MITIGATION FOR IMPLANTABLE DEVICE RECHARGING," filed on Oct. 31, 2008, the entire content of which is incorporated herein by reference.

TECHNICAL FIELD

The invention relates to implantable medical devices, and more particularly, to recharging implantable medical devices.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy to or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry.

Implantable cardiac devices, such as cardiac pacemakers or implantable cardioverter-defibrillators, provide therapeutic stimulation to the heart by delivering electrical therapy signals such as pulses or shocks for pacing, cardioversion, or defibrillation via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, or deliver cardioversion or defibrillation therapy to a patient's heart upon detecting ventricular fibrillation. Some proposed medical device systems include a neurostimulator in addition to the implantable cardiac device.

SUMMARY

In general, the present disclosure is directed to mitigating interference between the operation of a charging device that charges a first therapy module implanted in a patient and a second therapy module implanted in the patient. In some examples, the first and second therapy modules are enclosed in physically separate housings, e.g., as part of respective implantable medical devices, while in other examples, the first and second therapy modules are enclosed in a common outer housing. In some examples, an operating mode of the charging device is controlled in response to receiving an indication that the second therapy module is implanted in the patient, e.g., an indication that the second therapy module is within a particular distance range of the first therapy module. In some examples described herein, an operating mode of the second therapy module can be controlled in response to detecting the presence or operation of the charging device.

In one aspect, the disclosure is directed to a system comprising a first therapy module implanted within a patient, a second therapy module implanted within the patient, a charging device that charges the first therapy module, and a processor that receives an indication of a presence of the second therapy module and modifies, based on the indication, an operating parameter of the charging device to reduce interference with operation of the second therapy module.

In another aspect, the disclosure is directed to a method comprising receiving an indication of a presence of a first therapy module implanted in a patient, and modifying, based on the indication, an operating parameter of a charging device that charges a second therapy module implanted in the patient.

In yet another aspect, the disclosure is directed to a system comprising a charging module that generates a charging signal to charge a first therapy module implanted in a patient, and a processor that receives an indication of a presence of a second therapy module in a patient and modifies an operating parameter of the charging module to reduce interference with operation of the second therapy module based on the indication.

In a further aspect, the disclosure is directed to a system comprising means for charging a first therapy module implanted within a patient, means for receiving an indication of a presence of a second therapy module implanted in the patient, and means for modifying, based on the indication, an operating parameter of the means for charging to reduce interference with operation of the therapy module.

In another aspect, the disclosure is directed to a computer readable medium comprising instructions that cause a programmable processor to receive an indication of a presence of a first therapy module implanted in a patient and, based on the indication, modify an operating parameter of a charging device that charges a second therapy module implanted in the patient.

In an additional aspect, the disclosure is directed to a system comprising a first therapy module implanted within a patient, a second therapy module implanted within the patient, and a processor that detects charging of the first therapy module by a charging device and modifies an operating parameter of the second therapy module based on the detection of the charging of the first therapy module.

In another aspect, the disclosure is directed to a method comprising detecting a charging device that is configured to charge a first therapy module implanted in a patient, and modifying an operating parameter of a second therapy module implanted in the patient based on the detection of the charging of the first therapy module.

In a yet another aspect, the disclosure is directed to a system comprising means for detecting a charging device that is configured to charge a first therapy module implanted in a patient and means for modifying an operating parameter of a second therapy module implanted in the patient based on the detection of the charging of the first therapy module.

In a further aspect, the disclosure is directed to computer readable medium comprising instructions that cause a programmable processor to detect a charging device that is configured to charge a first therapy module implanted in a patient, and modify an operating parameter of a second therapy module implanted in the patient based on the detection of the charging of the first therapy module.

In other aspects, the disclosure is directed to computer readable medium comprising instructions that cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory (RAM), or any other type of volatile or non-volatile memory that stores instructions (e.g., in the form of a computer program or other executable) to cause a programmable processor to perform any part of the techniques described herein.

The details of one or more examples are set forth in the accompanying drawings and the description below. Other features, objects, and advantages will be apparent from the description and drawings, and from the statements provided below.

DETAILED DESCRIPTION

Figure 1:
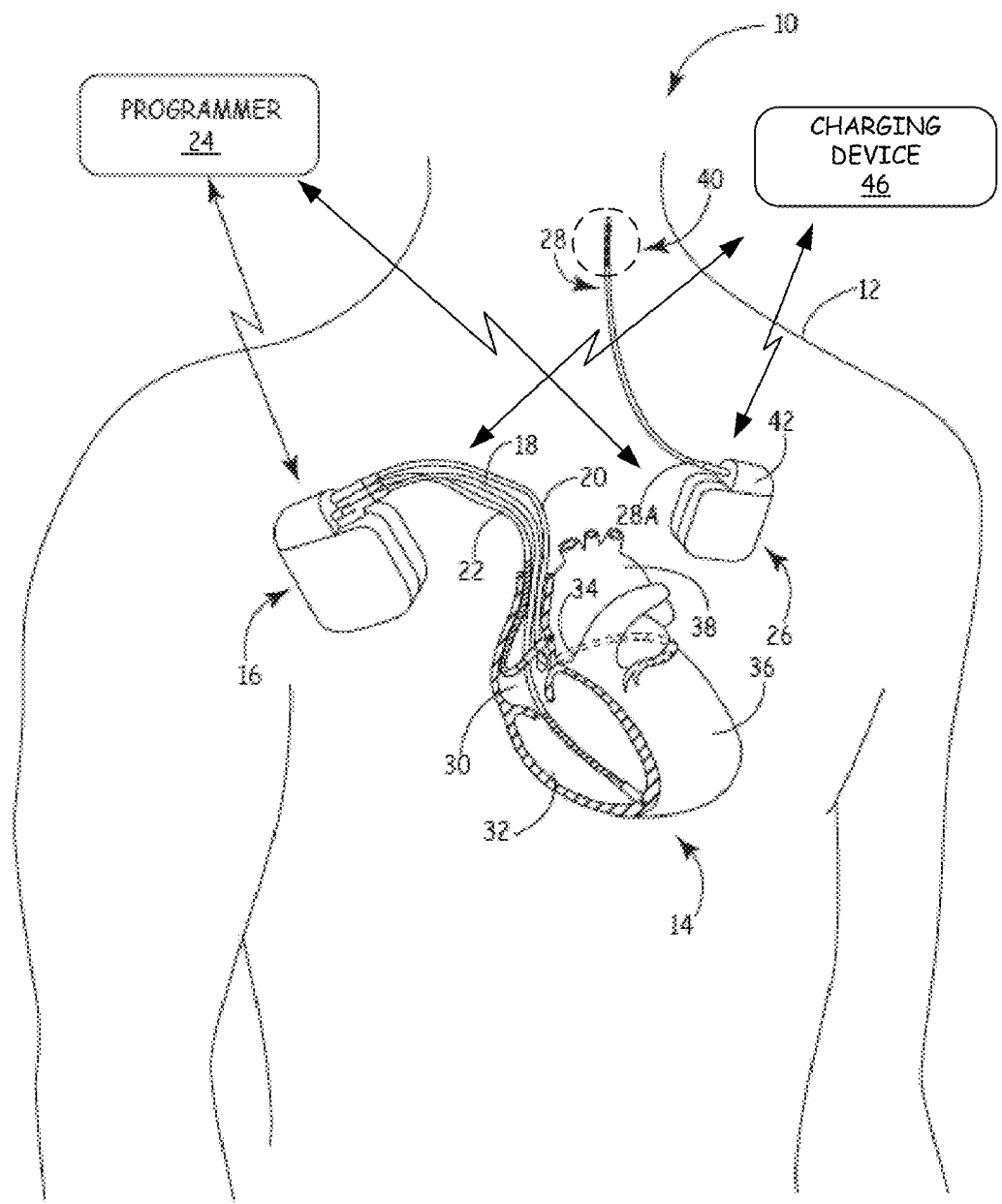
FIG. 1 is a conceptual diagram illustrating an example therapy system that includes an implantable cardiac device (ICD), an implantable neurostimulator (INS), and a charging device that recharges a power source of at least one of the ICD or the INS.

In general, the disclosure is directed to reducing interference, and more particularly in some examples, cross-talk, between a charging device for charging a power source of a first therapy module implanted in a patient and a second therapy module implanted in the patient. In some examples, the first therapy module, which is charged by the charging device, includes an electrical stimulator that generates electrical stimulation that may be delivered to a tissue site within a patient. In other examples, the second therapy module includes an electrical stimulator. In some examples, the tissue site may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or a nerve. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some cases, a first implantable medical device (IMD) includes the first therapy module and a second IMD, which is physically separate from the first IMD, includes the second therapy module. In other cases, the first and second therapy modules are enclosed within a common medical device housing, such that the first and second therapy modules are part of a common IMD. Thus, the description below relating to reducing interference between a charging device and an IMD in therapy systems including physically separate IMDs is also applicable to reducing interference between a charging device and a therapy module in therapy systems including two or more therapy modules within a common medical device housing.

Throughout the following description, the first IMD will be generally referred to as an implantable neurostimulator (INS). However, the INS may stimulate tissue sites other than or in addition to tissue sites proximate a nerve of the patient. The second IMD generally will be referred to as an implantable cardiac device (ICD) that generates and delivers cardiac rhythm therapy to a heart of the patient. The cardiac rhythm therapy may include any one or more of a pacing, cardioversion or defibrillation therapy.

In other examples, the first IMD that may be charged by the charging device may be an ICD, and the second IMD that is implanted in the patient may be an INS. Thus, the techniques described herein for reducing interference with a second IMD that may result from recharging a first IMD may be used to reduce interference with the operation of an INS that may result from recharging of an ICD. Further, in other examples, one or both of the IMDs may comprise other devices, such as, for example, an implantable monitoring device, which may monitor one or more physiological parameters of the patient, or an implantable drug delivery device.

In still other examples, a single IMD may include two or more modules, which may control different aspects of therapy provided to or monitoring of one or more physiological parameters of the patient. For example, a single IMD may include a cardiac therapy module and an electrical stimulation module, which generate cardiac rhythm management therapy for delivery to a heart and stimulation therapy for delivery to another tissue site within the patient, respectively. The techniques described herein may be used to reduce interference with an operation of a first therapy module of an IMD that may result from recharging of a second therapy module of the same IMD.

Other combinations of IMDs, modules within a single IMD, or both will be apparent to those of skill in the art, and are within the scope of the present disclosure. Accordingly, the following description of a system including an ICD and an INS will be understood to not limit the disclosure to a system including an ICD and an INS, or to a system including two IMDs.

FIG. 1 is a conceptual diagram illustrating an example therapy system 10 that may be used to provide therapy to a patient 12. Patient 12 ordinarily, but not necessarily, will be a human. Therapy system 10 includes a first IMD, ICD 16, and a second IMD, INS 26. In other examples, therapy system 10 may include a single IMD or more than two IMDs. Therapy system 10 also includes programmer 24 and charging device 46.

In the example depicted in FIG. 1, ICD 16 is connected (or "coupled") to leads 18, 20, and 22. ICD 16 may be, for example, a device that provides cardiac rhythm management therapy to heart 14, and may include, for example, an implantable pacemaker, cardioverter, and/or defibrillator that provide therapy to heart 14 of patient 12 via electrodes coupled to one or more of leads 18, 20, and 22. In some examples, ICD 16 may deliver pacing pulses, but not cardioversion or defibrillation shocks, while in other examples, ICD 16 may deliver cardioversion or defibrillation shocks, but not pacing pulses. In addition, in further examples, ICD 16 may deliver pacing pulses, cardioversion shocks, and defibrillation shocks.

Therapy system 10 further comprises INS 26, which is connected to lead 28. INS 26 may be any suitable IMD that includes a signal generator that generates electrical stimulation that may be delivered to a nonmyocardial tissue site or a nonvascular cardiac tissue site of patient 12, e.g., tissue proximate a vagus nerve, a spinal cord or heart 14 of patient 12. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some examples, delivery of electrical stimulation to a tissue site proximate a nerve or a nonmyocardial tissue site that may not be proximate a nerve may help modulate an autonomic nervous system of patient 12. In some examples, INS 26 may deliver electrical stimulation therapy to a nerve of patient 12 via a lead implanted within vasculature (e.g., a blood vessel) of patient 12. In some examples, INS 26 may deliver electrical stimulation that is delivered to peripheral nerves that innervate heart 14, or fat pads on heart 14 that may contain nerve bundles.

In the example shown in FIG. 1, electrodes of lead 28 are positioned outside the vasculature of patient 12 and positioned to deliver electrical stimulation to a vagus nerve (not shown) of patient 12. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature. For example, an intravascular lead may be implanted within a jugular vein and deliver stimulation to a vagal nerve through the vein wall. In some examples, delivery of electrical stimulation by INS 26 may complement antitachycardia therapy (e.g., antitachycardia pacing, cardioversion or defibrillation) by ICD 16 or provide back-up therapy to the cardiac rhythm management therapy provided by ICD 16.

While the following disclosure is primarily directed to examples that include an ICD 16 and an INS 26, the techniques described herein may be applied to systems including one or more other IMDs. For example, one or more of the IMDs may comprise an implantable drug delivery device, which may include a rechargeable battery that powers a drug delivery pump. As another example, one or more of the IMDs may include an implantable monitoring device, which may include a rechargeable battery. The implantable monitoring device may sense one or more of a variety of physiologic parameters or other parameters related to a condition of patient 12, including, for example, electrical cardiac signals, blood pressure or other hemodynamic parameters, neurologic parameters, pH of blood or other bodily fluids, activity, posture, heart sounds, or the like.

In the example illustrated in FIG. 1, ICD 16 and INS 26 are not physically connected to each other and each includes a respective outer housing. Moreover, in the example shown in FIG. 1, ICD 16 is not mechanically connected to the electrodes of lead 28 and INS 26 is not mechanically connected to the electrodes of leads 18, 20, 22. However, in other examples, such as the example depicted in FIG. 7 (described below), a single IMD 130 may include cardiac therapy module 134 and electrical stimulation module 136, both housed in a common housing 132. The cardiac therapy module 134 can generate and deliver cardiac rhythm management therapy to heart 14 and electrical stimulation module 136 can generate and deliver electrical stimulation therapy to a nonmyocardial tissue site or a nonvascular cardiac tissue site.

As shown in FIG. 1, leads 18, 20, 22 that are coupled to ICD 16 can be implanted such that leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle (LV) 36 of heart 14. Right atrial (RA) lead 22 extends through one or more veins and the vena cava, and into the right atrium 30 of heart 14. In other examples, ICD 16 may deliver stimulation therapy to heart 14 by delivering stimulation to an extravascular tissue site in addition to or instead of delivering stimulation via electrodes of intravascular leads 18, 20, 22.

ICD 16 may sense electrical signals attendant to the depolarization and repolarization of heart 14 (e.g., cardiac signals) via electrodes (not shown in FIG. 1) coupled to at least one of the leads 18, 20, 22. In some examples, ICD 16 provides pacing pulses to heart 14 based on the cardiac signals sensed within heart 14. The configurations of electrodes used by ICD 16 for sensing and pacing may be unipolar or bipolar. ICD 16 may sense cardiac signals and provide therapy in one or more chamber of heart 14. In some examples, ICD 16 may be configured to allow switching between a single-chamber pacing and monitoring mode and a multiple-chamber pacing and monitoring mode. ICD 16 may also provide defibrillation therapy and/or cardioversion therapy via electrodes located on at least one of the leads 18, 20, 22. ICD 16 may detect arrhythmia of heart 14, such as fibrillation of ventricles 32 and 36, and deliver defibrillation therapy to heart 14 in the form of electrical shocks. In some examples, ICD 16 may be programmed to deliver a progression of therapies, e.g., shocks with increasing energy levels, until a fibrillation of heart 14 is stopped. ICD 16 may detect fibrillation by employing one or more fibrillation detection techniques known in the art. For example, ICD 16 may identify cardiac parameters of the cardiac signal, e.g., R-waves, and detect fibrillation based on the identified cardiac parameters.

In the example of FIG. 1, INS 26 has been implanted in patient 12 proximate to a target stimulation site 40, such as a tissue site proximate a vagus nerve (not shown). For example, INS 26 may be implanted subcutaneously or submuscularly in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. In some examples, lead 28 may also carry one or more sense electrodes to permit INS 26 to sense electrical signals from target stimulation site 40. Furthermore, in some examples, INS 26 may be coupled to two or more leads, e.g., for bilateral or multi-lateral stimulation.

Proximal end 28A of lead 28 may be both electrically and mechanically coupled to connector 42 (also referred to as a header or connector block) of INS 26 either directly or indirectly (e.g., via a lead extension). In particular, conductors disposed in the lead body may electrically connect stimulation electrodes (and sense electrodes, if present) of lead 28 to INS 26. In the example shown in FIG. 1, INS 26 provides electrical stimulation therapy of a parasympathetic nerve, such as a vagus nerve, of patient 12. Delivery of electrical stimulation by INS 26 may complement antitachycardia therapy (e.g., antitachycardia pacing, cardioversion or defibrillation) by ICD 16 or provide back-up therapy to the cardiac rhythm therapy provided by ICD 16. For example, if ICD 16 is unavailable to provide therapy to patient 12, e.g., due to a low power level, INS 26 may deliver therapy to patient 12 to help terminate or prevent a cardiac event (e.g., tachycardia).

In other examples, electrodes of lead 28 may be positioned to deliver electrical stimulation to any other suitable nerve, organ, muscle or muscle group in patient 12, which may be selected based on, for example, a therapy program or regimen selected or prescribed for a particular patient. In some examples, INS 26 may deliver electrical stimulation to other sympathetic or parasympathetic nerves, baroreceptors, or the carotid sinus or a cardiac branch of the vagal trunk of patient 12 in order to complement the delivery of therapy by ICD 16.

Figure 2:
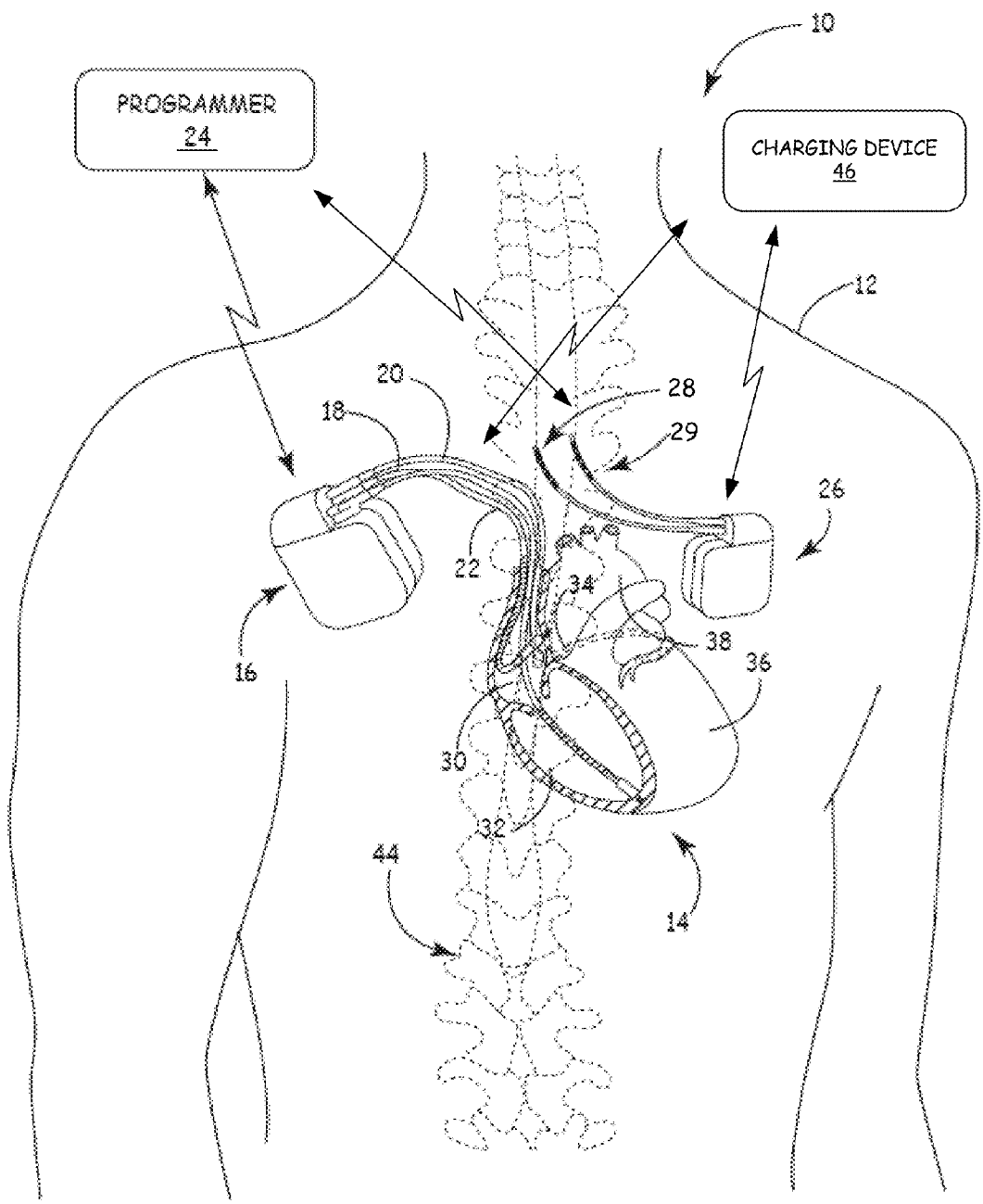
FIG. 2 is a conceptual diagram illustrating another example therapy system that includes an ICD and an INS.

As another example, as shown in FIG. 2, INS 26 can deliver electrical stimulation to spinal cord 44 of patient 12. In the example shown in FIG. 2, INS 26 is coupled to two leads 28, 29, which may facilitate bilateral spinal cord stimulation of patient 12. In other examples, INS 26 may be coupled to a single lead 28, 29 or more than two leads. Although leads 28, 29 are shown as introduced into spinal cord 44 via the thoracic column in the example shown in FIG. 2, in other examples, leads 28, 29 may be introduced into spinal cord 44 near the lumbar region or other regions of spinal cord 44. Electrodes of leads 28, 29 may be positioned within an intrathecal space or epidural space of spinal cord 44, or, in some examples, adjacent nerves that branch off spinal cord 44. Stimulation of spinal cord 44 or nerves branching therefrom by INS 26 may help prevent or mitigate occurrences of tachyarrhythmias and may reduce the level of aggressiveness of the cardiac therapy, such as pacing, cardioversion or defibrillation, delivered by ICD 16. In this way, ICD 16 and INS 26 may operate in conjunction with each other to help prevent arrhythmias of heart 14 of patient 12, as well as to terminate detected arrhythmias. In addition, stimulation of spinal cord 44 may help manage symptoms of heart failure.

Stimulation of spinal cord 44 or nerves branching therefrom by INS 26 may help prevent or mitigate occurrences of tachyarrhythmias and may facilitate reduction of the level of aggressiveness of the cardiac therapy, such as pacing, cardioversion or defibrillation therapy, delivered by ICD 16. In this way, ICD 16 and INS 26 may operate in conjunction with each other to help prevent arrhythmias of heart 14 of patient 12, as well as to terminate detected arrhythmias.

In some examples, programmer 24 may be a handheld computing device or a computer workstation. Programmer 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as "electrogram" or EGM), intracardiac or intravascular pressure, activity, posture, respiration, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by ICD 16, such as cardioversion or pacing therapies. For example, with the aid of programmer 24, a user may select therapy parameter values for ICD 16. The therapy parameters may include an electrode combination, a current or voltage amplitude, a pulse width, and a pulse rate for stimulation signals to be delivered to heart 14 of patient 12. An electrode combination may include a selected subset of one or more electrodes located on implantable leads 18, 20, 22 that are coupled to ICD 16. The electrode combination may also refer to the polarities of the electrodes in the selected subset. By selecting values for amplitude, pulse width, and pulse rate, the physician can attempt to generate an efficacious therapy for patient 12 that is delivered via the selected electrode subset. In some examples, the user may activate certain features of ICD 16 by entering a single command via programmer 24, such as depression of a single key or combination of keys of a keypad or a single point-and-select action with a pointing device.

The user may also use programmer 24 to retrieve information from INS 26 regarding the performance or integrity of INS 26 or leads 28, 29 (if INS 26 is connected to more than one lead) or a power source of INS 26. In addition, the user may use programmer 24 to program INS 26. For example, with the aid of programmer 24 or another computing device, a user may select values for therapy parameters for controlling therapy delivery by INS 26. The values for the therapy parameters may be organized into a group of parameter values referred to as a "therapy program" or "therapy parameter set." "Therapy program" and "therapy parameter set" are used interchangeably herein.

In the case of electrical stimulation, the therapy parameters for INS 26 may include an electrode combination, a frequency, a voltage or current amplitude, a duty cycle, phase, slew rate, and, if INS 26 delivers electrical pulses, a pulse width or a pulse rate for stimulation signals to be delivered to patient 12. An electrode combination may include a selected subset of one or more electrodes located on implantable lead 28 coupled to INS 26, and, in some cases, the polarities of the selected electrodes. The electrode combination and electrode polarity may be said to define an electrode vector. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset.

In some examples, a user may utilize programmer 24 to retrieve and view or analyze signals sensed by at least one of ICD 16 and INS 26. The signals sensed by the at least one of ICD 16 and INS 26 may show differences when charging device 46 is generating a charging signal and when charging device 46 is not generating a charging signal. The user may compare the sensed signal from exemplary time periods to observe the effects of the charging signal on signals sensed by the at least one of ICD 16 and INS 26.

Programmer 24 may communicate with ICD 16 and INS 26 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

At least one of ICD 16 and INS 26 may comprise a rechargeable power source, such as, for example, a rechargeable battery or a supercapacitor. Charging device 46 is configured to inductively charge the rechargeable power source of at least one of ICD 16 and INS 26. For example, charging device 46 may utilize inductive coupling to transfer energy inductively from a coil coupled to charging device 46 to a coil coupled to ICD 16 or INS 26. In some examples, charging device 46 may be a handheld device. While charging device 46 may be utilized to charge a power source of ICD 16, INS 26, or both, charging device 46 will be described in the following examples as charging a power source of INS 26. However, it will be understood that the disclosure is not thus limited, and that charging device 46 may be used to charge a power source of ICD 16 or another IMD, in addition to or instead of charging a power source of INS 26.

In some examples, charging device 46 includes a user interface that is configured to receive input from a user. The user interface may include, for example, a keypad and a display, which may be, for example, a CRT display, a LCD or LED display. The keypad may take the form of an alphanumeric keypad or a reduced set of keys associated with particular functions. Charging device 46 can additionally or alternatively include a peripheral pointing device, such as a stylus or mouse, via which a user may interact with the user interface. In some embodiments, a display of charging device 46 may include a touch screen display, and a user may interact with charging device 46 via the display.

A user, such as patient 12, a physician, technician, or other clinician, may interact with charging device 46 to charge a rechargeable power source of INS 26 (and, optionally, ICD 16). For example, the user may interact with the user interface of charging device 46 to initiate charging of INS 26 by device 46, modify (or control) an operating parameter of one or more of charging device 46, ICD 16, and INS 26, or terminate charging of INS 26 by charging device 46. For example, the user may modify an operating parameter of charging device 46 by modifying one or more charging parameters, which may include, for example, a duty cycle, slew rate, phase, frequency bandwidth, frequency value, current or voltage amplitude, burst duration or burst rate of a charging signal, or a charging duration.

In some examples, a charging module of charging device 46 may generate a charging signal that comprises a substantially continuous waveform (e.g., a sinusoidal waveform), a discontinuous waveform (e.g., pulses or square waves), or hybrid waveforms (e.g., rounded square waves, sinusoidal waveforms interrupted by discontinuities, or the like). Regardless of whether the charging module generates a charging signal as a continuous, discontinuous, or hybrid waveform, in some examples, the charging signal may be generated in a plurality of bursts separated by intervals of time, during which the charging module does not generate a charging signal, as described in further detail below.

Charging device 46 communicates with at least one of ICD 16 and INS 26 via wireless communication using any technique known in the art. In some examples, charging device 46 communicates with ICD 16 via INS 26. For example, charging device 46 may transmit a communication signal to INS 26, which may then transmit the communication signal to ICD 16. In this way, INS 26 may be a communication link between ICD 16 and charging device 46. In other examples, charging device 46 may communicate directly with ICD 16 via wireless communication. In some examples, ICD 16 provides a communication link between INS 26 and charging device 46, while in other examples, charging device 46 may communicate directly with INS 26 via wireless communication.

Examples of communication techniques that can be implemented to support communication between charging device 46 and ICD 16 and/or INS 26 may include, for example, low frequency or RF telemetry, but other techniques are also contemplated. For example, charging device 46 may communicate with at least one of ICD 16 and INS 26 by encoding information in a charging signal generated by charging device 46. As described in further detail below, the information may be encoded by specifically varying a frequency or amplitude of the charging signal, and ICD 16 or INS 26 may detect and decode the information encoded in the charging signal. In some examples, charging device 46 may generate a single signal that comprises a power sufficient to charge INS 26, where the charge signal is modulated to encode information for communication with at least one of INS 26 and ICD 16. In other examples, charging device 46 may generate a first signal that comprises a power sufficient to charge INS 26 and a second signal that includes encoded information for communication with at least one of ICD 16 and INS 26. In these examples, the second signal may comprise a lower power than the first signal. In addition, the first and second signals may comprise different frequencies or modulations (e.g., frequency or amplitude modulation), and may be transmitted substantially simultaneously or at different times.

In some examples, charging device 46 includes a programming head that may be placed proximate to the patient's body near the ICD 16 and or INS 26 implant sites in order to improve the quality or security of communication between ICD 16 or INS 26, respectively, and programmer 24.

Charging device 46 communicates information to ICD 16 and/or INS 26 that indicates, for example, that charging device 46 is currently charging INS 26 and/or ICD 16 or about to initiate generation and/or delivery of charging signals. Upon receiving the indication that charging device 46 is ready to or already generating and delivering charging signals or an indication of prospective delivery of charging signals, ICD 16 and/or INS 26 may modify operation in order to reduce the possibility of sensing noise generated by the charging signals. ICD 16 and/or INS 26 may modify operation by, for example, changing a sensing parameter with which the device senses physiological signals, by suspending therapy delivery, or by generating a notification to charging device 46.

Charging device 46 may communicate instructions to ICD 16 and/or INS 26, or may receive operating instructions from ICD 16 and/or INS 26. For example, charging device 46 can communicate instructions to ICD 16 and/or INS 26 to cause the ICD 16 or INS 26 to modify an operating parameter. As described in further detail below, in some examples, an operating parameter of ICD 16 is modified by modifying a sensing parameter with which ICD 16 senses cardiac signals. As examples, a blanking period during which ICD 16 does not sense electrical cardiac signals of patient 12 or deliver cardiac rhythm therapy, a sensing threshold with which ICD 16 identifies cardiac signals, a sensing threshold with which ICD 16 identifies cardiac parameters (e.g., R-waves or P-waves) of the cardiac signal, or a type of filter that ICD 16 applies to sensed electrical signals may be modified to help reduce the effect of the crosstalk from charging device 46. Alternatively or additionally, charging device 46 may receive an indication that ICD 16 is present, e.g., implanted in patient 12, when charging INS 26, or vice versa.

In some examples, prior to initiating charging of INS 26, charging device 46 may receive an indication from ICD 16 or INS 26 that charging device 46 may proceed with the delivery of charging signals to charge INS 26. ICD 16 and/or INS 26 may provide the indication to charging device 46 after an initial, relatively low power charging signal or communication signal is delivered by charging device 46 to INS 26, which may allow INS 26 or ICD 16 to determine whether operation of charging device 46 interferes with operation of ICD 16. The delivery of an initial indication that charging device 46 may proceed with the delivery of charging signals to charge INS 26 can also enable ICD 16, INS 26, and/or programmer 24 to determine whether INS 26 is compatible with charging device 46, e.g., whether charging device 46 is configured to charge the specific type of INS 26 implanted within patient 12. In other examples, ICD 16 and/or INS 26 may provide the indication to charging device 46 upon detecting the presence of charging device 46, such as after ICD 16 or INS 26 receives a communication signal from charging device 46 requesting an indication from ICD 16 or INS 26 that charging device may initiate charging of INS 26. Each of these instructions is described in further detail below.

Charging device 46 may also include a charging antenna, which may comprise the same antenna that is used to wirelessly communicate with ICD 16, programmer 24, and/or INS 26, or may comprise a separate antenna. The charging antenna may be enclosed in a housing of device 46, or may comprise an external antenna electrically and mechanically coupled to charging device 46. For example, the charging antenna may be enclosed in the programming head or a separate charging head that allows a user to position the antenna proximate to a location of the IMD to be charged (e.g., INS 26), which may increase charging efficiency of charging device 46. A charging voltage, such as an alternating current (AC) voltage, may be applied to the charging antenna, producing an alternating magnetic field. The alternating magnetic field may induce a voltage in a conductor placed in the magnetic field. In this way, charging device 46 may charge a rechargeable power source of an IMD (e.g., ICD 16 or INS 26) that includes an antenna, such as a loop antenna or coiled antenna, when the charging antenna of device 46 is positioned such that the antenna of the IMD is in the magnetic field produced by charging device 46. In other examples, pulses of a direct current (DC) voltage may be applied to the charging antenna, and the change from substantially no voltage to the DC voltage may generate the changing magnetic field that induces a voltage in a conductor placed in the magnetic field.

Although the magnetic field produced by charging device 46 enables charging of a rechargeable power source of INS 26, the magnetic field may also cause interference with operation of other devices implanted in patient 12, such as ICD 16. For example, when charging device 46 is used to charge a power source of INS 26, the magnetic field produced by charging device 46 may induce a voltage in a conductor of one or more of leads 18, 20, 22. The induced voltage may cause electrical noise in a signal conducted by leads 18, 20, 22, such as a cardiac signal.

Electrical noise in the signal conducted by leads 18, 20, 22 may result in one or more issues. For example, electrical noise may affect the ability of ICD 16 to properly detect an electrical signal. As one example, electrical noise may reduce the accuracy of measurements of impedance of an electrical path that includes leads 18, 20, 22. ICD 16 may periodically check the impedance of one or more electrical paths, each path comprising two or more implanted electrodes on one or more implanted leads. The impedance measurements may be used to detect lead-related conditions, such as short circuits, open circuits or significant changes in impedance that may affect the performance of therapy delivery by ICD 16 or INS 26 or sensing by ICD 16 or INS 26. In some examples, lead integrity testing may also involve comparing the measured impedance to a threshold impedance value in order to determine whether the lead(s) have a lead-related condition, such as mechanical issues in the lead (e.g., a break or fracture of one or more conductors). ICD 16 may also measure impedance of an electrical path including one or more of leads 18, 20, 22 to determine an impedance of tissue. Impedance of tissue may be used to determine, for example, distance between leads to detect lead migration, changes in tissue edema, respiration, or the like. In any case, electrical noise as a result of an induced voltage may result in diminished performance when ICD 16 is performing an impedance measurement.

In some examples, ICD 16 may sense the electrical noise generated by delivery of a charging signal by charging device 46 and interpret the electrical noise as cardiac signals (e.g., an electrocardiogram (ECG) or EGM signal, and also referred to as an electrical cardiac signal). This may cause ICD 16 to incorrectly identify cardiac parameters from the cardiac signals, such as a heart rhythm of patient 12. In some cases, electrical noise may cause ICD 16 to erroneously detect an arrhythmia. For example, a processor of ICD 16 may identify electrical noise as a cardiac parameter, such as an R-wave, and detect the presence of an arrhythmia episode or event (e.g., a fibrillation episode or tachyarrhythmia episode or event) based on the electrical noise. An arrhythmia event is characterized by a cardiac cycle that has a duration less than a threshold value (also referred to as an arrhythmia event detection interval), e.g., as measured by successive R-waves or P-waves. An arrhythmia episode may include more than one arrhythmia event. Depending on the frequency of the electrical noise, the electrical noise may present itself as a relatively fast rhythm that the processor mischaracterizes as one or more tachyarrhythmia events, which the processor of ICD 16 then may use to detect a tachyarrhythmia episode. ICD 16 may detect the presence of a tachyarrhythmia episode by determining whether a certain number of intervals between successive R-waves of a particular number of total intervals have a certain duration, e.g., whether a certain number of intervals are considered tachyarrhythmia events.

Incorrect sensing of the cardiac parameters may result in inappropriate withholding or delivery of electrical stimulation to heart 14. For example, incorrect sensing may cause ICD 16 to detect a tachycardia or fibrillation episode when heart 14 is in a normal sinus rhythm, which may result in the inappropriate delivery of a high voltage defibrillation shock.

In some examples, magnetic flux generated by charging device 46 when charging INS 26 may cause saturation of a high-voltage transformer in ICD 16, which may also impact operation of ICD 16. The magnetic flux may also couple into a non-rechargeable battery of ICD 16 via a telemetry coil of ICD 16 or an accelerometer in ICD 16, if present. In some examples, this may adversely affect the performance of the non-rechargeable battery, or may adversely affect operation of the accelerometer.

Therapy system 10 implements one or more techniques to mitigate interference between charging of INS 26 by charging device 46 and operation of ICD 16. In some examples, the techniques implemented by therapy system 10 also may mitigate changes to ICD 16, such as changes that affect the performance of a non-rechargeable battery or an accelerometer. That is, therapy system 10 implement one or more techniques to reduce electrical noise detected by ICD 16 or to reduce the effect of the electrical noise on the operation of ICD 16 (e.g., the sensing of cardiac signals), where the noise is attributable to charging of INS 26 by charging device 46. The techniques may include modifying an operating parameter of one or both of ICD 16 and charging device 46.

In some examples, a processor controls the operation of charging device 46 based on whether the presence of ICD 16 is detected. While the processor may be a processor of charging device 46 or another device, such as programmer 24, ICD 16, or INS 26, a processor of charging device 46 is primarily referred to herein as controlling the operation of charging device 46 for ease of description. A processor of another device may control the operation of charging device 46 using any of the techniques described herein with respect to a processor of charging device 46. The presence of ICD 16 may be detected by charging device 46 using any suitable technique, such as based on sensing by charging device 46 or based on an indication provided by ICD 16, INS 26, programmer 24 or another device. In examples described herein, the processor of charging device 46 selects an operating mode defining one or more operating parameters of charging device 46 in response to receiving an indication of the presence of ICD 16 implanted in patient 12.

In some examples, the processor of charging device 46 automatically modifies an operating parameter of device 46, while in other examples, the processor provides an indication to a user that indicates that ICD 16 is also implanted within patient 12 or that the modification to an operating parameter of charging device 46 is recommended. The user then may respond as desired, such as, for example, by modifying a charging parameter of charging device 46, inputting, via charging device 46 or programmer 24, a command that instructs the ICD 16 to control or modify a specific charging parameter, or the like. Examples of charging parameters of charging device 46 may include, for examples, values of one or more charging signal parameters, such as a slew rate, a current or voltage amplitude, a duty cycle, phase, pulse width, frequency or pulse rate, burst pattern or burst duration. In some examples, modification of an operating parameter of charging device 46 may include ceasing generation and/or transmission of a charging signal.

Alternatively or additionally, a processor of charging device 46, programmer 24, or ICD 16 may automatically modify (e.g., control) an operating parameter of ICD 16 to mitigate interference between operation of ICD 16 and charging of INS 26 by charging device 46. Modifying an operating parameter of ICD 16 may include, for example, modifying one or more sensing parameters to help mitigate the effect of noise that is sensed by ICD 16, where the noise is attributable to the delivery of charging signals by charging device 46. Modification to an operating parameter of charging device 46 and/or ICD 16 may improve efficiency of charging INS 26 by charging device 46 or may reduce interference between ICD 16 and charging device 46 due to charging of INS 26 by charging device 46.

In some examples, the processor of charging device 46 controls a charging module of charging module 46 to generate a charging signal characterized by a predetermined signature. The processor may control the values of one or more signal parameters, e.g., a slew rate, frequency, current or voltage amplitude, duty cycle, phase, pulse width, or pulse rate, to generate the charging signal with the signature. In some examples, the predetermined charging signal signature may be characterized by a signal envelope that traces the outline of the charging signal for a given period of time.

ICD 16 may be configured to process a sensed electrical signal (e.g., cardiac signal) to substantially remove or ignore a signal artifact attributable to the signature charging signal produced by charging device 46 based on the predetermined signature of the charging signal. For example, ICD 16 may include one or more filters designed to attenuate or substantially remove the signal artifact from the sensed signal, or may apply mathematical manipulations (e.g., digital signal processing) to a digitized representation of the sensed signal to attenuate or substantially remove the signal artifact from the sensed signal. ICD 16 may analyze the processed signal, i.e., the signal after the artifact is attenuated or substantially removed, to monitor cardiac events and deliver cardiac rhythm management therapy.

As an additional example, the processor of charging device 46 may control the amplitude of the charging signal so that the charging signal does not induce a voltage in conductors of leads 18, 20, 22 that has an amplitude above a threshold value. The threshold value may comprise an amplitude above which ICD 16 identifies a sensed electrical signal as a cardiac signal, which may be referred to as a "sensing threshold," or a threshold value with which ICD 16 identifies a cardiac parameter (e.g., an R-wave or a P-wave) from a sensed cardiac signal. The threshold value may also comprise another amplitude value, such as an amplitude determined to represent a noise level that interferes with operation of ICD 16. The threshold value may be predetermined, programmed into a memory of ICD 16, charging device 46 or another device, or may be determined dynamically based one or more factors, such as operation of ICD 16. In some examples, a processor of ICD 16 may modify the threshold value in response to receiving an instruction from charging device 46, or in response to detecting charging of INS 26 by charging device 46 (e.g., detecting noise in a sensed electrical signal). By limiting the amplitude of the induced voltage, ICD 16 may not identify or interpret the induced voltage as a cardiac parameter, or noise from the induced voltage may not significantly interfere with identification of cardiac parameters from the cardiac signal.

In some examples, the processor of charging device 46 may control the amplitude of the charging signal so that the charging signal includes an initial high amplitude charging pulse followed by a series of lower amplitude charging pulses. The sensing threshold of ICD 16 may be automatically adjusting in some examples, and is adjusted based on the initial high amplitude charging pulse. The subsequent lower amplitude charging pulses may then induce a voltage that falls below adjusted sensing threshold, and are not detected by the processor of ICD 16 as a cardiac signal. In some examples, the automatically adjusting sensing threshold automatically increases in response to the initial high amplitude charging signal and subsequently exponentially decreases back towards the previous sensing threshold. In some examples, then, the charging signal generated and delivered by charging device 46 may include an initial high amplitude charging pulse followed by a series of charging pulses that have sequentially decreasing amplitudes that decrease at a faster rate than the sensing threshold decreases. This may result in a larger number of relatively higher amplitude charging pulses (which may result in a more efficient charging of the power supply of INS 26), while still delivering charging pulses that are below the sensing threshold (except the initial high amplitude charging pulse).

In other examples, a processor of charging device 46 may control an amplitude of a charging signal to initially be an amplitude used in a previous charging session. For example, a memory in charging device 46 may store charging parameters, including a charging signal amplitude used in at least one previous charging session. The initial amplitude may be, for example, an amplitude value of a charging signal that is known to not interfere with the operation of an IMD (e.g., ICD 16) implanted in patient 12 in addition to the target IMD (e.g., INS 26) to be charged. As another example, the initial amplitude of the charging signal may merely be a starting amplitude value with which charging device 46 may generate a charging signal. The previous charging session may be a previous charging session of INS 26 or another device.

The processor of charging device 46 may initiate charging of INS 26 at the stored initial amplitude value, and may or may not adjust the charging amplitude after initiation of charging. For example, the processor of charging device 46 may adjust the amplitude of the charging signal from the initial amplitude in response to an indication received from INS 26, ICD 16, or a user. In some examples, the processor of charging device 46 may adjust the amplitude of the charging signal from the initial amplitude value after initiation of the charging of INS 26. For example, the processor of charging device 46 may adjust the amplitude of the charging signal from the initial amplitude in response to an indication received from INS 26, ICD 16, programmer 24 or a user.

In some examples, a processor of charging device 46 may control an amplitude of a charging signal to initially be a moderate amplitude, e.g., an amplitude that is sufficiently high to charge INS 26 but not a maximum possible amplitude. The moderate amplitude may, in some cases, have been predetermined to be likely not to interfere with operation of ICD 16. In some examples, the processor of charging device 46 may adjust the amplitude of the charging signal from the initial, moderate amplitude after initiation of the charging of INS 26. For example, the processor of charging device 46 may adjust the amplitude of the charging signal from the initial amplitude in response to an indication received from INS 26, ICD 16, programmer 24 or a user.

The processor of charging device 46 also may control an amplitude of a charging signal in response to a indication received from a processor of INS 26. For example, the processor of charging device 46 may initiate charging of INS 26 by generating a charging signal with an initial amplitude, which may be relatively low, intermediate, or relatively high. The processor of INS 26 may monitor the amplitude of the charging signal received by a charging antenna of INS 26, and may determine whether the amplitude of the received charging signal is too low, within an acceptable range, or larger than necessary. The processor of INS 26 then may transmit an instruction to the processor of charging device 46 that causes the processor of charging device 46 to adjust the amplitude of the charging signal generated by charging device 46 such that the amplitude of the charging signal received by INS 26 falls within the acceptable range. In some examples, this process may iterate until the charging signal received by INS 26 falls within the acceptable range. Such a process may result in charging device 46 generating a charging signal that is sufficient to charge INS 26, but not excessive. In this way, ICD 16 or charging device 46 may not need to initiate additional interference mitigation techniques, or the extent of any additional interference mitigation techniques may be reduced.

In some examples, the processor of charging device 46 controls a frequency value or frequency bandwidth of the charging signal in addition to or instead of an amplitude of the charging signal to reduce interference with the operation of ICD 16. The frequency value may refer to a minimum frequency of the charging waveform, a maximum frequency of the charging waveform, an average frequency of the charging waveform, a predominant frequency of the waveform, or another measure of the frequency or frequency band that forms the charging frequency.

In some examples, the processor of charging device 46 controls the frequency value of the charging waveform to be greater than or equal to a threshold frequency. In some cases, the threshold frequency is a maximum frequency that ICD 16 identifies as representing a cardiac signal, e.g., a maximum frequency that is sensed by a sensing module of ICD 16. For example, the processor may control the frequency value of the charging waveform to comprise a value of about 100 hertz (Hz) to about 100 megahertz (MHz), although other frequency values are contemplated. The sensing module or processor of ICD 16 may identify an electrical signal comprising a frequency greater than or equal to the threshold as a non-physiologic signal. In other examples, ICD 16 may apply a bandpass filter to sense electrical cardiac signals and electrical signals having a frequency greater than or equal to the threshold may be outside of the detection zone of ICD 16, and, therefore, ignored by ICD 16. The bandpass filter is configured to exclude the charging signal generated by charging device 46.

In other examples, the processor of charging device 46 may control the frequency value of the charging waveform to be less than or equal to a threshold frequency. In some examples, the threshold frequency includes a minimum signal frequency that ICD 16 identifies as representing a fibrillation or tachyarrhythmia, e.g., less than approximately 2.5 Hz. For example, if the processor of ICD 16 detects a tachyarrhythmia event if an interval of time between R-waves is less than or equal to an arrhythmia event detection interval, charging device 46 may generate and deliver a charging signal having a frequency greater than or equal to the arrhythmia event detection interval. This may help minimize the possibility that ICD 16 mischaracterizes the charging signal as an electrical cardiac signal indicating the presence of a tachyarrhythmia event.

In other examples, the processor of charging device 46 may generate a charging signal that has a narrow frequency bandwidth centered at a predetermined frequency, which can be selected to be greater than or less than a cardiac parameter frequency that ICD 16 detects as representing tachycardia or fibrillation. In some examples, the predetermined frequency is selected as a frequency that does not generally interfere with identification of a cardiac parameter (e.g., R-wave or P-wave) from the cardiac signal. Accordingly, ICD 16 may be configured to process the detected electrical signal to substantially remove the signal artifact from the sensed signal, for example, by applying a narrowband band stop filter centered at the predetermined frequency to the sensed cardiac signal.

In some examples, the processor of charging device 46 may generate a charging signal that comprises a frequency which induces a voltage that, when aliased by an analog to digital converter (ADC) circuit that samples signals at a lower frequency than the frequency of the induced voltage, falls in a frequency range that is already substantially filtered by digital filtering performed by a processor of ICD 16. That is, the processor of charging device 46 may control a charging module of charging device 46 to generate a charging signal that comprises a higher frequency than the sampling frequency of the ADC circuit. Thus, when the induced voltage sensed by ICD 16 is sampled by the ADC circuit, a waveform having a different morphology, and, thus, a different frequency, may be formed. This resulting waveform may fall within a range that is filtered by digital filtering techniques employed by the processor of ICD 16 or by a physical filter in ICD 16.

In other examples, the processor of charging device 46 may control a frequency bandwidth of the charging signal to comprise a relatively wide bandwidth or a wideband (e.g., spread spectrum) energy distribution. For example, the processor may control a charging module of charging device 46 to randomly or pseudo-randomly vary one or more signal parameters, e.g., a slew rate, pulse rate (frequency), pulse width (rate), phase, or duty cycle. When the processor generates signal parameters for a charging signal, the processor may vary the one or more parameters for each burst, i.e., on a burst-by-burst basis, or for each pulses, i.e., on a pulse-by-pulse basis. The spread spectrum energy distribution of the charging signal may cause the signal artifact coupled to ICD 16 to appear as wideband noise in the sensed signal, as described in further detail below with reference to FIGS. 10A and 10B. In some examples, rather than generating a true spread spectrum energy distribution, the processor may control the frequency of the charging signal to generate a charging signal with an energy spectrum spread over a relatively wideband of frequencies, e.g., about 100 Hz to about 100 MHz.

The spread spectrum energy distribution or wide band energy distribution of the charging signal may cause ICD 16 to detect the voltage induced by the charging signal as wideband noise, rather than interpreting the voltage as representing a cardiac parameter. In some examples, ICD 16 may employ signal processing techniques known in the art to substantially remove or attenuate wideband noise. Alternatively, the resulting wideband noise may be such that ICD 16 may employ well known signal processing techniques for monitoring cardiac activity. In other words, ICD 16 may not need to be configured to include additional processing features for removing the resulting wideband noise because the wideband noise may not interfere with the ability of ICD 16 to properly sense true cardiac signals.

As another example, the processor of charging device 46 may control charging of INS 26 to occur in bursts. For example, the processor may cause the charging signal to be generated as a plurality of bursts separated by gaps in which a charging signal is not generated. The processor may control charging device 46 to generate the bursts of recharge energy for an initial charging period, such as, for example, until charging device 46 communicates with INS 26 and determines that INS 26 is the correct device to be charged by charging device 46. In other examples, the processor of charging device 46 may control charging device 46 to generate the charging signal in bursts until the processor determines whether another IMD, e.g., ICD 16, is implanted in patient 12, and whether the charging signal is interfering with operation of ICD 16.

ICD 16 may identify an arrhythmia event as a cardiac cycle having a duration less than a threshold duration (also referred to as an arrhythmia event detection interval), and an arrhythmia episode as a threshold number of arrhythmia events within a particular time frame or a threshold number of consecutive arrhythmia events. In some examples, the processor may control a charging module of charging device 46 to generate the charging signal in a plurality of bursts, where the number of consecutive bursts is less than a threshold number of arrhythmia events with which ICD 16 identifies an arrhythmia episode. The plurality of bursts may comprise a plurality of sets of bursts that are separated by a predetermined duration of time. The predetermined duration of time may be selected such that ICD 16 does not identify the bursts of consecutive sets as being part of a common arrhythmia episode. For example, the sets of bursts may be separated by a duration of time longer than the threshold of time used by ICD 16 to identify an arrhythmia event (e.g., based on an R-R or P-P interval).

As another example, the processor may control a charging module of charging device 46 to generate the charging signal to have a burst duration that is less than a threshold duration over which ICD 16 identifies an arrhythmia episode or event. ICD 16 may deliver therapy to patient 12 upon detecting the arrhythmia episode. Thus, if charging device 46 delivers a charging signal comprising bursts that ICD 16 characterizes as arrhythmia events, charging device 46 may limit the number of bursts to help prevent the detection of an arrhythmia episode based on the charging signal.

For example, ICD 16 may identify a train of more than three cardiac cycles with a rate above a particular threshold (e.g., about 100 beats per minute) as a non-sustained ventricular tachycardia (NSVT) event. As another example, ICD 16 may identify an arrhythmia event as a sensed cardiac signal comprising an R-R interval below a threshold interval, and four or more arrhythmia events may constitute an arrhythmia episode that triggers some action, such as delivery of cardiac rhythm management therapy of heart 14. Thus, if the charging signal comprises sets of three or fewer bursts or a duration less than the total duration of a cardiac event, ICD 16 may not identify the voltage induced by the charging signal as a cardiac event, even if ICD 16 detects the induced voltage. In other examples, the threshold number of bursts may be different, such as greater than three, or less than three. Moreover, the number of arrhythmia events that define an arrhythmia episode are merely provided as examples and any suitable number of events may define an arrhythmia episode.

In some examples, in combination with the processor of charging device 46 controlling the charging module to generate a charging signal in a plurality of bursts, the processor of charging device 46 may directly or indirectly (e.g., via INS 26 or programmer 24) communicate an instruction to a processor of ICD 16 to increase the threshold number of events with which the processor of ICD 16 identifies an arrhythmia episode that triggers some response (e.g., the delivery of a defibrillation shock or other stimulation). For example, in response to receiving a signal from charging device 46, the processor of ICD 16 may temporarily increase an arrhythmia episode detection threshold from three arrhythmia events to five arrhythmia events for a period of time, which has a predetermined duration in some examples. The processor of ICD 16 may occasionally or periodically reduce the threshold to the original threshold (e.g., three events) to increase the sensitivity with which ICD 16 detects an arrhythmia episode and confirm that an arrhythmia episode is not occurring.

In some examples, the processor may communicate with ICD 16, and may receive an indication from ICD 16 that noise induced by the charging signal, for example, is not detected, is below a threshold level, comprises a frequency band that is substantially attenuated or removed by a filter (e.g., the charging signal can have a frequency that is substantially attenuated or removed by a filter), or otherwise does not substantially interfere with operation of ICD 16. The indication may be in the form of an electrical signal. The processor of charging device 46 then may control the operation of charging device 46 by controlling charging device 46 to cease generating and/or delivering the charging signal in bursts and begin generating a substantially continuous charging signal or otherwise change charging modes.

Conversely, if the processor of charging device 46 receives an indication that the charging signal is substantially interfering with operation of ICD 16 and ICD 16 cannot mitigate the interference, the processor may, for example, control the operation of charging device 46 by controlling charging device 46 to cease generation and/or delivery of the charging signal and alert a user interacting with charging device 46. The alert may comprise, for example, a visual alert (e.g., a warning light or alphanumeric message), an auditory alert (e.g., a beep, buzz, or other sound), a tactile alert (e.g., a vibration or another suitable somatosensory alert). The alert may be provided by charging device 46, may be provided by ICD 16, may be provided by programmer 24, or may be provided by INS 26. In other examples, the processor of charging device 46 may control one or more parameters of the charging signal to mitigate interference between the charging signal and operation of ICD 16 upon receiving a notification that the charging signal is substantially interfering with operation of ICD 16, as described above.

The processor of charging device 46 may, in some examples, communicate with at least one of INS 26 and ICD 16 prior to initiating the generation and/or delivery of the charging signal to request an indication that charging of INS 26 may begin. For example, the processor of charging device 46 may interrogate ICD 16, INS 26, and/or programmer 24 to request an indication (e.g., an electrical signal) of whether an IMD (e.g., ICD 16) other than the target IMD to be charged is present in patient 12, whether INS 26 is compatible with charging device 46, whether ICD 16 is able to utilize at least one of the interference mitigation techniques described herein, or the like. Upon being interrogated by charging device 46, the processor of ICD 16, programmer 24 or INS 26 may generate and transmit a response to charging device 46, which may indicate that charging device 46 may or may not initiate charging of INS 26. Charging device 46 may then interpret the indication received from the processor of INS 26 or ICD 16 and initiate generation of a charging signal, if appropriate, or may generate an alert to a user. The alert may indicate that charging may be initiated or that charging is not recommended, as indicated by the communication from the processor of INS 26 or ICD 16. In other examples, the indication provided by ICD 16, programmer 24 or INS 26 may indicate at least one operating parameter of INS 26 or ICD 16, and charging device 46 may adjust one or more operating parameters based on the indicated operating parameter of ICD 16 or INS 26.

In other examples, the processor of ICD 16, upon detecting a charging signal delivered by charging device 46, may generate and transmit an indication to the processor of charging device 46 that indicates ICD 16 is present within patient 12. In some examples, the processor of charging device 46 may generate a more conservative (e.g., lower amplitude) charging signal so as to mitigate any potential interference with the operation with ICD 16. In some examples, INS 26 may store in memory an indication that ICD 16 is implanted in patient 12, and upon detecting the presence of charging device 46, may generate and transmit an indication to the processor of charging device 46 that ICD 16 is present.

In other examples, the processor of charging device 46 may control the timing of the delivery of charging signals to INS 26 such that charging signals are only delivered during a blanking period of ICD 16. A blanking period refers to a period of time in which ICD 16 is not sensing cardiac signals or is not responsive to sensed cardiac signals (e.g., does not deliver stimulation to patient 12 based on the sensed cardiac signals). In some examples, the blanking period of ICD 16 may be about 100 milliseconds (ms) to about 240 ms, such as about 120 ms.

In some examples, as described above, the processor may control charging device 46 to generate a charging signal that comprises a plurality of charging pulses arranged in bursts. In some examples, charging device may generate the bursts such that the timing of the bursts corresponds in time to the blanking periods of ICD 16. As described in further detail below, in some examples, parameters regarding the blanking period of ICD 16, such as the blanking period duration and rate with which ICD 16 implements the blanking period, may be stored in memory of charging device 46. In other examples, the processor of charging device 46 may communicate with a processor of ICD 16, INS 26 or programmer 24 to retrieve parameters of the blanking period, and may control charging device 46 to generate a charging signal with a corresponding charging signal burst pattern.

In some examples, ICD 16 may be configured to provide either single-chamber pacing and sensing or multiple-chamber pacing and sensing. When providing multiple-chamber pacing and sensing, the blanking period for at least one of the chambers may be different that the blanking period for at least a different one of the chambers. In examples such as this, the processor of charging device 46 may control charging so that charging of INS 26 occurs only during at least one of the chamber's blanking period. Additionally, in some examples, the charging signal may interfere with sensing of only some of the chambers in a multiple-chamber pacing and sensing device. ICD 16 may then switch to a single-chamber pacing and sensing mode using a chamber with which the charging signal does not interfere while charging device 46 is delivering the charging signal.

In some examples, a processor of charging device 46 may control a charging module to generate a charging signal including a maximum amplitude that increases (or "ramps up") near the beginning of the charging signal, decreases (or "ramps down") near the end of the charging signal, or both. In some examples, it may be that an abrupt change from no charging signal to a maximum amplitude charging signal, e.g., an abrupt turn on of the charging signal, may introduce transient voltages which affect operation of ICD 16. By increasing the amplitude of charging signal to its maximum amplitude over a period of time, the transient voltages may not be introduced, or may comprise a lower frequency that can be filtered by a high pass filter of a sensing module of ICD 16.

In some examples, a processor may control ICD 16 to interrupt, suspend, or otherwise modify monitoring (e.g., sensing) of cardiac signals or delivery of therapy to patient 12 upon detecting charging of INS 26 by charging device 46. While the processor may be a processor of ICD 16 or another device, such as programmer 24, ICD 16, or charging device 46, a processor of ICD 16 is primarily referred to herein as controlling the operation of ICD 16 for ease of description. In other examples, a processor of another device can control the operation of ICD 16 using any of the techniques described herein with respect to a processor of ICD 16. As one example of how an operation of ICD 16 may controlled to help mitigate interference from the delivery of charging signals by charging device 46, the processor of ICD 16 may modify a duration of a blanking period, such as increasing the blanking period so that charging device 46 may generate a charging signal with a longer burst length, while still limiting the length of the burst to fall within the blanking period. In some examples, the processor of ICD 16 may increase the length of the blanking period such that the blanking period lasts multiple heart cycles. In other words, the processor of ICD 16 may periodically cycle monitoring of cardiac signals on and off.

In some examples, a processor of ICD 16 may increase the blanking period from a baseline blanking period of about 100 ms to about 150 ms to a temporary blanking period of about 151 ms to about 500 ms, such as about 300 ms, while charging device 46 delivers a charging signal. As previously indicated, in some examples, the processor of charging device 46 may control charging device 46 to deliver a charging signal to INS 26 only during times in which ICD 16 is not monitoring cardiac signals, e.g., during the blanking periods of the sensing module of ICD 16. The processor of charging device 46 may periodically suspend charging (e.g., every five to fifteen cardiac cycles, such as every ten cardiac cycles) such that processor of ICD 16 may periodically decrease the length of the blanking period or the sensing "off" cycle to check for presence of an arrhythmia. If an arrhythmia is not detected, the processor of charging device 46 may resume delivering charging signals. On the other hand, if an arrhythmia is detected, the delivery of charging signals by charging device 46 may remain suspended and ICD 16 may deliver the appropriate stimulation therapy to terminate the arrhythmia (e.g., a defibrillation shock).

As described briefly above, ICD 16 may be configured to provide either single-chamber pacing and sensing or multiple-chamber pacing and sensing. In some examples in which ICD 16 is configured to provide multiple-chamber pacing and sensing, ICD 16 may independently adjust a blanking period for each of the chambers.

In some examples, a processor of ICD 16 may temporarily switch ICD 16 from a multiple-chamber pacing and sensing mode to a single-chamber pacing and sensing mode when the processor determines that the charging signal is interfering with sensing within some, but not all, chambers of heart 14. The processor of ICD 16 may then return ICD 16 to a multiple-chamber pacing and sensing mode periodically to determine whether the charging signal is still interfering with sensing within other chambers of heart 14. Once the processor determines that the charging signal is no longer interfering with sensing within the other chambers, the processor may return ICD 16 to a multiple-chamber pacing and sensing mode.

In some examples, a processor of ICD 16 may increase the threshold number of arrhythmia events with which the processor of ICD 16 detects and identifies an arrhythmia episode that triggers some response (e.g., delivery of a defibrillation shock). The number of events with which the processor of ICD 16 identifies an arrhythmia episode may also be referred to as a number of intervals to detect. In accordance with this technique, the processor of ICD 16 may increase the threshold from three arrhythmia events to five arrhythmia events for a period of time, which can be predetermined and stored by ICD 16. The processor of ICD 16 may occasionally or periodically reduce the threshold to the original threshold (e.g., three events) to confirm that an arrhythmia episode is not occurring.

A processor of ICD 16 may also adjust an arrhythmia event detection interval with which the processor detects an arrhythmia. In some examples, the processor of ICD 16 detects an arrhythmia event if the interval between R-waves or P-waves of subsequent cardiac signals is less than or equal to the arrhythmia detection interval. In this way, the arrhythmia event detection interval can define an upper frequency limit of an EGM signal indicating an arrhythmia event. The processor of ICD 16 may temporarily decrease the detection interval while charging device 46 charges INS 26. Decreasing the detection interval enables ICD 16 to be more discerning of arrhythmia events and may help prevent the charging signal from interfering with the arrhythmia event detection by ICD 16. ICD 16 may periodically increase the detection interval limit to the original value to determine if any potential arrhythmia events detected with the longer arrhythmia event interval are being missed. For example, the processor of ICD 16 may decrease the detection interval cutoff from about 400 ms to about 300 ms temporarily, and then periodically return the detection rate cutoff to 400 ms.

A processor of ICD 16 may also adjust a sensing amplitude (voltage or current) above which the processor senses an electrical signal or interprets an electrical signal as a cardiac signal. In some examples, the processor of ICD 16 may adjust the sensing amplitude in response to an instruction received from programmer 24, INS 26 or charging device 46. In other examples, the processor of ICD 16 may monitor changes in sensed signals and determine whether adjustments of a sensing threshold is indicated based on a change in the sensed signal (e.g., an increased noise value in the sensed signal). The processor of ICD 16 then may or may not adjust the sensing threshold. In some examples, the processor of ICD 16 may also determine the magnitude of threshold adjustment indicated by the change in the sensed signal and adjust the sensing threshold accordingly.

In some examples, a processor of ICD 16 may enable a rate stability criterion. A rate stability criterion requires R-R intervals to be relatively consistent (e.g., stable) before interpreting the R-R interval as an arrhythmia. This may help avoid detecting irregularly conducted atrial fibrillation. In many examples, noise appears as an irregular signal in a sensed cardiac signal, so a rate stability criterion may mitigate the effect of noise on detection of heart arrhythmias.

In some examples, a processor of ICD 16 may utilize a wavelet criterion to mitigate the effect of noise on detection of heart arrhythmias. A wavelet criterion requires the morphology of a cardiac signal detected by EGM to change before interpreting cardiac signal parameters as representing a true arrhythmia. Because noise may appear as an irregular signal in the sensed cardiac signal, implementation of a wavelet criterion to detect an arrhythmia may also be used mitigate the effect of noise on detection of a true heart arrhythmia.

For example, noise due to charging of INS 26 by charging device 46 may cause the wavelet criterion to return an incorrect result (e.g., the wavelet criterion may indicate a change in the morphology of the cardiac signal, when the change is caused by noise, not a change to the underlying cardiac signal). To determine whether the result of the wavelet criterion is due to the charging signal, the processor of ICD 16 may first determine a wavelet template by fitting a wavelet function to a sensed cardiac signal when charging device 46 is not delivering the charging signal. For example, the processor may determine at least one coefficient or exponent in a polynomial, rational function, exponential function, or the like to produce a wavelet function that fits at least a portion of the sensed cardiac signal when charging device 46 is not delivering the charging signal. Alternatively, the processor of ICD may determine a wavelet template that comprises an array including a plurality of time domain amplitude values and associated time values that substantially fit at least a portion of the sensed cardiac signal when charging device 46 is not delivering the charging signal. The processor of ICD 16 may store the wavelet function or wavelet criterion in a memory of ICD 16 as a wavelet function template or wavelet criterion threshold.

The processor of ICD 16 then may generate and transmit an instruction to a processor of charging device 46 that causes the charging module of charging device 46 to initiate the delivery of charging signals to INS 26. The processor of ICD 16 may apply the wavelet template to a sensed cardiac signal when charging device 46 is delivering the charging signal to INS 26 to determine a wavelet score indicative of a similarity between wavelet template and the sensed cardiac signal when charging device 46 is delivering a charging signal to INS 26. For example, the processor of ICD 16 may cross-correlate the wavelet function template and the sensed cardiac signal to determine the similarity (e.g., percentage of correlation) between the wavelet function template and the sensed cardiac signal.

When the wavelet score indicates that the wavelet template and the sensed cardiac signal are sufficiently similar (e.g., the wavelet score based on cross-correlation between the wavelet template and the sensed cardiac signal is greater than a predetermined threshold value), the processor of ICD 16 may determine that the generation of the charging signal by charging device 46 is not substantially interfering with operation of ICD 16. However, when the wavelet score indicates that the wavelet template and the sensed cardiac signal are not sufficiently similar (e.g., the wavelet score based on cross-correlation between the wavelet template and the sensed cardiac signal is less than a predetermined threshold value), the processor of ICD 16 may determine that the generation of the charging signal by charging device 46 is interfering with operation of ICD 16, and may cause a processor of charging device 46 to cease charging of INS 26, modify at least one charging parameter, or the like. This process may iterate until the wavelet score indicates that the wavelet template and the sensed cardiac signal are substantially similar (e.g., the wavelet score based on cross-correlation is greater than a threshold value) or until the processor of ICD 16 generates and transmits an instruction to a processor of charging device 46 that causes the charging device 46 to cease charging of INS 26.

In some examples, a processor of ICD 16 may enable a P-R logic criterion. A P-R logic criterion utilizes pattern analysis of atrial (e.g., P-waves of an EGM) and ventricular events (e.g., R-waves of an EGM) to analyze whether a detected fast cardiac rhythm (e.g., based on an EGM) is due to a ventricular tachycardia or ventricular fibrillation rhythm, or whether the fast rhythm is being driven by a supra-ventricular tachycardia (e.g., a sinus tachycardia, atrial fibrillation, atrial flutter, or the like). In some examples, noise caused by operation of charging device 46 may be sensed by ICD 16 via an atrial electrode, and may thus appear on an EGM to be additional atrial events. A P-R logic criterion may also be used to mitigate the effect of noise on detection of a true heart arrhythmia in addition to or in combination with the previously discussed techniques for mitigating the effects of noise on the detection of a true cardiac arrhythmia by ICD 16.

For example, noise due to charging of INS 26 by charging device 46 may cause the P-R logic criterion to return an incorrect result (e.g., the P-R logic criterion may indicate a tachycardia or fibrillation event that is not actually occurring). To determine whether the result of the P-R logic criterion is due to the charging signal, a processor of ICD 16 may first apply a P-R logic criterion to a sensed cardiac signal when charging device 46 is not delivering a charging signal to INS 26 to determine a first P-R logic result. A P-R logic result may include, for example, a determination that a ventricular tachycardia or ventricular fibrillation rhythm has occurred, or whether a supra-ventricular tachycardia rhythm (e.g., a sinus tachycardia, atrial fibrillation, atrial flutter, or the like) has occurred. In some examples, the P-R logic result may simply determine whether a rhythm is caused by a ventricular tachycardia, a ventricular fibrillation or a supra-ventricular tachycardia. In other examples, if a supra-ventricular tachycardia has occurred, the P-R logic result may determine what type of supra-ventricular tachycardia has occurred.

The processor of ICD 16 may then generate and transmit an instruction to a processor of charging device 46 that causes a charging module of charging device 46 to initiate the delivery of charging signals to INS 26. The processor of ICD 16 may apply the PR Logic criterion to a sensed cardiac signal when charging device 46 is delivering the charging signal to INS 26 to determine a second P-R logic result. The processor of ICD 16 may then compare the first P-R logic result to the second P-R logic result. When the first P-R logic result is different than the second P-R logic result, the processor of ICD 16 may generate and transmit an instruction to a processor of charging device 46 that causes the charging device 46 to cease charging of INS 26, modify at least one charging parameter used to generate the charging signal, or the like.

In examples in which the processor of ICD 16 transmits an instruction to the processor of charging device 46 to modify at least one charging parameter, the processor of ICD 16 may again apply the P-R logic criterion to a sensed cardiac signal when charging device 46 is not delivering the charging signal to determine a first P-R logic result, e.g., after charging device 46 modifies the at least one charging parameter. The processor of ICD 16 may also apply the P-R logic criterion to a sensed cardiac signal when charging device 46 is delivering the modified charging signal to INS 26 to determine a second P-R logic result, and may compare the first and second P-R logic results to determine if the first and second P-R logic results are substantially similar or different. When the first and second P-R logic results are substantially similar, the processor of ICD 16 may determine that the generation of the charging signal by charging device 46 is not substantially interfering with operation of ICD 16. However, when the first and second P-R logic results are different, the processor of ICD 16 may determine that the generation of the charging signal by charging device 46 is interfering with operation of ICD 16, and may cause the processor of charging device 46 to cease charging of INS 26, modify at least one charging parameter, or the like. This process may iterate until the first and second P-R logic results are substantially similar or until the processor of ICD 16 generates and transmits an instruction to a processor of charging device 46 that causes the charging device 46 to cease charging of INS 26.

As another example, the processor of ICD 16 may apply a P-R logic criterion that is designed to help distinguish noise induced by charging of INS 26 by charging device 46 from true a ventricular tachycardia rhythm or a true ventricular fibrillation rhythm. For example, the processor of ICD 16 may utilize at least one of an atrial-ventricular (AV) interval pattern, a ventricular-atrial (VA) interval pattern, an expected range of a ventricular-ventricular interval, an expected range of an AV interval, atrial fibrillation evidence, evidence of potential far-field R-wave sensing, atrial-ventricular dissociation, or ventricular-ventricular regularity to determine whether a sensed cardiac signal includes events that are caused by noise rather than true atrial or ventricular events.

In some examples, the processor of ICD 16 may analyze AV and VA interval patterns of a sensed cardiac signal by categorizing the atrial rhythm according to a number of apparent atrial events in a ventricular-ventricular interval. Additionally, the processor may determine zones within the ventricular-ventricular interval during which the apparent atrial events occur. As described above, noise induced by charging of INS 26 by charging device 46 may appear on an EGM to be an atrial event. By analyzing the number of apparent atrial events and the zones during which the apparent atrial events occur, the processor of ICD 16 may determine that at least one of the apparent atrial events is likely noise induced by charging of INS 26 by charging device 46. For example, the processor, with the aid of the P-R logic criterion, may determine that the detected number of atrial events and zones during which the detected atrial events occur do not correspond to the expected number of atrial events or zones for true atrial activity. The expected number of atrial events or zones for true atrial activity may be stored by ICD 16, programmer 24, or another device. On this basis, the processor may conclude that the sensed cardiac signal includes events that are caused by noise rather than true atrial events.

In some examples, the processor of ICD 16 may analyze a range of atrial-ventricular intervals by first calculating a mean atrial-ventricular interval from a number of previous atrial-ventricular interval values. The processor may construct an expected atrial-ventricular interval range utilizing mean atrial-ventricular interval and absolute differences between the recent atrial-ventricular intervals and the atrial-ventricular interval range. Subsequent atrial-ventricular intervals that fall outside the expected atrial-ventricular interval range may be excluded from further analysis. In this way, cardiac signals including noise that manifests as apparent atrial events may be excluded by the processor from analysis, because the atrial-ventricular interval may fall outside the expected atrial-ventricular interval range. At least some of the atrial-ventricular intervals that fall outside the expected atrial-ventricular interval range may be attributable to noise generated by charging of INS 26 by charging device 46.

In some examples, the processor of ICD 16 may utilize in the P-R logic criterion at least one of an expected range of a ventricular-ventricular interval, atrial fibrillation evidence, evidence of potential far-field R-wave sensing, atrial-ventricular dissociation, or ventricular-ventricular regularity as an alternative or in addition to AV and VA interval patterns and/or an expected atrial-ventricular interval range. In any case, when the processor of ICD 16 determines that the P-R logic criterion indicates that generation of the charging signal by charging device 46 is not substantially interfering with operation of ICD 16, the processor may generate and transmit an instruction to the processor of charging device 46 to continue charging INS 26. However, when the P-R logic criterion indicates that the generation of the charging signal by charging device 46 is interfering with operation of ICD 16, the processor may generate and transmit an instruction to the processor of charging device 46 to cease charging of INS 26, modify at least one charging parameter, or the like. This process may iterate until the P-R logic criterion indicates that the generation of the charging signal by charging device 46 is not interfering with operation of ICD 16 or until the processor of ICD 16 generates and transmits an instruction to a processor of charging device 46 that causes the charging device 46 to cease charging of INS 26.

In some examples, a processor of ICD 16 may detect noise or interference above a threshold level in a sensed signal, where the noise or interference may be attributable to a charging signal generated by charging device 46. To verify that the detected noise or interference is indeed due to the charging signal, the processor of ICD 16 may generate and transmit an instruction to a processor of charging device 46 that causes the charging module of charging device 46 to cease the delivery of charging signals to INS 26. The processor of ICD 16 may continue to monitor the sensed electrical signal to determine if ceasing generation of the charging signal by charging device 46 changes the sensed signal (e.g., reduces the noise or interference in the sensed signal). The processor of ICD 16 then may generate and transmit an instruction to a processor of charging device 46 to initiate generation of a charging signal. Thereafter, the processor of ICD 16 may continue to monitor the sensed signal.

Techniques similar to those described below reference to FIGS. 8 and 11 with respect to determining whether electrical noise induced by the delivery of a charging signal by charging device 46 is excessive can be used to determine whether the electrical noise or other artifacts present in a sensed electrical activity decreases upon the cessation of charging of INS 26 by charging device 26. In some examples, if a characteristic of an electrical cardiac signal sensed by the ICD 16 while a charging signal is not being delivered by charging device 46 decreases relative to a characteristic of a signal sensed while charging device 46 is charging INS 26, the processor of ICD 16 may determine that that the noise or interference in a sensed signal is attributable to a charging signal generated by charging device 46. The signal characteristic can be, for example, a signal amplitude or a power level within a particular frequency band.

When the electrical signal by ICD 16 does not include noise or interference above a threshold level (e.g., sufficient to interfere with operation of ICD 16), the processor of ICD 16 may determine that the previously detected noise or interference was not due to the charging signal generated by charging device 46. The processor of ICD 16 then may do nothing (e.g., allow charging device 46 to continue to generate a charging signal) or may generate and transmit an indication to the processor of charging device 46 that indicates that generation of the charging signal is not interfering with operation of ICD 16. On the other hand, when the sensed signal does include noise or interference above a threshold level, the processor of ICD 16 may determine that the noise or interference is due to the charging signal generated by charging device 46. The processor of ICD 16 may then implement one or more of the mitigation techniques described herein, such as generating and transmitting an instruction to charging device 46 to modify an operating parameter of charging device 46, modifying an operating parameter of ICD 16, or the like.

In any of the above examples, charging device 46 and ICD 16 may communicate their respective operating parameters to each other in order to provide each other with information that may be relevant to controlling charging device 46 and/or ICD 16 to minimize any interference with ICD 16 that may arise from charging of INS 26. The operating parameters may include the values or other information with which a processor of charging device 46 or a processor of ICD 16 controls operation of the respective device. For example, ICD 16 may include a notch filter configured to filter out a certain detected frequency band from a sensed electrical signal or a low pass, high pass or bandpass filter configured to reject certain frequency bands from a sensed signal. A processor of ICD 16 may communicate the filter parameters to a processor of charging device 46, and the processor of charging device 46 may control charging device 46 to generate a charging signal that comprises a frequency band that will be filtered by the filter of ICD 16.

ICD 16 can directly or indirectly (e.g., via programmer 24 or INS 26) communicate other operating parameters, such as a threshold amplitude with which the processor of ICD 16 detects cardiac signals, a blanking period duration or rate, or the like, to charging device 46. Similarly, the processor of charging device 46 may directly or indirectly (e.g., via programmer 24 or INS 26) communicate operating parameters of charging device 46 to the processor of ICD 16, such as a charging signal burst duration or frequency, a charging signal bandwidth and frequency, or the like, and a processor of ICD 16 may control operation of ICD 16 accordingly. For example, the processor of ICD 16 may apply different types of filters to sensed electrical signals based on the operating parameters of charging device 46.

In some examples, a processor of charging device 46 may control a charging module of charging device 46 to generate and delivery a charging signal that includes encoded information, which may allow charging device 46 to communicate with at least one of ICD 16 and INS 26. In some examples, the processor of charging device 46 may generate a single charging signal that comprises a power sufficient to charge INS 26, where the single charging signal is modulated to encode information for communication with at least one of INS 26 and ICD 16, as described below. In other examples, charging device 46 may generate a first signal that comprises a power sufficient to charge INS 26 and a second signal that includes encoded information for communication with at least one of ICD 16 and INS 26. In these examples, the second signal may comprise a lower power than the first signal. In addition, the first and second signals may comprise different frequencies or modulations (e.g., frequency or amplitude modulation), and may be transmitted substantially simultaneously or at different times.

At least one of ICD 16 and INS 26 may be configured to receive and decode the information encoded in the charging signal. The processor of charging device 46 may control the charging module to encode information in the charging signal by, for example, varying the value of one or more charging signal parameters, such as frequency, amplitude, bandwidth, burst pattern, phase, duty cycle, or burst duration in a known manner, such that ICD 16 or INS 26 may sense the charging signals and extract information therefrom based on the known charging signal parameter values.

For example, the processor of charging device 46 may control the charging module to encode information in the charging signal, where the encoded information notifies ICD 16 that charging device 46 is initiating charging of INS 26. In some examples, the encoded information may include one or more operating parameters of charging device 46, such as, for example, a slew rate, an amplitude, frequency, bandwidth, burst pattern, or burst duration of the charging signal generated by charging device 46. ICD 16 may receive the encoded information and, for example, modify one or more sensing parameter values in order to reduce the possibility that ICD 16 senses the charging signal and mischaracterizes the charging signal as a cardiac signal. In some examples, ICD 16 may begin monitoring sensed signals to determine if the charging signal is introducing noise or other artifacts into the signal sensed by ICD 16. Techniques for determining whether noise or other artifacts are present within an electrical cardiac signal sensed by ICD 16 are described below. Based on the monitoring of the sensed signals, a processor of ICD 16 may determine whether one or more of the mitigation techniques described herein, such as enabling a filter, increasing a sensing threshold, increasing a blanking period, or the like, is desirable to reduce any interference effect that the charging signal may have on the operation of ICD 16. The processor of ICD 16 may also determine the extent of mitigation indicated. When the processor of ICD 16 determines that at least one mitigation technique is desirable, the processor may initiate that mitigation technique. In other examples, ICD 16 may receive the information and suspend sensing of cardiac signals.

In some examples, the processor of charging device 46 may control the charging module to generate a charging signal in a plurality of bursts, as described in further detail below, and may encode information in the charging signal by varying signal parameters on a burst-by-burst basis. For example, the processor of charging device 46 may generate the charging signal as a series of bursts and vary one or more signal parameters for each of the bursts. In some examples, the charging signal in a particular burst may be generated using the same charging signal parameter values. Using this technique, the processor of charging device 46 may encode information in the charging signal by associating particular burst shapes with information, where a burst shape may be defined by the charging signal parameter values used to generate the charging signal. For example, different burst shapes may be associated with specific instructions for ICD 16 or INS 26 or with different alphanumeric indicators, such as letters or numbers, and a plurality of burst shapes (symbols) may be arranged to form words or other indicators that are assigned a unique meaning or, more specifically, unique information relating to the operation of charging device 46, INS 26, or ICD 16.

In some examples, the alphanumeric indicator encoded in the charging signal from charging device 46 may be associated with an instruction stored in memory of at least one of programmer 24, ICD 16 or INS 26. Thus, upon extracting the alphanumeric indicator from the sensed charging signal from charging device 46, ICD 16 or INS 26 may reference a memory to determine what information was encoded in the stimulation signal. For example, ICD 16 or INS 26 may reference a memory to determine a modification to an operating parameter or operating mode associated with the alphanumeric indicator. As described in further detail below, the modification may include, for example, a modification to a sensing parameter of ICD 16, such as a filter used to sense cardiac signals, a threshold used to sense cardiac signals, or the like.

In another example, the processor of charging device 46 may encode information in the charging signal by generating a charging signal having one or more burst shapes that are associated with information, such as one or more alphanumeric indicators. A particular arrangement of multiple bursts may be associated with one or more alphanumeric indicators or with a specific instruction for ICD 16 or INS 26. The may be referred to as burst pattern encoding because information is encoded using different "patterns" of burst shapes, where a burst pattern includes more than one burst.

As another example, the processor of charging device 46 may encode information in the stimulation signal by varying one or more charging signal parameter values on a substantially continuous basis, e.g., as the processor controls a charging module to continue to generate the charging signal. This technique may allow information to be encoded in a substantially continuous charging signal, e.g., a charging signal that is not generated in discontinuous bursts.

The processor of charging device 46 may encode information in the charging signal by associating particular charging signal waveform shapes with an alphanumeric identifier or patterns in charging signal waveform shapes with alphanumeric identifiers, and may arrange the alphanumeric identifiers to form words or other indicators that have a unique predetermined meaning ICD 16 or INS 26 (or, alternatively, programmer 24 or another external computing device) may decode the charging signal using the same coding scheme with which the processor of charging device 46 encoded the stimulation signal. In other examples, the processor of charging device 46 may encode information in the stimulation signal by associating particular charging signal shapes with respective instructions for ICD 16 or INS 26, such as an instruction relating to a modification to a sensing parameter. In this manner, the processor of charging device 46 may be configured to encode information in charging signals using well known techniques in the art of telecommunication.

In other examples, charging device 46 may communicate with at least one of ICD 16 and INS 26, but without specifically encoding information in the charging signal. For example, charging device 46 may communicate with at least one of ICD 16 and INS 26 by generating a charging signal to charge INS 26. At least one of ICD 16 and INS 26 may modify an operating parameter or operating mode when ICD 16 or INS 26 detects the charging signal. For example, ICD 16 may withhold therapy for the time when charging device 46 is charging INS 26, or may modify one or more of the operating parameters described below.

At least one of ICD 16 and INS 26 may be configured to sense the charging signal generated by charging device 46 and process the signal to retrieve the encoded information. For example, ICD 16 and/or INS 26 may include signal processing circuitry for detecting the signal artifact in the sensed signal and decoding the information. ICD 16 and/or INS 26 then may use the decoded information to modify its operation. For example, if the information encoded in the charging signal specifies the duration of a charging signal burst, ICD 16 may modify a blanking period duration in order to prevent incorrect identification of a voltage induced by the charging signal as a cardiac parameter that indicates cardiac rhythm management therapy may be appropriate. In another example, ICD 16 may invoke additional signal processing techniques while charging device 46 charges INS 26, where the additional signal processing techniques utilize more complex techniques for monitoring the cardiac signal so as not to deliver unnecessary stimulation therapy to heart 14. The additional signal processing techniques may involve processing the sensed signal to remove the signal artifact resulting from the stimulation.

In some examples, INS 26 may communicate with ICD 16, or vice versa, by encoding information in a stimulation signal generated and delivered by INS 26. For example, INS 26 and ICD 16 may communicate with each other by encoding information in a respective stimulation signal, which may be transmitted to the other device through tissue of the patient. The information may be encoded in a stimulation signal by, for example, varying one or more signal parameters, e.g., the frequency (or pulse rate), wavelength (or pulse width), and duty cycle. The encoded information may provide information regarding the presence of charging device 46 or a charging signal being generated by charging device 46 to charge INS 26, such as the duration of the charging signal, a frequency of the charging signal, or other parameters of the charging signal described herein. Further details regarding communication between INS 26 and ICD 16 via encoding information in a stimulation signal may be found in commonly assigned U.S. patent application Ser. No. 12/363,215 to Krause et al., entitled "COMMUNICATION BETWEEN IMPLANTABLE MEDICAL DEVICES," and filed on Jan. 30, 2009.

In other examples, parameters regarding the operation of ICD 16 may be stored in memory of charging device 46, and a processor of charging device 46 may control operation of charging device 46 to mitigate interference between a charging signal generated by charging device 46 and operation of ICD 16. Alternatively or additionally, parameters regarding the operation of charging device 46 may be stored in memory of ICD 16, and a processor of ICD 16 may control operation of ICD 16 to mitigate interference between a charging signal generated by charging device 46 and operation of ICD 16. In addition, in other examples, programmer 24 may transmit the relevant operating parameter information to either or both ICD 16 and charging device 46.

While charging device 46 has been described as being a distinct device separate from programmer 24, in other examples, charging device 46 and programmer 24 may be incorporated in a single device. For example, a single device may allow a user to communicate with at least one of ICD 16 and INS 26 to retrieve information from or program therapy programs or information to ICD 16 or INS 26, as well as charge a rechargeable power source of one or both of ICD 16 and INS 26. The combined device may include any or all of the features or functionality ascribed to programmer 24 and charging device 46 herein.

Figure 3:
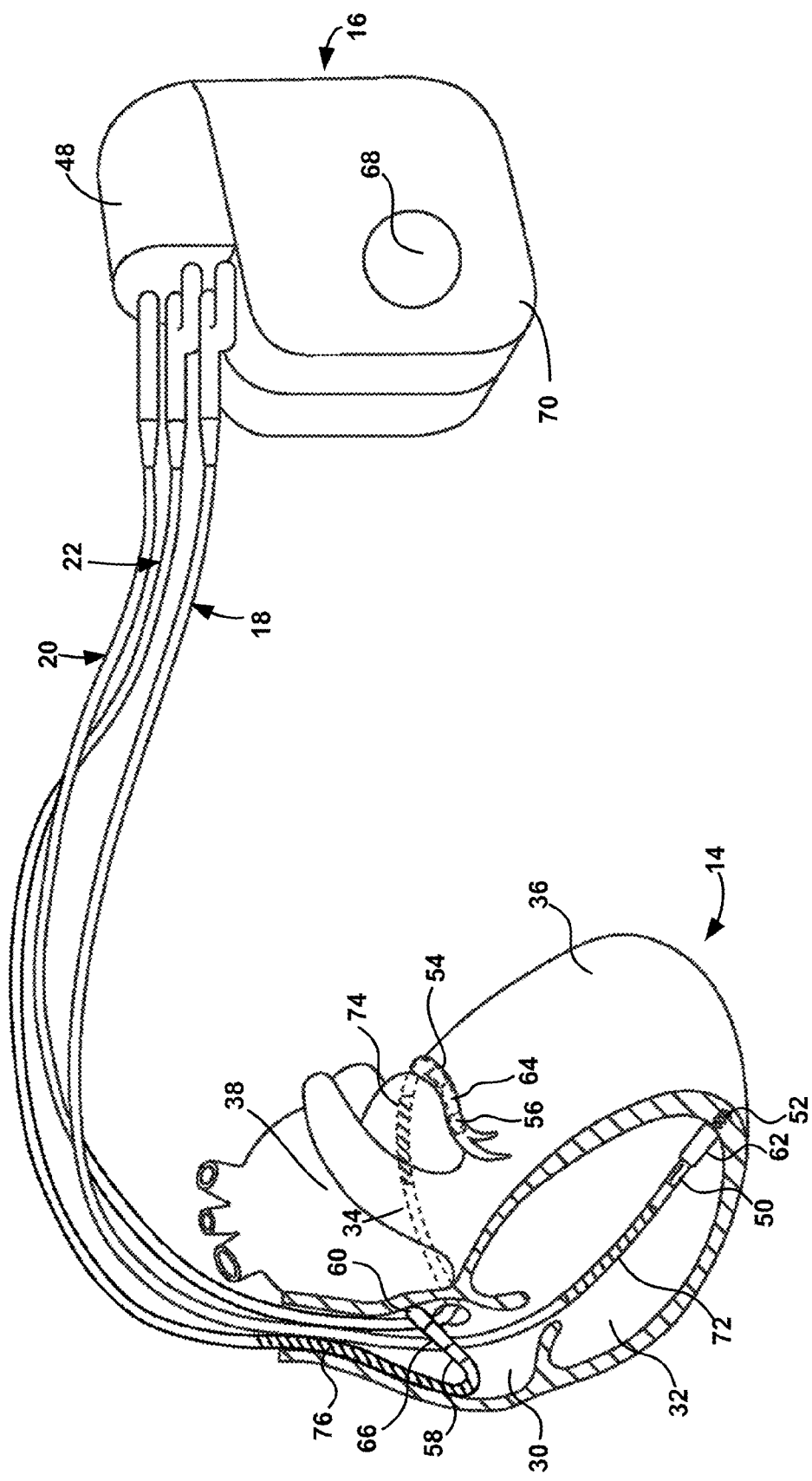
FIG. 3 is a conceptual diagram illustrating the ICD and associated leads of the therapy systems of FIGS. 1 and 2 in greater detail.

FIG. 3 is a conceptual diagram illustrating ICD 16 and leads 18, 20, 22 of therapy system 10 in greater detail. Leads 18, 20, 22 may be electrically coupled to a signal generator, a sensing module, or other modules of ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as lead configurations that do not include coiled conductors. In the illustrated example, bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54, and 58 may take the form of ring electrodes, and electrodes 52, 56, and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the conductors within the lead body of its associated lead 18, 20, 22, and thereby coupled to respective ones of the electrical contacts on the proximal end of leads 18, 20 and 22.

Electrodes 50, 52, 54, 56, 58, and 60 may sense electrical signals attendant to the depolarization and repolarization of heart 14. The electrical signals are conducted to ICD 16 via the respective leads 18, 20, 22. In some examples, ICD 16 also delivers pacing pulses via electrodes 50, 52, 54, 56, 58, and 60 to cause depolarization of cardiac tissue of heart 14. In some examples, as illustrated in FIG. 2, ICD 16 includes one or more housing electrodes, such as housing electrode 68, which may be formed integrally with an outer surface of hermetically-sealed outer housing 70 of ICD 16 or otherwise coupled to housing 70. In some examples, housing electrode 68 is defined by an uninsulated portion of an outward facing (e.g., facing tissue of patient 12 when ICD 16 is implanted within patient 12) portion of housing 70 of ICD 16. In some examples, housing electrode 68 comprises substantially all of housing 70. Divisions between insulated and uninsulated portions of housing 70 may be employed to define two or more housing electrodes. Any of the electrodes 50, 52, 54, 56, 58, and 60 may be used for unipolar sensing or pacing in combination with housing electrode 68. As described in further detail with reference to FIG. 4, housing 70 may enclose a signal generator that generates cardiac pacing pulses and defibrillation or cardioversion shocks, as well as a sensing module for monitoring the patient's heart rhythm.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, including, but not limited to, platinum, platinum alloy or other materials known to be usable in implantable defibrillation electrodes.

The configuration of therapy system 10 illustrated in FIGS. 1-3 are merely examples. In other examples, an ICD 16 may be coupled to two leads, as described below with reference to FIG. 4, or may be coupled to a single lead. In examples in which ICD is coupled to a single lead, the lead may carry two elongated electrodes (e.g., elongated electrodes 72, 76) that are used to deliver cardioversion or defibrillation shocks to heart 14.

In still other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14. In examples in which INS 26 is not implanted in patient 12, INS 26 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. For example, other examples of therapy systems may include three transvenous leads located as illustrated in FIGS. 1 and 3, and an additional lead located within or proximate to left atrium 38. As another example, other examples of therapy systems may include a single lead that extends from ICD 16 into right atrium 30 or right ventricle 32, or two leads that extend into a respective one of the right ventricle 32 and right atrium 30. An example of this type of therapy system is shown in FIG. 4.

Figure 4:
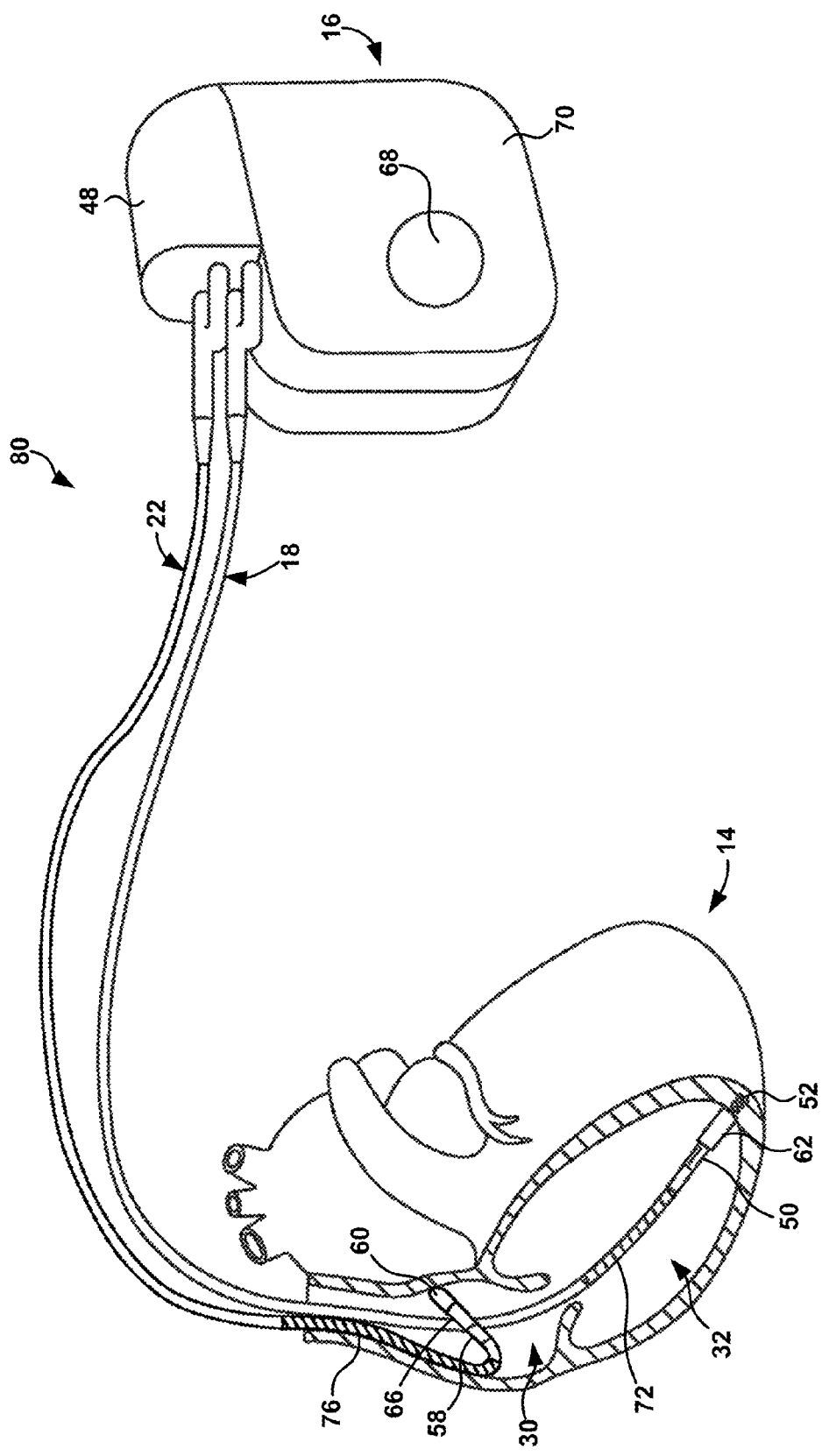
FIG. 4 is a conceptual diagram illustrating another example ICD lead configuration.

FIG. 4 is a conceptual diagram illustrating another example of therapy system 80, which is similar to therapy system 10 of FIGS. 1-3, but includes two leads 18, 22, rather than three leads. Leads 18, 22 are implanted within right ventricle 32 and right atrium 30, respectively. Therapy system 80 shown in FIG. 4 may be useful for providing defibrillation and pacing pulses to heart 14. Therapy system 80 may further include INS 26 (not shown in FIG. 4), which may be configured to deliver electrical stimulation therapy to one or more nerves, spinal cord 44 (FIG. 2), or other tissue sites within patient 12 in order to provide cardioprotective benefits to patient 12.

Figure 5:
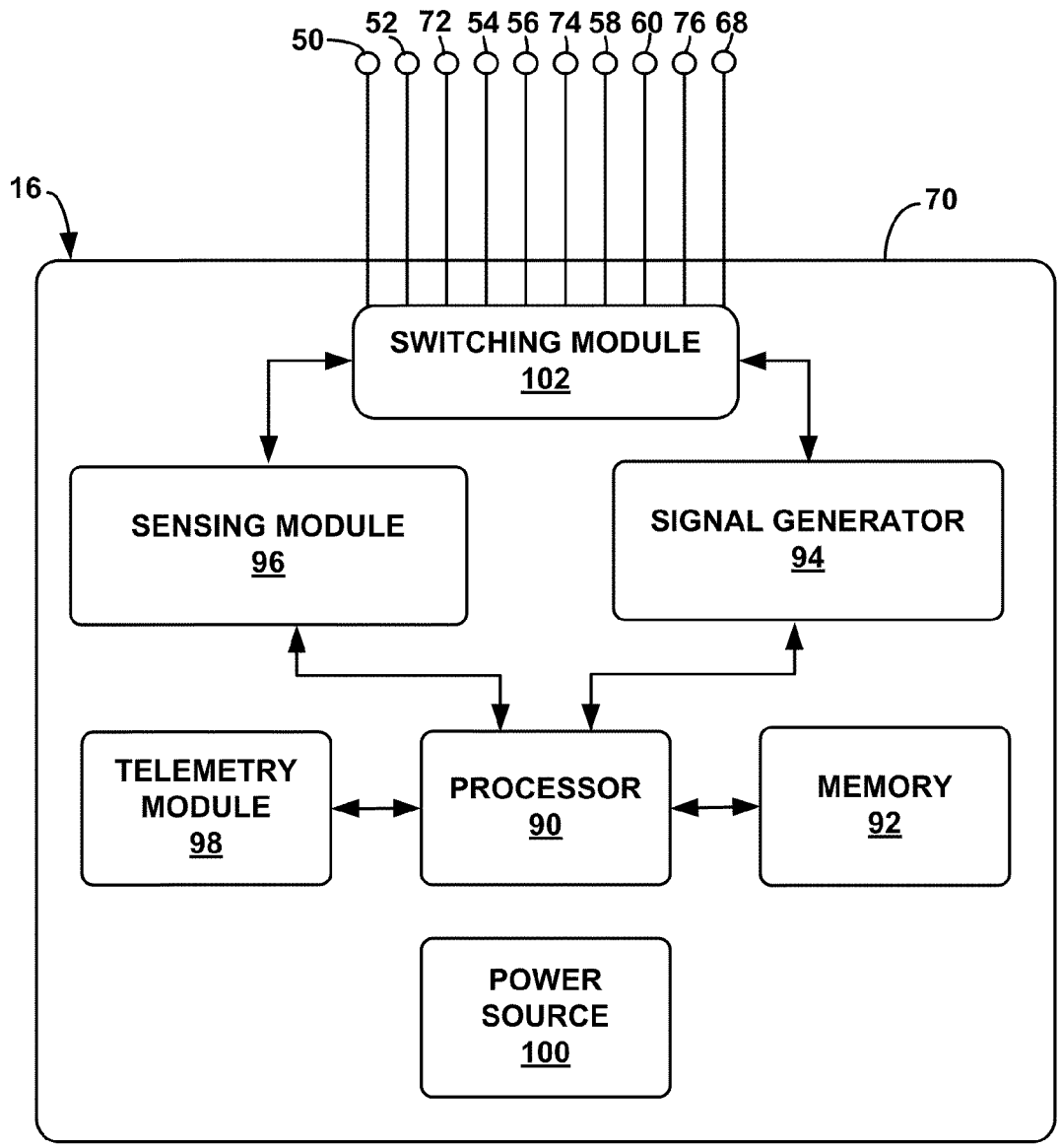
FIG. 5 is a functional block diagram of an example ICD that generates and delivers cardiac rhythm therapy to a heart of a patient.

FIG. 5 is a functional block diagram of an example configuration of ICD 16, which includes processor 90, memory 92, signal generator 94, sensing module 96, telemetry module 98, power source 100, and switching module 102. Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magnetoresistive random access memory (MRAM), or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls signal generator 94 to generate and deliver stimulation therapy to heart 14 according to a selected one or more of therapy programs, which may be stored in memory 92. Specifically, processor 90 may control signal generator 94 to deliver electrical pulses with the amplitudes, pulse widths, frequency, or electrode polarities specified by the selected one or more therapy programs.

Signal generator 94 is electrically coupled to electrodes 50, 52, 54, 56, 58, 60, 68, 72, 74, and 76, e.g., via switching module 102 and conductors of the respective lead 18, 20, 22, or, in the case of housing electrode 68, via switching module 102 and an electrical conductor disposed within outer housing 70 of ICD 16. Signal generator 94 is configured to generate and deliver electrical stimulation therapy to heart 14. For example, signal generator 94 may deliver defibrillation shocks to heart 14 via at least two of electrodes 68, 72, 74, 76. Signal generator 94 may deliver pacing pulses via ring electrodes 50, 54, 58 coupled to leads 18, 20, and 22, respectively, and/or helical electrodes 52, 56, and 60 of leads 18, 20, and 22, respectively. In some examples, signal generator 94 delivers pacing, cardioversion, or defibrillation stimulation in the form of electrical pulses or shocks. In other examples, signal generator may deliver one or more of these types of stimulation in the form of other signals, such as sine waves, square waves, or other substantially continuous time signals.

Signal generator 94 may be coupled to a switching module 102 and processor 90 may use switching module 102 to select, e.g., via a data/address bus, which of the available electrodes are used to deliver defibrillation pulses or pacing pulses. Switching module 102 may include a switch array, switch matrix, multiplexer, or any other type of switching device suitable to selectively couple stimulation energy to selected electrodes. In other examples, however, signal generator 94 may independently deliver stimulation to electrodes 50, 52, 54, 56, 58, 60, 68, 72, 74, and 76, or selectively sense via one or more of electrodes 50, 52, 54, 56, 58, 60, 68, 72, 74, and 76, without switching module 102. In some examples, processor 90 may control switching module 102 to switch operation of ICD 16 from a multiple-chamber sensing and pacing mode to a single-chamber sensing and pacing mode. For example, when all of electrodes 50, 52, 54, 56, 58, 60, 68, 72, 74, and 76 are being utilized, ICD 16 may be operating in a multiple-chamber sensing and pacing mode. As another example, when only electrodes 50, 52, and/or 72 are being utilized, ICD 16 may be operating in a single-chamber sensing and pacing mode.

Sensing module 96 may monitor signals from at least one of electrodes 50, 52, 54, 56, 58, 60, 68, 72, 74, and 76 in order to monitor electrical activity of heart 14, e.g., cardiac signals, via EGM signals. Sensing module 96 may also be coupled to switching module 102, which may select the available electrodes that are used to sense the heart activity, e.g., to switch between a single-chamber and multiple-chamber sensing and pacing mode, or to switch between respective single-chamber sensing and pacing modes. In some examples, processor 90 may select the electrodes that function as sense electrodes via switching module 102, e.g., by providing signals via a data/address bus. In some examples, sensing module 96 includes one or more sensing channels, each of which may comprise an amplifier. In response to the signals from processor 90, switching module 102 may couple the outputs from the selected electrodes to one of the sensing channels.

In some examples, one channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an EGM. In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

In some examples, processor 90 may include one or more components that enable implementation of the techniques described herein to minimize an artifact on a sensed signal that may be attributable to recharging of INS 26 by charging device 46 (FIG. 1). For example, processor 90, or, in some examples, sensing module 96, may apply a filter, such as a low pass filter, a band-stop filter, or a notch filter, to signals sensed by sensing module 96, whereby the filter is configured to attenuate a band of frequencies from the signals detected via one or more of electrodes 50, 52, 54, 56, 58, 60, 68, 72, 74, 76. As described in further detail below, the filter may be adjustable. That is, processor 90 may adjust the band of frequencies that the filter attenuates. In other examples, processor 90 may include the filter.

The filter may be configured or controlled to filter out a certain band of frequencies, such as, for example, a band of frequencies corresponding to a narrow bandwidth charging signal. Alternatively, in examples in which charging device 46 generates a charging signal comprising a known characteristic, the filter may be configured or controlled to filter out the charging signal or an artifact generated by the characteristic charging signal. In some examples in which charging device 46 generates a charging signal comprising a high frequency, processor 90 may include a low pass filter that attenuates the high frequency electrical noise induced by the charging signal.

Processor 90 may also adjust a sensing threshold with which processor 90 identifies cardiac signals. Processor 90 may only identify sensed signals that have a voltage amplitude greater than the sensing threshold value as electrical cardiac activity. For example, sensing module 96 may only transmit EGM signals above the sensing threshold value to processor 90 for timing analysis. As described below, the timing analysis may include an analysis of the sensed EGM signal for R-R intervals, P-P intervals, and so forth. For example, processor 90 may adjust increase the amplitude of the sensing threshold to mitigate interference from the charging signal, or may decrease the sensing threshold to ensure that sensing module detects features of the cardiac signal that may indicate a normal cardiac rhythm, a tachyarrhythmia, or a fibrillation. In some examples, processor 90 may adjust a threshold value with which processor 90 detects a cardiac parameter from a sensed cardiac signal. The cardiac parameter may comprise, for example, an R-wave of a P-wave.

If ICD 16 is configured to generate and deliver pacing pulses to heart 14, processor 90 may include pacer timing and control module, which may be embodied as hardware, firmware, software, or any combination thereof. The pacer timing and control module may comprise a dedicated hardware circuit, such as an ASIC, separate from other processor 90 components, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. In some examples, when the third letter is a "D," it may indicate that the signal is used for tracking purposes (e.g., DDD uses atrial sensing to trigger ventricular pacing).

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pacer timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

In some examples, processor 90 may adjust the duration of the blanking period. For example, processor 90 may increase or decrease the duration of the blanking period. As described in further detail below, in some examples, a processor of charging device 46 may control charging device 46 to deliver a charging signal in bursts that are delivered during the blanking period of ICD 16. Accordingly, processor 90 may increase the duration of the blanking period to increase the charging signal burst duration, while still mitigating interference between the charging signal and operation of ICD 16. In some examples, processor 90 may increase the blanking period to about 151 ms to about 500 ms. Processor 90 periodically may shorten the blanking period to the baseline blanking period (e.g., about 100 ms to about 240 ms) to monitor cardiac signals for presence of an arrhythmia, such as tachycardia or fibrillation.

During pacing, escape interval counters within the pacer timing/control module of processor 90 may be reset upon sensing of R-waves and P-waves. Signal generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by signal generator 94, and thereby control the basic timing of cardiac pacing functions, including anti-tachyarrhythmia pacing.

The value of the count present in the escape interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, processor 90 may not meet the requirements for triggering a therapeutic response.

In some examples, processor 90 may increase the threshold number of tachyarrhythmia events with which processor 90 identifies a tachyarrhythmia episode, such as a ventricular fibrillation episode or a ventricular tachycardia episode. For example, processor 90 may increase the threshold from three arrhythmia events to five arrhythmia events for a period of time. Processor 90 may occasionally or periodically reduce the threshold to the original threshold (e.g., three events) to confirm that a tachyarrhythmia episode is not occurring.

In some examples, processor 90 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 90 and any updating of the values or intervals controlled by the pacer timing and control module of processor 90 may take place following such interrupts. A portion of memory 92 may be configured as a plurality of recirculating buffers, capable of holding series of measured intervals, which may be analyzed by processor 90 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 90 in other examples.

In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds, e.g., the event detection intervals, for determining the R-R or P-P interval that indicates a tachyarrhythmia event may be stored within memory 92 of ICD 16. Processor 90 may periodically modify the thresholds for determining the R-R or P-P interval that is characterized as a tachyarrhythmia event. For example, processor 90 may increase the threshold (e.g., from 300 ms to 500 ms) while charging device 46 is delivering charging signals to INS 26, such that processor 90 does not mischaracterize the charging signals as an electrical cardiac signal that indicates the presence of an arrhythmia event. After temporarily increasing the event detection intervals, processor 90 may increase the event detection interval (e.g., while charging device 46 suspends the delivery of charging signals), in order to confirm that processor 90 is not missing the detection of any tachyarrhythmia events.

The number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by signal generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation shocks to heart 14, signal generator 94 may include a high voltage charge circuit and a high voltage output circuit. In the event that generation of a cardioversion or defibrillation shock is required, processor 90 may employ the escape interval counter to control timing of such cardioversion and defibrillation shocks, as well as associated refractory periods. In response to the detection of atrial or ventricular fibrillation or tachyarrhythmia requiring a cardioversion shock, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of signal generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging. Thereafter, timing of the delivery of the defibrillation or cardioversion shock by signal generator 94 is controlled by the cardioversion/defibrillation control module of processor 90. Following delivery of the fibrillation or tachycardia therapy, processor 90 may return signal generator 94 to a cardiac pacing function and await the next successive interrupt due to pacing or the occurrence of a sensed atrial or ventricular depolarization.

Signal generator 94 may deliver cardioversion or defibrillation shocks with the aid of an output circuit that determines whether a monophasic or biphasic pulse is delivered, whether housing electrode 68 serves as cathode or anode, and which electrodes are involved in delivery of the cardioversion or defibrillation shocks. Such functionality may be provided by one or more switches or switching module 102.

In some examples, processor 90 may control stimulation signal generator 94 or sensing module 96 to cease or interrupt operation. For example, processor 90 may determine that a noise level in a signal sensed by sensing module 96 is above a threshold level and is interfering with operation of ICD 16. When this occurs, processor 90 may temporarily interrupt operation of signal generator 94 so stimulation signals are not improperly delivered to heart 14. For example, processor 90 may prevent signal generator 94 from delivering stimulation signals to heart 14 based on signals detected by sensing module 96 while the noise level is above a threshold value. Processor 90 may then cease interrupting operation of signal generator 94 when the noise level is again below the threshold level. Examples for measuring levels of noise are described below with respect to FIG. 8.

In some examples, processor 90 may communicate an instruction to charging device 46 via telemetry module 98, as described in further detail below. The instruction may cause charging device 46 to cease charging INS 26 in an attempt to decrease the noise level, which may be due to an induced voltage in conductors of leads 18, 20, 22. Processor 90 may then cease interruption of operation of signal generator 94 once charging device 46 ceases charging INS 26 and the noise level decreases below the threshold value. That is, once processor 90 receives an indication that charging device 46 has stopped charging INS 26, processor 90 may continue normal control of signal generator 94, e.g., to generate cardiac rhythm therapy.

In some examples, processor 90 may begin monitoring signals sensed by sensing module 96 to determine if the charging signal generated by charging module 46 is introducing noise or other artifacts into the sensed signal. Based on the monitoring of the sensed signals, processor 90 may determine whether one or more of the mitigation techniques described herein, such as enabling a filter configured to remove at least part of the signal artifact attributable to the charging signal, increasing a sensing threshold, increasing a blanking period, or the like, is indicated. Processor 90 may also determine the extent of mitigation indicated. When processor 90 determines that at least one mitigation technique is indicate, processor 90 may initiate that mitigation technique.

In some examples, processor 90 may communicate an instruction to the processor of charging device 46 prior to the processor of charging device 46 initiating generation of the charging signal. The instruction may be in response to a communication received from the processor of charging device 46 requesting an indication of whether an IMD (e.g., ICD 16) other than the target device to be charged (e.g., INS 26) is implanted in patient 12, or whether ICD 16 is able to utilize at least one of the interference mitigation techniques described herein. Processor 90 may generate and transmit a response to the processor of charging device 46, which may indicate that the processor of charging device 46 may or may not initiate charging of INS 26, or which may include at least one operating parameter of ICD 16. The processor of charging device 46 may then interpret the indication received from processor 90 and initiate generation of a charging signal, if appropriate, or may generate an alert to a user. The alert may indicate that the user may initiate charging or that charging is not recommended, as indicated by the communication from processor 90 to the processor of charging device 46.

In other examples, processor 90, upon detecting a charging signal, may generate and transmit an indication to the processor of charging device 46 that ICD 16 is implanted in patient 12. In some examples, the processor of charging device 46 then may generate a more conservative (e.g., lower amplitude) charging signal so as to mitigate interference with operation of ICD 16.

In some examples, processor 90 may detect noise or interference above a threshold level in a signal sensed by sensing module 96, which may be attributable to a charging signal generated by charging device 46. To verify that the noise or interference is indeed due to the charging signal, processor 90 may generate and transmit via telemetry module 98 an instruction to a processor of charging device 46 to cease generate of a charging signal. Processor 90 may continue to monitor the sensed signal sensed by sensing module 96 to determine if the cessation of the delivery of the charging signal by charging device 46 changes the signal sensed by sensing module 96 (e.g., reduces the noise or interference in the sensed signal). Processor 90 then may generate and transmit via telemetry module 98 an instruction to a processor of charging device 46 to initiate generation of a charging signal. Processor 90 may continue to monitor the signal sensed by sensing module 96.

When the signal sensed by sensing module 96 does not include noise or interference above a threshold level (e.g., sufficient to interfere with operation of ICD 16), processor 90 may determine that the previously detected noise or interference was not due to the charging signal generated by charging device 46. Processor 90 then may do nothing (e.g., allow charging device 46 to continue to generate a charging signal) or may generate and transmit an indication to the processor of charging device 46 that generation of the charging signal is not interfering with operation of ICD 16. On the other hand, when the signal sensed by sensing module 96 does include noise or interference above a threshold level, processor 90 may determine that the noise or interference is due to the charging signal generated by charging device 46. Processor 90 then may implement one or more of the mitigation techniques described herein, such as generating an transmitting an instruction to charging device 46 to modify generation of the charging signal, modifying an operating parameter of ICD 16, or the like.

Telemetry module 98 includes any suitable hardware, firmware, software or any combination thereof for communicating with another device, such as programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer.

In some examples, processor 90 may transmit atrial and ventricular heart signals (e.g., EGM signals) produced by atrial and ventricular sense amp circuits within sensing module 96 to programmer 24. The atrial and ventricular heart signals, as well as other physiological parameters of patient 12 sensed by ICD 16 may be transmitted to programmer 24 or another device for diagnostic purposes, e.g., to diagnose a severity of the patient's condition. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Processor 90 may also communicate with charging device 46 via telemetry module 98. Processor 90 may communicate parameters or indications to charging device 46, such as, for example, an indication of the presence of ICD 16 implanted in patient 12, or an indication that a noise level detected by ICD 16 is above a threshold value and may be interfering with operation of ICD 16. As other examples, processor 90 may communicate other parameters to charging device 46, such as a threshold amplitude value above which noise may interfere with the sensing of cardiac signals by ICD 16, intervals with which processor 90 identifies arrhythmia events (e.g., fibrillation events), a blanking period duration or rate, or the like.

Processor 90 also may receive communications from charging device 46 via telemetry module 98. The communications may include, for example, instructions to modify operation of ICD 16. For example, charging device 46 may communicate an instruction to processor 90 to modify a blanking period duration, to modify a threshold noise value or threshold value above which processor 90 identifies a cardiac parameter from a cardiac signal, or to control some other parameter of an operating mode of ICD 16.

In some examples, processor 90, and/or sensing module 96, may be configured to detect information encoded in a charging signal generated by charging module 46, a stimulation signal generated by INS 26, or both. For example, processor 90 or sensing module 96 may include signal processing circuitry for detecting the signal artifact in the sensed signal and decoding the information. Processor 90 then may use the decoded information to modify operation of ICD 16. For example, if the information encoded in the charging signal specifies the duration of a charging signal burst, processor 90 may modify a blanking period duration in order to help prevent incorrect identification of a voltage induced by the charging signal as a cardiac parameter that indicates need for stimulation therapy.

In another example, processor 90 may invoke an additional signal processing technique while charging device 46 charges INS 26, where the additional signal processing techniques may utilize more different, and, in some cases, more complex techniques, for monitoring the cardiac signal so as not to deliver unnecessary stimulation therapy to heart 14. The additional signal processing techniques may involve processing the sensed signal to remove the signal artifact resulting from the stimulation. Further details regarding communication between INS 26 and ICD 16 via encoding information in a stimulation signal may be found in commonly-assigned U.S. patent application Ser. No. 12/363,215 to Krause et al., entitled "COMMUNICATION BETWEEN IMPLANTABLE MEDICAL DEVICES," and filed on Jan. 30, 2009.

Processor 90 may also implement other techniques to reduce the effects of a charging signal from charging device 46 on the operation of ICD 16. For example, as described briefly above, processor 90 may be configured to provide either single-chamber pacing and sensing or multiple-chamber pacing and sensing. In some examples in which processor 90 is configured to provide multiple-chamber pacing and sensing, processor 90 may independently adjust a blanking period for each of the chambers.

In some examples, processor 90 of ICD 16 may temporarily switch signal generator 94 and sensing module 96 from a multiple-chamber pacing and sensing mode to a single-chamber pacing and sensing mode when processor 90 determines that a charging signal from charging device 46 (FIG. 1) is interfering with sensing of electrical cardiac signals within some, but not all, chambers of heart 14. Processor 90 of ICD 16 may periodically switch signal generator 94 and sensing module 96 to a multiple-chamber pacing and sensing mode to determine whether the charging signal is still interfering with sensing of electrical cardiac signals within other chambers of heart 14. Once processor 90 determines that the charging signal is no longer interfering with sensing within the other chambers, processor 90 may return ICD 16 to a multiple-chamber pacing and sensing mode.

Processor 90 may implement various techniques to mitigate the effects of the delivery of charging signals by charging device 46 on the operation of ICD 16. As previously described, in some examples, processor 90 increases the number of intervals to detect, with which the processor of ICD 16 identifies and detects an arrhythmia episode that triggers some response (e.g., delivery of a defibrillation shock). For example, the processor of ICD 16 may increase the number of intervals to detect from three arrhythmia events to five arrhythmia events for a period of time. Processor 90 of ICD 16 may occasionally or periodically reduce the threshold to the original threshold (e.g., three events) to confirm that an arrhythmia episode is not occurring.

In some examples, processor 90 of ICD 16 also adjusts an arrhythmia event detection interval with which the processor detects an arrhythmia in order to mitigate the effects of the delivery of charging signals by charging device 46 on the operation of ICD 16. In some examples, processor 90 detects an arrhythmia event if the interval between R-waves or P-waves of subsequent cardiac signals is less than or equal to the arrhythmia detection interval. In this way, the arrhythmia event detection interval may define am upper frequency limit of an EGM signal indicating an arrhythmia event. From time-to-time, contemporaneous with the delivery of a charging signal by charging device 46, processor 90 may temporarily decrease the detection interval to be more discerning of arrhythmia events and help prevent the charging signal from interfering with the arrhythmia event detection by ICD 16, and may periodically return the detection interval cutoff to the original value to determine if any potential arrhythmia events detected with the longer arrhythmia event interval are being missed. For example, processor 90 of ICD 16 may decrease the detection interval cutoff from about 400 ms to about 300 ms temporarily, and then periodically return the detection rate cutoff to 400 ms. The detection interval as well as the decreased detection interval may be stored by memory 92 of ICD 16 or a memory of another device (e.g., programmer 24).

In some examples, processor 90 may enable a rate stability criterion in order to mitigate the effects of the delivery of charging signals by charging device 46 on the operation of ICD 16. Thus, the rate stability criterion may be enabled while charging device 46 charges INS 26. A rate stability criterion requires R-R intervals to be relatively consistent (e.g., stable) before interpreting the R-R interval as an arrhythmia. This may help avoid detecting irregularly conducted atrial fibrillation. In many examples, noise appears as an irregular signal in a sensed cardiac signal, so a rate stability criterion may mitigate the effect of noise on detection of heart arrhythmias.

In some examples, processor 90 may utilize a wavelet criterion while charging device 46 charges INS 26 to attempt to mitigate the effect of noise on detection of heart arrhythmias. A wavelet criterion requires the morphology of a cardiac signal detected by EGM to change before interpreting cardiac signal parameters as representing a true arrhythmia. Because noise may appear as an irregular signal in the sensed cardiac signal, implementation of a wavelet criterion may also mitigate the effect of noise on detection of a true heart arrhythmia.

For example, noise due to charging of INS 26 by charging device 46 may cause the wavelet criterion to return an incorrect result (e.g., the wavelet criterion may indicate a change in the morphology of the cardiac signal, when the change is caused by noise, not a change to the underlying cardiac signal). To determine whether the result of the wavelet criterion is due to the charging signal, processor 90 may first determine a wavelet template by fitting a wavelet function to a sensed cardiac signal when charging device 46 is not delivering the charging signal. For example, processor 90 may determine at least one coefficient or exponent in a polynomial, rational function, exponential function, or the like to produce a wavelet function that fits at least a portion of the sensed cardiac signal when charging device 46 is not delivering the charging signal. Alternatively, processor 90 may determine a wavelet template that comprises an array including a plurality of amplitude values and associated time values that substantially fit at least a portion of the sensed cardiac signal when charging device 46 is not delivering the charging signal. Processor 90 may store the wavelet function or wavelet criterion in memory 92 as a wavelet function template or a wavelet criterion threshold.

Processor 90 then may generate and transmit an instruction to processor 150 of charging device 46 that causes charging module 160 of charging device 46 to initiate the delivery of charging signals to INS 26. Processor 90 may apply the wavelet template to a sensed cardiac signal when charging device 46 is delivering the charging signal to INS 26 to determine a wavelet score indicative of a similarity between wavelet template and the sensed cardiac signal when charging device 46 is delivering a charging signal to INS 26. For example, processor 90 may cross-correlate the wavelet template and the sensed cardiac signal to determine the wavelet score indicative of similarity between the template and the sensed cardiac signal.

When the wavelet score indicates that the wavelet template and the sensed cardiac signal are sufficiently similar (e.g., the wavelet score based on cross-correlation between the wavelet template and the sensed cardiac signal is greater than a threshold value), processor 90 may determine that the generation of the charging signal by charging device 46 is not substantially interfering with operation of ICD 16. However, when the wavelet score indicates that the wavelet template and the sensed cardiac signal are not sufficiently similar (e.g., the wavelet score based on cross-correlation between the wavelet template and the sensed cardiac signal is less than a threshold value), processor 90 may determine that the generation of the charging signal by charging device 46 is interfering with operation of ICD 16, and may cause processor 150 of charging device 46 to cease charging of INS 26, modify at least one charging parameter, or the like. Processor 90 may iterate this process until the wavelet score indicates that the wavelet template and the sensed cardiac signal are substantially similar (e.g., the wavelet score based on cross-correlation is greater than a threshold value) or until processor 90 generates and transmits an instruction to processor 150 of charging device 46 that causes the charging device 46 to cease charging of INS 26.

In some examples, processor 90 may implement a P-R logic criterion while charging device 46 charges INS 26 to attempt to mitigate the effect of noise on detection of heart arrhythmias. A P-R logic criterion utilizes pattern analysis of atrial (e.g., P-waves of an EGM) and ventricular (e.g., R-waves of an EGM) events to analyze whether a detected fast rhythm (e.g., based on an EGM) is due to a ventricular tachycardia or ventricular fibrillation rhythm, or whether the fast rhythm is being driven by a supra-ventricular tachycardia (e.g., a sinus tachycardia, atrial fibrillation, atrial flutter, or the like). In some examples, electrical noise caused by operation of charging device 46 may be sensed by processor 90 via an atrial electrode (e.g., electrode 58 or electrode 60), and may thus appear on an EGM to be additional atrial events. A P-R logic criterion may also mitigate the effect of noise on detection of a true heart arrhythmia.

For example, noise due to charging of INS 26 by charging device 46 may cause the P-R logic criterion to return an incorrect result (e.g., the P-R logic criterion may indicate a tachycardia or fibrillation event that is not actually occurring). To determine whether the result of the P-R logic criterion is due to the charging signal, processor 90 may first apply a P-R logic criterion to a sensed cardiac signal when charging device 46 is not delivering a charging signal to INS 26 to determine a first P-R logic result. A P-R logic result may include, for example, a determination that a ventricular tachycardia or ventricular fibrillation rhythm has occurred, or whether a supra-ventricular tachycardia rhythm (e.g., a sinus tachycardia, atrial fibrillation, atrial flutter, or the like) has occurred. In some examples, the P-R logic result may simply determine whether a rhythm is caused by a ventricular tachycardia, a ventricular fibrillation or a supra-ventricular tachycardia.

In other examples, if a supra-ventricular tachycardia has occurred, the P-R logic result may determine what type of supra-ventricular tachycardia has occurred. Processor 90 may then generate and transmit an instruction to a processor of charging device 46 that causes the charging module of charging device to initiate the delivery of charging signals to INS 26. Processor 90 may apply the P-R logic criterion to a sensed cardiac signal when charging device 46 is delivering the charging signal to INS 26 to determine a second P-R logic result. Processor 90 may then compare the first P-R logic result to the second P-R logic result. When the first P-R logic result is different than the second P-R logic result, processor 90 may generate and transmit an instruction to a processor 150 of charging device 46 (FIG. 8) that causes the charging device 46 to cease charging of INS 26, modify at least one charging parameter used to generate the charging signal, or the like.

In examples in which processor 90 transmits an instruction to processor 150 of charging device 46 to modify at least one charging parameter, processor 90 may again apply the P-R logic criterion to a sensed cardiac signal when charging device 46 is not delivering the charging signal to determine a first P-R logic result. Processor 90 may also apply the P-R logic criterion to a sensed cardiac signal when charging device 46 is delivering the modified charging signal to INS 26 to determine a second P-R logic result, and may compare the first and second P-R logic results to determine if the first and second P-R logic results are substantially similar or different. When the first and second P-R logic results are substantially similar, processor 90 may determine that the generation of the charging signal by charging device 46 is not substantially interfering with operation of ICD 16. However, when the first and second P-R logic results are different, processor 90 may determine that the generation of the charging signal by charging device 46 is interfering with operation of ICD 16, and may cause processor 150 of charging device 46 to cease charging of INS 26, modify at least one charging parameter, or the like. This process may iterate until the first and second P-R logic results are substantially similar or until processor 90 generate and transmit an instruction to 150 processor of charging device 46 that causes the charging device 46 to cease charging of INS 26.

As another example, processor 90 may apply a P-R logic criterion that is configured to distinguish noise induced by charging of INS 26 by charging device 46 from true a ventricular tachycardia rhythm or a true ventricular fibrillation rhythm. For example, processor 90 may utilize at least one of an AV interval pattern, a VA interval pattern, an expected range of a ventricular-ventricular interval, an expected range of an AV interval, atrial fibrillation evidence, evidence of potential far-field R-wave sensing, atrial-ventricular dissociation, or ventricular-ventricular regularity to determine whether a sensed cardiac signal includes events that are caused by noise rather than true atrial or ventricular events.

In some examples, processor 90 may analyze AV and VA interval patterns of a sensed cardiac signal by categorizing the atrial rhythm according to a number of apparent atrial events in a ventricular-ventricular interval. Additionally, processor 90 may determine zones within the ventricular-ventricular interval during which the apparent atrial events occur. As described above, noise induced by charging of INS 26 by charging device 46 may appear as an atrial event on an EGM. By analyzing the number of apparent atrial events and the zones during which the apparent atrial events occur, processor 90 may determine that at least one of the apparent atrial events is likely noise induced by charging of INS 26 by charging device 46. For example, processor 90, with the aid of the P-R logic criterion, may determine that the detected number of atrial events and zones during which the detected atrial events occur do not correspond to the expected number of atrial events or zones for true atrial activity. The expected number of atrial events or zones for true atrial activity may be stored by ICD 16, programmer 24, or another device. On this basis, the processor may conclude that the sensed cardiac signal includes events that are caused by noise rather than true atrial events.

In some examples, processor 90 may analyze a range of atrial-ventricular intervals by first calculating a mean atrial-ventricular interval from a number of previous atrial-ventricular interval values. Processor 90 may construct an expected atrial-ventricular interval range utilizing mean atrial-ventricular interval and absolute differences between the recent atrial-ventricular intervals and the atrial-ventricular interval range. Subsequent atrial-ventricular intervals that fall outside the expected atrial-ventricular interval range may be excluded from further analysis. In this way, cardiac signals including noise that manifests as apparent atrial events may be excluded by the processor from analysis, because the atrial-ventricular interval may fall outside the expected atrial-ventricular interval range. At least some of the atrial-ventricular intervals that fall outside the expected atrial-ventricular interval range may be attributable to noise generated by charging of INS 26 by charging device 46.

In some examples, processor 90 may utilize in the P-R logic criterion at least one of an expected range of a ventricular-ventricular interval, atrial fibrillation evidence, evidence of potential far-field R-wave sensing, atrial-ventricular dissociation, or ventricular-ventricular regularity as an alternative or in addition to AV and VA interval patterns and/or an expected atrial-ventricular interval range. In any case, when processor 90 determines that the P-R logic criterion indicates that generation of the charging signal by charging device 46 is not substantially interfering with operation of ICD 16, processor 90 may generate and transmit an instruction to the processor of charging device 46 to continue charging INS 26. However, when the P-R logic criterion indicates that the generation of the charging signal by charging device 46 is interfering with operation of ICD 16, processor 90 may generate and transmit an instruction to processor 150 of charging device 46 to cease charging of INS 26, modify at least one charging parameter, or the like. This process may iterate until the P-R logic criterion indicates that the generation of the charging signal by charging device 46 is not interfering with operation of ICD 16 or until processor 90 generates and transmits an instruction to processor 150 of charging device 46 that causes the charging device 46 to cease charging of INS 26.

The various components of ICD 16 are coupled to power source 100, which may include a rechargeable or non-rechargeable battery. A non-rechargeable battery may be selected to last for several years, while a rechargeable battery may be inductively charged from an external device, such as charging device 46, e.g., on a daily or weekly basis. As previously indicated, in some examples, charging device 46 may be configured to charge power source 100 of ICD 16.

In some examples, data from sensing module 96 may be uploaded to a remote server, from which a clinician or another user may access the data to determine whether a potential sensing integrity issue exists or whether the measured physiological parameter values indicate patient 12 requires medical attention. An example of a remote server includes the CareLink Network, available from Medtronic, Inc. of Minneapolis, Minn.

Figure 6:
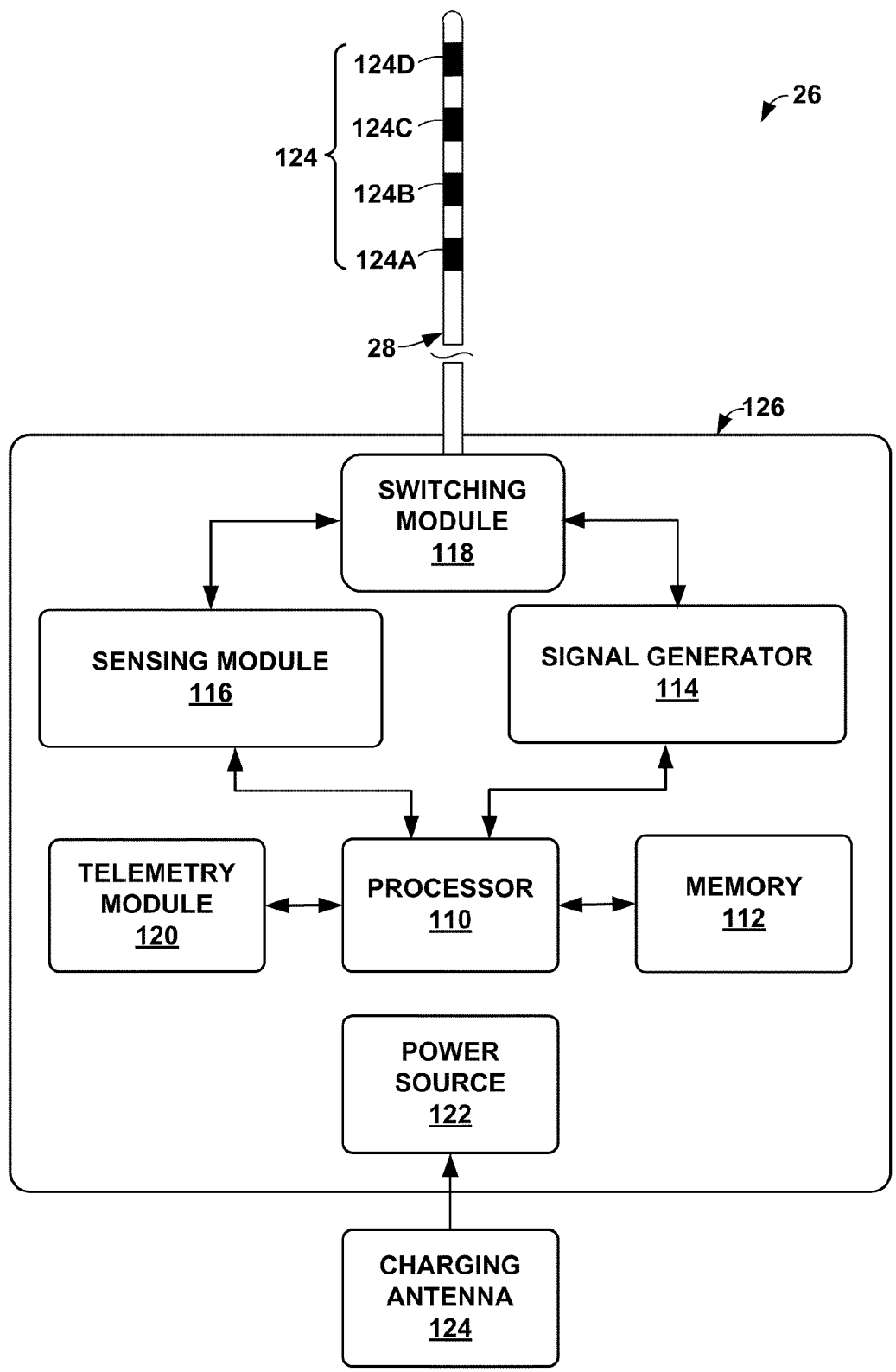
FIG. 6 is a functional block diagram of an example INS that generates and delivers electrical stimulation to a target tissue site within a patient.

FIG. 6 is a functional block diagram of an example INS 26. INS 26 includes processor 110, memory 112, signal generator 114, sensing module 116, switching module 118, telemetry module 120, and power source 122. In the example shown in FIG. 6, processor 110, memory 112, signal generator 114, sensing module 116, switching module 118, telemetry module 120, and power source 122 are enclosed within outer housing 126, which may be, for example a hermetically sealed outer housing. As shown in FIG. 6, signal generator 114 is coupled to lead 28 either directly or indirectly (e.g., via a lead extension). Alternatively, signal generator 114 may be coupled more than one lead directly or indirectly (e.g., via a lead extension, such as a bifurcating lead extension that may electrically and mechanically couple to two leads) as needed to provide neurostimulation therapy to patient 12.

In the example illustrated in FIG. 6, lead 28 includes electrodes 124A-124D (collectively referred to as "electrodes 124"). Electrodes 124 may comprise ring electrodes. In other examples, electrodes 124 may be arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 124 illustrated in FIG. 6 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 124.

Memory 112 includes computer-readable instructions that, when executed by processor 110, cause INS 26 to perform various functions. Memory 112 may include any volatile, non-volatile, magnetic, optical, or electrical media, such as a RAM, ROM, NVRAM, EEPROM, flash memory, or any other digital media. Memory 112 may store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for measuring impedance or communicating with ICD 16 via electrodes 124. Memory 112 may also store an indication that ICD 16 is implanted in patient 12, and may store at least one operating parameter of ICD 16 (e.g., a blanking period duration).

Signal generator 114 generates stimulation signals, which may be pulses as primarily described herein, or continuous time signals, such as sine waves, for delivery to patient 12 via selected combinations of electrodes 124. In addition, signal generator 114 may also generate an electrical signal between two or more electrodes 124 in order to measure an electrical parameter value indicative of impedance of an electrical path between the two or more electrodes 124.

Processor 110 controls signal generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Signal generator 114 and sensing module 116 are coupled to switching module 118. Processor 110 may control switching module 118 to apply the stimulation signals generated by signal generator 114 to selected combinations of electrodes 124. In particular, switching module 118 couples stimulation signals to selected conductors within leads 28, which, in turn, deliver the stimulation signals across selected electrodes 124. In addition, in some examples, processor 110 may control switching module 118 to connect a selected combination of electrodes 124 to sensing module 116 to sense electrical signals. Switching module 118 may be a switch array, switch matrix, multiplexer, or any other type of switching device suitable to selectively couple stimulation energy to selected electrodes. Hence, signal generator 114 is coupled to electrodes 124 via switching module 118 and conductors within leads 28. In some examples, INS 26 does not include switching module 118.

Signal generator 114 may be a single or multi-channel signal generator. In particular, signal generator 114 may be capable of delivering, a single stimulation pulse, multiple stimulation pulses, or a continuous signal at a given time via a single electrode combination or multiple stimulation pulses at a given time via multiple electrode combinations. In some examples, however, signal generator 114 and switching module 118 may be configured to deliver multiple channels on a time-interleaved basis. In this case, switching module 118 serves to time division multiplex the output of signal generator 114 across different electrode combinations at different times to deliver multiple programs or channels of stimulation energy to patient 12.

Sensing module 116 may also be configured to monitor signals from at least one of electrodes 124 in order to monitor physiological parameters of patient 12, such as EGM/ECG signals of heart 14 (FIG. 1), tissue impedance, respiration, or the like.

Telemetry module 120 supports wireless communication between INS 26 and ICD 16, external programmer 24 (FIG. 1) or another computing device under the control of processor 110. Processor 110 of INS 26 may receive, as updates to programs, values for various stimulation parameters such as amplitude and electrode combination, from programmer 24 via telemetry module 120. The updates to the therapy programs may be stored within memory 112.

Processor 110 may also communicate with charging device 46 via telemetry module 120. For example, charging device 46 may interrogate processor 110 via telemetry module 120 to determine if INS 26 is, in fact, configured to be charged by charging device 46. Processor 110 may communicate an identifier to charging device 46, after which charging device 46 may commence charging INS 26. In other examples, processor 110 may communicate an instruction to the processor of charging device 46 prior to the processor of charging device 46 initiating generation of the charging signal. The instruction may be in response to a communication received from the processor of charging device 46 requesting an indication of whether a second IMD (e.g., ICD 16) in addition to the target device to be charged (e.g., INS 26) is implanted in patient 12, or whether ICD 16 is able to utilize at least one of the interference mitigation techniques described herein.

Processor 110 may generate and transmit a response via telemetry module 120 to the processor of charging device 46, which may indicate that the processor of charging device 46 may or may not initiate charging of INS 26, may indicate the presence of ICD 16, or may include at least one operating parameter of ICD 16 (e.g., a sensing threshold or blanking period duration and timing). The processor of charging device 46 may then interpret the indication received from processor 110 and initiate generation of a charging signal, if appropriate, or may generate an alert to a user. The alert may indicate that the user may initiate charging or that charging is not recommended, as indicated by the communication from processor 110 to the processor of charging device 46.

In some examples, charging device 46 may begin charging INS 26 in bursts until receiving the identifier from processor 110, at which time charging device 46 may commence a different charging program, such as, for example, continuous charging of INS 26.

In some examples, processor 110 may generate an instruction to charging device 46 to adjust an amplitude of a charging signal generated by charging device 46. For example, the processor of charging device 46 may initiate charging of INS 26 by generating a charging signal with a predetermined initial amplitude, which may be a relatively low amplitude, an intermediate amplitude, or a relatively high amplitude. Processor 110 may monitor the amplitude of the charging signal received by a charging antenna 124, and may determine whether the amplitude of the received charging signal is too low, within an acceptable range, or greater than necessary.

In some examples, processor 110 determine whether the amplitude of the charging signal received by charging antenna 124 is within or outside of the acceptable range by comparing the amplitude of the received charging signal to one or more threshold amplitudes. Processor 110 may monitor an amplitude of the received charging signal in one or more frequency bands of the received charging signal. The amplitude may be a mean or median amplitude (e.g., a peak-to-peak amplitude), a highest amplitude (e.g., a peak-to-peak amplitude), a root means square (RMS) amplitude, an amplitude that is equal to a certain percentage (e.g., about 95%) of the highest amplitude, and the like. Processor 110 may compare the amplitude to a first threshold amplitude, e.g., a lower threshold amplitude, to determine whether the amplitude of the received charging signal is greater than the lower threshold amplitude. Processor 110 also may compare the amplitude to a second threshold amplitude, e.g., an upper threshold amplitude, to determine whether the amplitude of the received charging signal is less than the upper threshold amplitude. The upper and lower threshold amplitudes may be stored in memory 112 of INS 26 or a memory of another device (e.g., programmer 24 or memory 92 of ICD 16).

Based on the comparison of the amplitude of the received charging signal to the upper and lower threshold amplitudes, processor 110 then may transmit an instruction to the processor of charging device 46 to adjust the amplitude of the charging signal generated by charging device 46 such that the amplitude of the charging signal received by INS 26 falls within the acceptable range (e.g., the amplitude of the received charging signal is greater than the lower threshold amplitude and less than the upper threshold amplitude). In some examples, this process may iterate until the charging signal received by INS 26 falls within the acceptable range. Such a process may result in charging device 46 generating a charging signal that is sufficient to charge INS 26, but not excessive. In this way, ICD 16 or charging device 46 may not need to initiate additional interference mitigation techniques, or the extent of any additional interference mitigation techniques may be reduced.

In some examples, processor 110 may communicate with processor 90 of ICD 16, or vice versa, e.g., via respective telemetry modules or by encoding information in a stimulation signal generated by signal generator 114. For example, processor 110 and processor 90 may communicate with each other by encoding information in a stimulation signal that provides therapeutic benefits to patient 12. The receiving device may sense the stimulation signal and extract information that may be encoded in the sensed signal. The transmitting device may encode the information in a stimulation signal by, for example, varying one or more signal parameters, e.g., the frequency (pulse rate), wavelength (pulse width), phase, slew rate or duty cycle. The encoded information may provide information regarding the presence of charging device 46 or a charging signal being generated by charging device 46 to charge power source 122 of INS 26, such as the duration of the charging signal, a frequency of the charging signal, or other parameters of the charging signal described herein. Further details regarding communication between INS 26 and ICD 16 via encoding information in a stimulation signal may be found in commonly-assigned U.S. patent application Ser. No. 12/363,215 to Krause et al., entitled "COMMUNICATION BETWEEN IMPLANTABLE MEDICAL DEVICES," and filed on Jan. 30, 2009

The various components of INS 26 are coupled to power source 122, which may include a rechargeable battery or another type of rechargeable power source, such as a supercapacitor. In some examples, INS 26 may include a non-rechargeable power source, and ICD 16 may include a rechargeable power source that may be recharged by charging device 46. A non-rechargeable power source may be selected to last for several years, while a rechargeable power source may be inductively charged from an external device, such as charging device 46, e.g., on a daily or weekly basis.

In some examples, power source 122 may be coupled to a charging antenna 124, through which power source 122 may be charged by an external device. Charging antenna 124 may comprise a conductive coil, and may be enclosed in housing 126, or may be external to housing 126 and encapsulated in a separate material. For example, charging antenna 124 may comprise a platinum loop antenna encapsulated in a biocompatible polymer, such as silicone, polyurethane, or the like. In other examples, charging antenna 124 may comprise another conductive material, such as, for example, silver or copper, and may be enclosed in a hermetic or near hermetic housing, such as a ceramic housing. In examples in which charging antenna 124 is external to housing 126, charging antenna 124 may be coupled to power source 122 via a hermetic connector, which may comprise a metallic conductor enclosed in a hermetic encapsulant. The conductor may penetrate housing 126 through a hermetic feedthrough.

Figure 7:
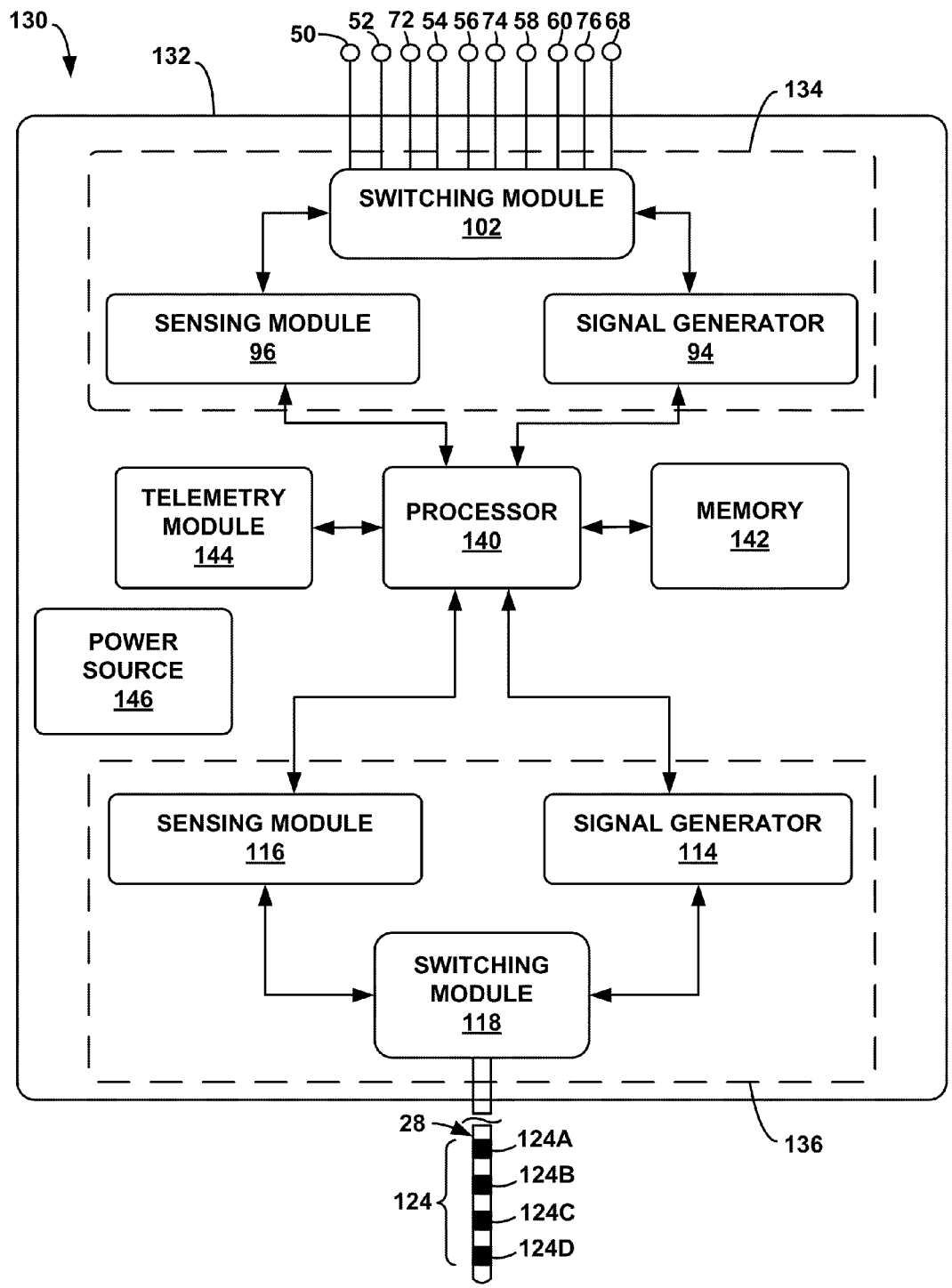
FIG. 7 is a functional block diagram of an example implantable medical device (IMD) that includes a cardiac therapy module and an electrical stimulation module.

In some examples, therapy modules performing the functions of ICD 16 and INS 26 may be contained in a single IMD. For example, as illustrated in FIG. 7, an IMD 130 may include cardiac therapy module 134 and electrical stimulation module 136 contained in a single outer medical device housing 132. Housing 132 may comprise any suitable housing that substantially encloses the components of IMD 130, and may include, for example, a hermetically sealed housing. IMD 130 also includes processor 140, memory 142, telemetry module 144, and power source 146. Memory 142 includes computer-readable instructions that, when executed by processor 140, cause IMD 130 and processor 140 to perform various functions attributed to IMD 130 and processor 140 herein. Memory 142 may include any volatile, non-volatile, magnetic, optical, or electrical media, such as a RAM, ROM, NVRAM, EEPROM, flash memory, MRAM, or any other digital media.

Processor 140 may be similar to processor 90 (FIG. 5) of ICD 16 and processor 110 (FIG. 5) of INS 26. Processor 140 may include any one or more of a microprocessor, a controller, a DSP, an ASIC, a FPGA, or equivalent discrete or integrated logic circuitry. In some examples, processor 140 may include multiple components, such as any combination of one or more microprocessors, one or more controllers, one or more DSPs, one or more ASICs, or one or more FPGAs, as well as other discrete or integrated logic circuitry. The functions attributed to processor 140 herein may be embodied as software, firmware, hardware or any combination thereof.

Sensing module 96 and signal generator 94 of cardiac therapy module 134 are described above with respect to FIG. 5. Processor 140 controls cardiac therapy module 134 to monitor cardiac signals of heart 14 and deliver cardiac rhythm management stimulation therapy to heart 14 according to a selected one or more of therapy programs, which may be stored in memory 142. Specifically, processor 140 may control signal generator 94 to deliver electrical pulses with the amplitudes, pulse widths, frequency, or electrode polarities specified by the selected one or more therapy programs. Just as with ICD 16 (FIG. 5), cardiac therapy module 134 may monitor electrical signals from heart 14 via one or more of electrodes 50, 52, 54, 56, 58, 60, 68, 72, 74, 76, and provide appropriate electrical stimulation to heart 14 via electrodes 50, 52, 54, 56, 58, 60, 68, 72, 74, 76. Signal generator 94, sensing module 96, and switching module 102 may perform as described above with respect to FIG. 5.

Processor 140 also controls electrical stimulation module 136 to monitor electrical signals indicative of one or more physiological parameters of patient 12 via sensing module 116 and provide electrical stimulation therapy to a nonmyocardial or nonvascular cardiac tissue site via signal generator 114. Specifically, processor 140 may control signal generator 114 to deliver electrical pulses or waveforms with the amplitudes, pulse widths, frequency, or electrode polarities specified by a selected one or more therapy programs. Signal generator 114 and sensing module 116 are described above with respect to FIG. 6.

Telemetry module 144 supports wireless communication under the control of processor 140 between IMD 130 and an external programmer 24 (FIG. 1), charging device 46, and/or another computing device. Processor 140 of IMD 130 may receive, as updates to programs, values for various stimulation parameters such as amplitude and electrode combination, from programmer 24 via telemetry module 144. The updates to the therapy programs may be stored within memory 142. Processor 140 may also communicate parameters, instructions, or indicators with charging device 46 via telemetry module 144.

The various components of IMD 130 are coupled to power source 146, which may include a rechargeable battery. The rechargeable battery may be inductively charged from an external device, such as charging device 46, e.g., on a daily or weekly basis.

Figure 8:
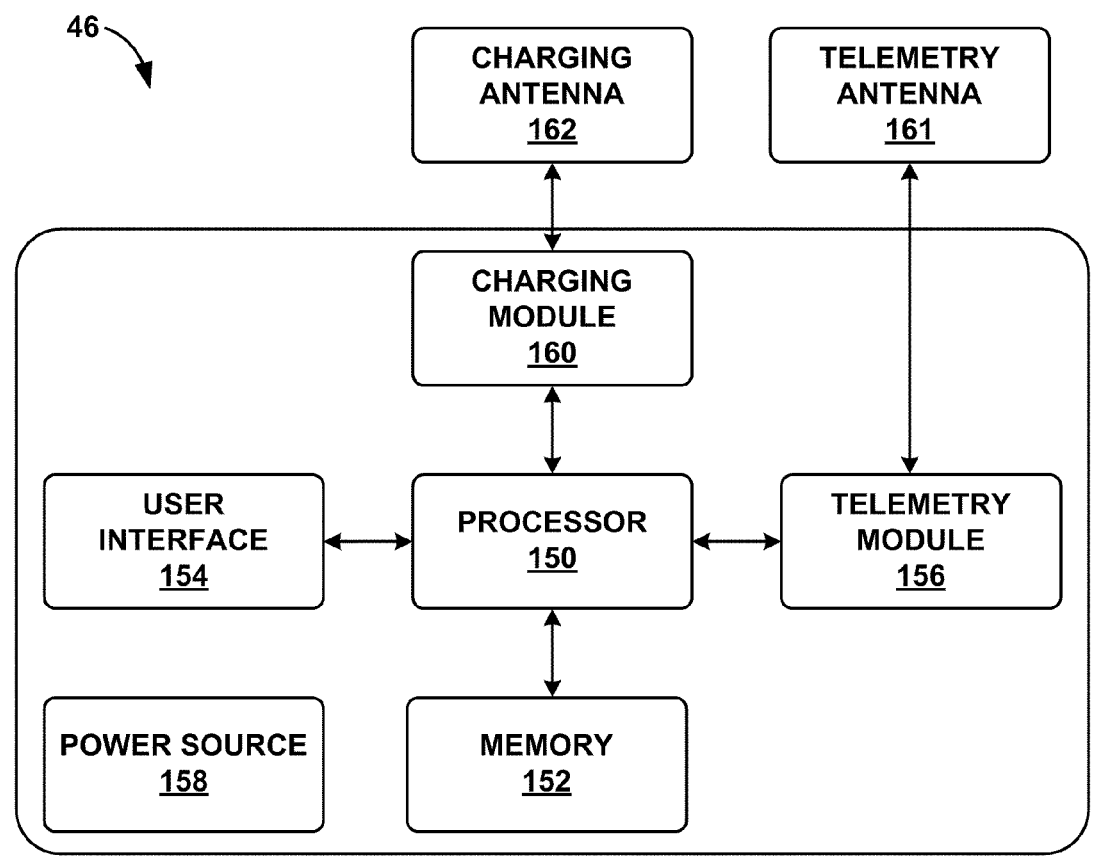
FIG. 8 is a functional block diagram of an example charging device for an IMD.

FIG. 8 is a functional block diagram of an example charging device 46. As shown in FIG. 8, charging device 46 includes processor 150, memory 152, user interface 154, telemetry module 156, power source 158, and charging module 160. Charging device 46 may be a dedicated hardware device with dedicated software for charging INS 26 or another device (e.g., ICD 16). Alternatively, charging device 46 may form a portion of another device, such as programmer 24.

A user may use charging device 46 to charge a rechargeable power source of INS 26 or another implanted medical device (e.g., ICD 16). The user may interact with charging device 46 via user interface 154, which may include a display to present a graphical user interface to the user, and a keypad, buttons, touch screen or another mechanism for receiving input from a user.

Processor 150 can take the form of one or more microprocessors, DSPs, ASICs, FPGAs, programmable logic circuitry, or the like, and the functions attributed to processor 150 herein may be embodied as hardware, firmware, software or any combination thereof. Memory 152 may store instructions that cause processor 150 to provide the functionality ascribed to charging device 46 herein, and information used by processor 150 to provide the functionality ascribed to charging device 46 herein may be stored in memory 152. Memory 152 may include any fixed or removable magnetic, optical, or electrical media, such as RAM, ROM, CD-ROM, hard or floppy magnetic disks, EEPROM, MRAM or the like. Memory 152 may also include a removable memory portion that may be used to provide memory updates or increases in memory capacities. A removable memory may also allow data to be easily transferred to another computing device, or to be removed before charging device 46 is used to charge another IMD. Memory 152 may also store information that controls operation of INS 26 or another implantable device (e.g., ICD 16) when INS 26 is being charged by charging device 46.

In some examples, memory 152 also may store parameters related to operation of ICD 16 or INS 26, which are described above in further detail. For example, memory 152 may store a sensing threshold value with which ICD 16 senses cardiac signals or a threshold value with which ICD 16 identifies cardiac parameters (e.g., R-waves or P-waves) within the sensed cardiac signal. As described above, ICD 16 may identify sensed signals that have a voltage amplitude greater than the sensing threshold value as electrical cardiac activity. As another example, memory 152 may store a blanking period duration for ICD 16 and a rate with which the blanking period occurs.

Memory 152 also may store other parameters related to operation of ICD 16 and/or INS 26. For example, memory 152 may store parameters (e.g., voltage or current amplitude or frequency) of a charging signal generated during a previous charging session in which INS 26 was charged. The previous charging session of INS 26 may be known to have not interfered substantially with the operation (e.g., sensing of electrical cardiac signals) of ICD 16. In this way, the stored signal parameters may facilitate charging of INS 26 without interfering with operation of ICD 16.

In some examples, memory 152 may also store a predetermined amplitude value for a charging signal, where the amplitude may be indicative of an amplitude that is sufficiently high to charge INS 26 but is not a maximum possible charging signal amplitude. The moderate amplitude may, in some cases, have been predetermined to be likely not to interfere with operation of ICD 16. As previously indicated, in some examples, after initiation of the delivery of a charging signal to charge INS 26, processor 150 of charging device 46 may adjust the amplitude of the charging signal from the initial, predetermined amplitude value, e.g., to increase or decrease the amplitude in response to an indication received from INS 26, ICD 16, programmer 24 or a user.

Processor 150 may control charging module 160 to generate a charging signal to charge INS 26. In some examples, charging module 160 may comprise circuitry components to generate a charging energy and an energy storage module that stores the charging energy. The energy storage may include, for example, one or more capacitors. Processor 150 may control the operation of charging module 160 to charge the energy storage module to a predetermined voltage level. Processor 150 may control charging module 160 to deliver the stored energy as a charging signal.

Charging module 160 may generate a charging signal according to a charging program, which may define parameters of the charging signal, such as, for example, amplitude, frequency, burst duration and rate, or the like. Processor 150 may control charging module 160 to generate the charging signal based on, for example, an indication that a second IMD (e.g., ICD 16) in addition to the target device to be charged is implanted in patient 12. For example, as described in further detail below, processor 90 of ICD 16 may detect presence of increased noise when charging device 46 begins charging INS 26, and may communicate an indication of the detected noise to processor 150 via telemetry modules 98 and 156. The indication of the detected noise may be a signal that indicates the presence of ICD 16. In order to mitigate interference with operation of ICD 16 (e.g., the sensing of cardiac signals), processor 150 then may modify or otherwise control the charging program that defines the signal parameters with which charging module 160 generates the charging signal.

For example, in some examples, processor 150 adjusts an amplitude of a charging signal in response to a indication received from processor 110 (FIG. 6) of INS 26. Processor 150 may control charging module 160 to initiate charging of INS 26 by generating a charging signal with an initial amplitude, which may be relatively low, intermediate, or relatively high. The initial amplitude may be predetermined and stored in memory 152. Upon receiving an indication from processor 110 of INS 26 that the amplitude of the charging signal is too low (e.g., insufficient to charge INS 26 or insufficient to efficiently charge INS 26), within an acceptable range, or larger than necessary, processor 150 of charging device 46 can control charging module 150 to take the appropriate response, e.g., increase, maintain or decrease the amplitude of the charging signal, respectively. In some examples, this process may iterate until the charging signal received by INS 26 falls within the acceptable range. Such a process may result in charging device 46 generating a charging signal that is sufficient to charge INS 26, but not excessive.

Figure 9:
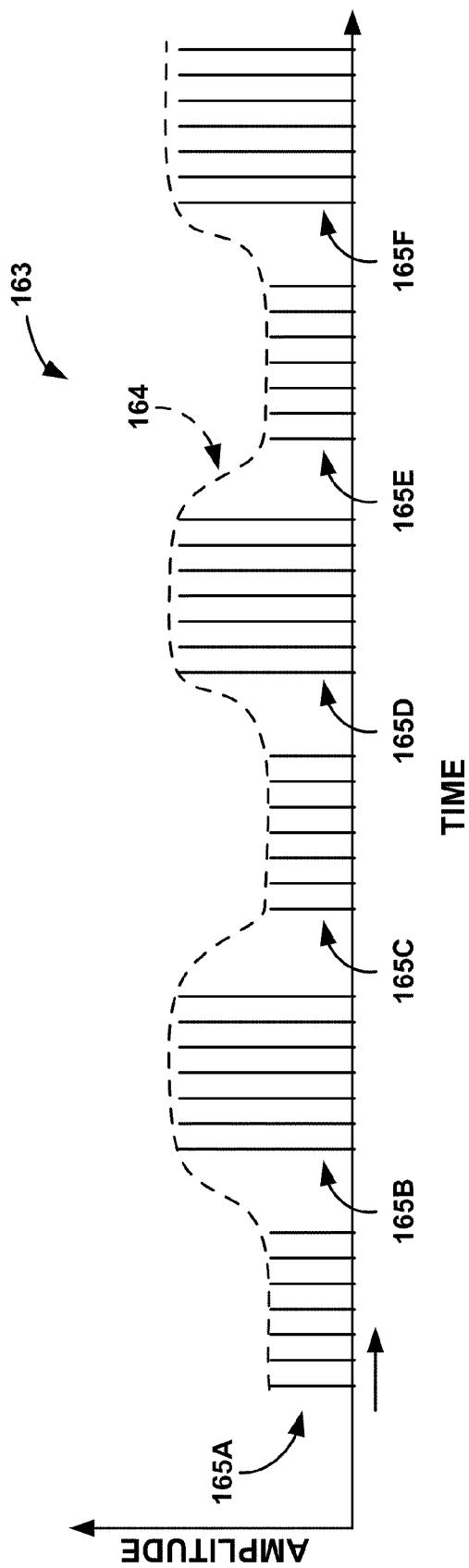
FIG. 9 illustrates an example charging signal waveform that a charging device may generate and deliver in order to reduce interference with the sensing of cardiac signals by an ICD.

As another example of a technique with which processor 150 can control the operation of charging device 46 to help reduce interference with the operation of a medical device (e.g., ICD 16) other than the target device to be charged, processor 150 may control charging module 160 to generate a charging signal with a predetermined signature, which may be characterized by a signal envelope that traces the outline of the charging signal for a given period of time. FIG. 9 illustrates an example charging signal waveform 163 that charging module 160 may generate and deliver in order to reduce interference with the sensing of cardiac signals by sensing module 96 (FIG. 5) of ICD 16. Charging module 160 may generate example charging signal waveform 163 including a plurality of charging pulses that follow a predetermined signal envelope 164. Signal envelope 164 traces the outline of example charging signal waveform 163 and is characterized by three substantially equal amplitudes and three substantially equal duration peaks.

Charging module 160 may vary one or more signal parameters, e.g., pulse rate (frequency), pulse width (rate), slew rate, current or voltage amplitude, phase, burst rate, or duty cycle, to generate the charging signal with the predetermined signature. For example, with respect to waveform 163 shown in FIG. 9, charging module 160 may generate a charging signal comprising waveform 163 by outputting bursts of pulses and alternating the amplitude of the pulses in successive bursts of pulses between two different values. With respect to FIG. 9, each pulse in burst of pulses 165A, 165C, and 165E have a first amplitude value, and each pulse in bursts of pulses 165B, 165D, and 165F have a second amplitude value that is greater than the first amplitude value. As a result, signal envelope 164 may appear similar to a square wave.

Other types of charging signals are contemplated, such as charging signals that are characterized by other shaped signal envelopes. In addition, examples in which charging module 160 generates a charging signal as a substantially continuous waveform, e.g., sinusoidal waveform, the predetermined signature may be characterized by a signal envelope that traces the outline of the charging signal for a given period of time.

In some examples, ICD 16 may be configured to process a sensed electrical signal (e.g., a cardiac signal) to substantially remove a signal artifact attributable to the charging signal produced by charging module 160 based on the known signature of the charging signal. For example, ICD 16 may include one or more filters designed to at least partially remove the signal artifact from the sensed signal. ICD 16 may analyze the processed signal, i.e., the signal with the reduced artifact, to detect cardiac events and deliver cardiac rhythm management therapy. In this way, the generation and delivery of a charging signal having a known signal signature by charging module 160 can facilitate the mitigation of any interference between charging device 46 and ICD 16.

As another example of how processor 150 may control charging module 160 to help mitigate interference of the charging signal with the operation of ICD 16, processor 150 may control charging module 160 to generate a charging signal with an amplitude that does not induce, in conductors of leads 18, 20, 22 coupled to ICD 16 (FIG. 1), a voltage having an amplitude above a threshold value. The threshold value may comprise the sensing threshold with which processor 90 (FIG. 5) of ICD 16 identifies a cardiac signal or a threshold value with which processor 90 identifies cardiac parameter in the sensed cardiac signal. For example, processor 90 may identify any signal components comprising an amplitude above the threshold value as an R-wave or a P-wave. The threshold value may be predetermined, programmed into a memory of ICD 16 or charging device 46, or may be determined dynamically based one or more factors, such as operation of ICD 16. By limiting the amplitude of the induced voltage, ICD 16 may not detect the induced voltage as a cardiac signal, or noise from the induced voltage may not significantly interfere with true cardiac signals.

In some examples, processor 150 may control charging module 160 to generate a charging signal including a maximum amplitude that increases (or "ramps up") over time near the beginning of the charging signal, decreases (or "ramps down") over time near the end of the charging signal, or both in order to help mitigate interference of the charging signal with the operation of ICD 16. In some examples, it may be that an abrupt change from no charging signal to a maximum amplitude charging signal, e.g., an abrupt turn on of the charging signal, may introduce transient voltages which affect operation of ICD 16. By gradually ramping up the charging signal to its maximum amplitude over time, the transients may not be introduced, or may comprise a lower frequency, which is filtered by a high pass filter of sensing module 96 of ICD 16.

In some examples, processor 150 controls charging module 160 to generate a charging signal with an amplitude including an initial high amplitude charging pulse followed by a series of lower amplitude charging pulses in order to help mitigate interference of the charging signal with the operation of ICD 16. The sensing threshold of ICD 16 may be automatically adjusting in some examples, and may thus automatically adjust based on the initial high amplitude charging pulse. The subsequent lower amplitude charging pulses may then induce a voltage that falls below adjusted sensing threshold, and are not sensed by processor 90 of ICD 16. In some examples, the automatically adjusting sensing threshold may automatically increase in response to the initial high amplitude charging signal and then exponentially decrease back towards the previous sensing threshold. In some examples, then, the charging signal may include an initial high amplitude charging pulse followed by a series of charging pulses that have sequentially decreasing amplitudes that decrease at a faster rate than the threshold decreases. This may result in a larger number of higher amplitude charging pulses, while still delivering charging pulses that are below the sensing threshold of ICD 16 (except the initial high amplitude charging pulse).

In other examples, processor 150 may control charging module 160 to generate a charging signal with an initial amplitude that is the same as an amplitude used in a previous charging session. The initial amplitude may be predetermined to not interfere with the operation of ICD 16. For example, memory 152 may store charging parameters, including a charging signal amplitude used in at least one previous charging session. The previous charging session may be a previous charging session of INS 26 or another device. Processor 150 may cause charging module 160 to initiate generation of the charging signal at the stored amplitude, and may or may not cause charging module 160 to adjust the charging amplitude after initiation of charging. For example, processor 150 may cause charging module 160 to adjust the amplitude of the charging signal from the initial amplitude in response to an indication received from processor 110 of INS 26, processor 90 of ICD 16, or a user. The indication from processor 110 of INS 26, processor 90 of ICD 16, or a user may indicate that the charging signal amplitude is too high or too low and interfering with the sensing of electrical cardiac signals by ICD 16, or that the charging signal amplitude is too low and resulting in inefficient charging of INS 26. Other types of indications are contemplated.

In some examples, processor 150 may control charging module 160 to generate a charging signal with an initial amplitude that is moderate, e.g., an initial amplitude that is sufficiently high to charge INS 26 but not a maximum possible amplitude that charging module 26 can generate. The moderate amplitude may, in some cases, have been predetermined to be likely not to interfere with operation of ICD 16. In some examples, processor 150 may cause charging module 160 to adjust the amplitude of the charging signal from the initial, moderate amplitude. For example, processor 150 may cause charging module 160 to adjust the amplitude of the charging signal from the initial amplitude in response to an indication received from processor 110 of INS 26, processor 90 of ICD 16, or a user.

Processor 150 also may control charging module 160 to modify an amplitude of a charging signal in response to a indication received from processor 110 of INS 26. For example, processor 150 may initiate charging of INS 26 by generating a charging signal with an initial amplitude, which may be relatively low, an intermediate, or relatively high. Processor 110 of INS 26 may monitor the amplitude of the charging signal received by a charging antenna 124 of INS 26, and may determine whether the amplitude of the received charging signal is too low, within an acceptable range, or greater than necessary. Processor 110 of INS 26 then may transmit an instruction to processor 150 to adjust the amplitude of the charging signal generated by charging module 160 such that the amplitude of the charging signal received by INS 26 falls within the acceptable range. In some examples, this process may iterate until the charging signal received by INS 26 falls within the acceptable range. Such a process may result in charging module 160 generating a charging signal that is sufficient to charge INS 26, but not excessive. In this way, processor 90 of ICD 16 or processor 150 of charging device 46 may not need to initiate additional interference mitigation techniques, or the extent of any additional interference mitigation techniques may be reduced.

Processor 150 also may control charging module 160 to generate a charging signal comprising a specific frequency value or frequency bandwidth, which may be selected to mitigate interference of the charging signal with the operation of ICD 16. The frequency value may refer to a minimum frequency of the charging signal, a maximum frequency of the charging signal, an average frequency of the charging signal, a predominant frequency of the charging signal, or another measure of the frequency or frequency band that forms the charging signal.

In some examples, processor 150 may control charging module 160 to generate a charging signal comprising a frequency value that is greater than a maximum threshold frequency that processor 90 of ICD 16 identifies as representing a cardiac signal, e.g., a maximum frequency that is sensed by sensing module 96 of ICD 16 (FIG. 5). For example, processor 150 may control charging module 160 to generate a charging signal having a frequency of about 100 Hz to about 100 MHz, although other frequency values are contemplated. Sensing module 96 or processor 90 (FIG. 5) of ICD 16 may identify an electrical signal comprising a frequency greater than or equal to the threshold as a nonphysiologic signal. In other examples, processor 90 of ICD 16 may apply a bandpass filter to sense electrical cardiac signals and electrical signals having a frequency greater than or equal to the threshold may be outside of the detection zone of ICD 16, and, therefore, ignored by ICD 16.

In other examples, processor 150 may control charging module 160 to generate a charging signal having a frequency less that a minimum frequency that sensing module 96 of ICD 16 identifies as representing a fibrillation or tachyarrhythmia, e.g., less than approximately 2.5 Hz. For example, if processor 90 of ICD 16 detects a tachyarrhythmia event if an interval of time between subsequent R-waves is less than or equal to a predetermined value, processor 150 of charging device 46 may control charging module 160 to generate and deliver a charging signal having a frequency greater than or equal to the predetermined value. This may help reduce the possibility that ICD 16 mischaracterizes the charging signal as an electrical cardiac signal indicating the presence of a tachyarrhythmia event.

In other examples, processor 150 may control charging module 160 to generate a charging signal that has a narrow band energy spectrum centered at a predetermined frequency (e.g., a narrow bandwidth charging signal) in order to help minimize interference with the operation of ICD 16. The predetermined frequency may be greater than or less than a frequency that processor 90 (FIG. 5) of ICD 16 identifies as representing tachycardia or fibrillation. In some examples, the predetermined frequency may be a frequency that does not generally interfere with identification of cardiac parameters in the cardiac signal. Accordingly, processor 90 (FIG. 5) of ICD 16 may be configured to process the detected cardiac signal to substantially remove the signal artifact from the sensed signal, for example, by applying a narrowband band stop filter centered at the predetermined frequency to the sensed cardiac signal.

Processor 150 may also control charging module 160 to generate a charging signal that has a frequency that varies within a certain frequency spectrum in order to help minimize interference with the operation of ICD 16. For example, processor 150 may control charging module 160 to generate a charging signal with a spread spectrum energy distribution or a relatively wide bandwidth (e.g., a relatively wide band energy distribution). For example, processor 150 may control charging module 160 to randomly or pseudo-randomly vary one or more signal parameters of the charging signal, e.g., a slew rate, pulse rate (frequency), pulse width (rate), phase, or duty cycle. When processor 150 generates parameters for a charging signal, processor 150 may vary the one or more parameters for each burst, i.e., on a burst-by-burst basis, or for each pulses, i.e., on a pulse-by-pulse basis. The spread spectrum energy distribution of the charging signal may cause processor 90 of ICD 16 to detect the voltage induced by the charging signal as wideband noise, rather than a cardiac signal.

In some examples, processor 90 may employ signal processing techniques known in the art to substantially remove or suppress wideband noise. Alternatively, the resulting wideband noise may be such that processor 90 may employ well know signal processing techniques for monitoring cardiac activity. In other words, processor 90 may not need to be configured to include additional processing features for removing the resulting wideband noise.

Figure 10A:
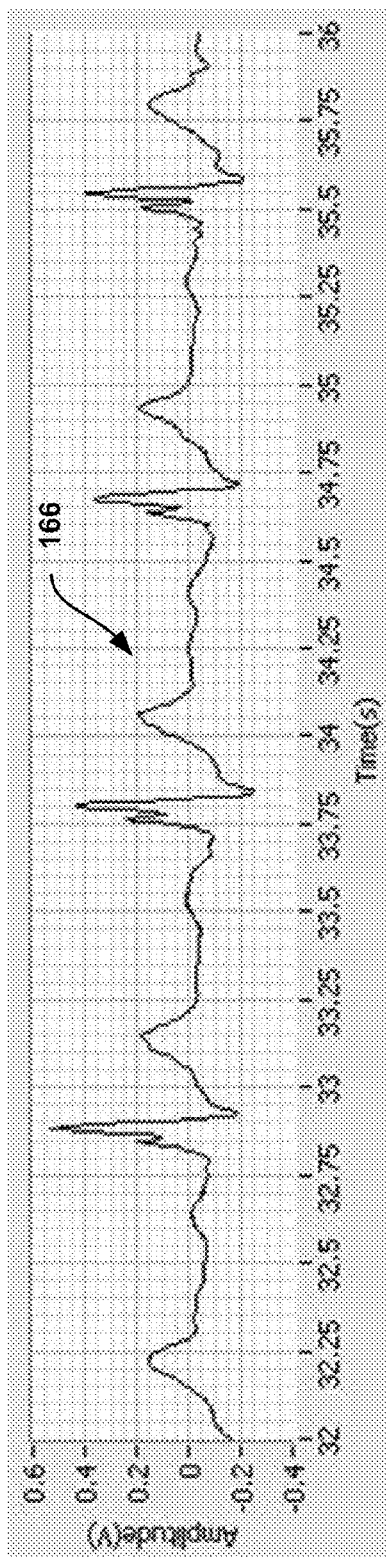
FIG. 10A illustrates an example electrogram (EGM) waveform generated by an ICD when a recharge device is not delivering charging signals to charge an INS.
Figure 10B:
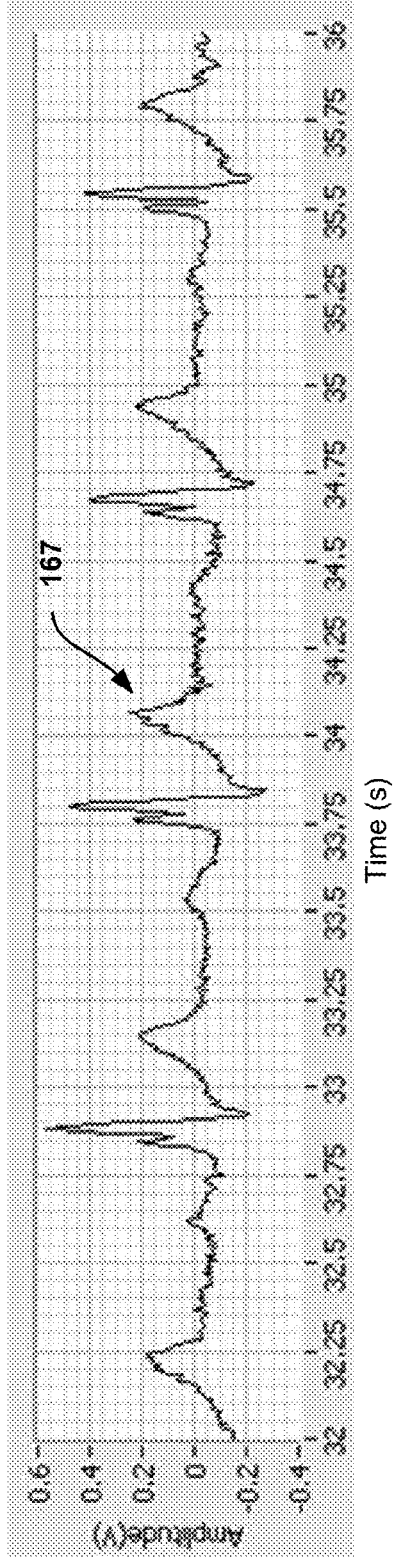
FIG. 10B illustrates an example EGM waveform generated by the ICD when a recharge device is delivering charging signals to charge an INS, where the charging signals have a wide band energy distribution.

FIGS. 10A and 10B illustrate example EGM waveforms that represent an electrical signal sensed by sensing module 96 (FIG. 5) of ICD 16. EGM waveform 166 in FIG. 10A may be generated by ICD 16 when charging module 160 of charging device 46 is not delivering a charging signal. Accordingly, EGM waveform 166 is substantially void of an artifact attributable to the delivery of charging signals to INS 26.

FIG. 10B illustrates EGM waveform 167 indicative of an electrical signal sensed by sensing module 96 of by ICD 16 while charging module 160 is delivering a charging signal to INS 26. Consequently, an artifact is present in EGM waveform 167. In the example shown in FIG. 10B, charging module 160 is generating and delivering a charging signal having one or more randomly or pseudo-randomly varied signal parameters while sensing module 96 senses an electrical signal. The signal parameters may include, for example, a current amplitude, a voltage amplitude, a pulse width, duty cycle and/or a pulse rate. In some examples, charging module 160 may not vary a frequency of the charging signal throughout the entire spectrum of frequencies (e.g., spread spectrum), but may vary the frequency within an acceptably wide range of frequencies, such as about 100 Hz to about 100 MHz. Charging module 160 also may vary an amplitude or current of the charging signal within acceptable ranges.

In FIG. 10B, the artifact from the delivery of charging signals to INS 26 by charging module 160 appears as wideband noise in EGM waveform 167 because the random or pseudo-random variation of the values of one or more signal parameters of the charging signal by charging module 160 produces a spread spectrum (e.g., wide band) energy distribution. Because the energy of the charging signal is spread substantially across the frequency spectrum or across a relatively wide band of frequencies, rather than concentrated in a relatively narrow frequency band, interference with the detection of cardiac signals or cardiac parameters of the cardiac signals by ICD 16 from the recharging of INS 26 may be mitigated. In other words, the energy of the charging signal is spread out in such a way that the crosstalk does not adversely interfere with the electrical signal sensed by ICD 16 or the ability of ICD 16 to monitor cardiac events using the EGM waveform 167 generated via the sensed electrical signal.

When charging module 160 generates a charging signal with a spread spectrum energy distribution or an energy distribution spread across a relatively wide frequency band, ICD 16 may utilize techniques well known in the art for analyzing the EGM waveform and may not require additional processing to suppress the wideband noise. Alternatively, ICD 16 may use wideband filters or filtering techniques to substantially remove or mitigate the wideband noise. In some examples, a filter may be applied to a time domain signal. In other examples, ICD 16 may convert the received analog signal to a digital signal and use digital signal processing techniques, such as performing a frequency analysis and apply digital filters to the digital signal.

In some examples, charging module 160 generates a charging signal that comprises a frequency that induces a voltage that, when aliased by an analog to digital converter (ADC) circuit that samples signals at a lower frequency than the frequency of the induced voltage, falls in a frequency range that is already substantially filtered by digital filtering performed by a processor 90 of ICD 16. That is, the processor may generate a charging signal that comprises a higher frequency than the sampling frequency of the ADC circuit. Thus, when the induced voltage sensed by processor 90 is sampled by the ADC circuit, a waveform having a different morphology, and thus a different frequency, may be formed. This resulting waveform may fall within a range that is filtered by digital filtering techniques employed by the processor 90 or by a physical filter in sensing module 96.

In some examples, processor 150 of charging device 46 may control charging module 160 to generate a charging signal comprising bursts of electrical pulses. Processor 150 may control charging module 160 to generate a charging signal comprising a plurality of bursts of pulses, where the bursts are spaced in time, such that a charging signal is not continuously delivered to power source 122 of INS 26.

Figure 11:
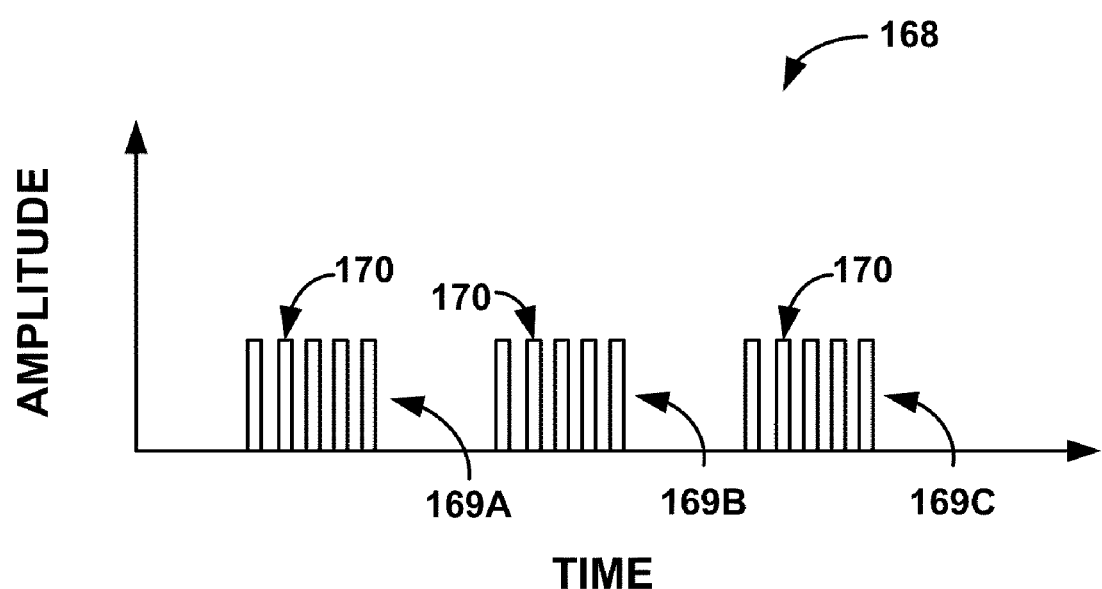
FIG. 11 illustrates an example charging signal waveform that a charging device may generate and deliver in order to reduce interference with the sensing of cardiac signals by an ICD.

FIG. 11 illustrates an example charging signal 168 that comprises a plurality of bursts 169A-169C, whereby each burst 169A-169C includes a plurality of pulses 170. In some examples, processor 150 may control charging module 160 to generate the bursts 169A-169C for an initial period of charging of INS 26, such as, for example, until processor 150 communicates with processor 110 of INS 26 (or another device, such as programmer 24) and determines that INS 26 is configured to be charged by charging device 46 or until processor 150 receives an indication from ICD 16, programmer 24, or INS 26 that charging of INS 26 may be initiated. In other examples, processor 150 may control charging module 160 to generate charging signal 168 comprising a plurality of bursts 169A-169C of pulses 170 until processor 150 determines whether another IMD, e.g., ICD 16, is implanted in patient 12, and whether the charging signal interferes with operation of ICD 16.

In some examples, processor 150 may control charging module 160 to generate and deliver bursts 169A-169C during a blanking period of sensing module 96 of ICD 16. For example, the duration of each of the bursts 169A-169C may be less than or equal to the blanking period of sensing module 96. By delivering the bursts 169A-169C of charging pulses 170 during the blanking period of sensing module 96, the possibility that sensing module 96 may sense the charging signal 168 and processor 90 may mischaracterize charging signal 169 as a cardiac signal or mischaracterize at least portions of the signal as cardiac parameters (e.g., R-waves or P-waves) may be minimized. As described above, in other examples, charging signal 168 may comprise a plurality of bursts, each of which may comprise a substantially continuous waveform, e.g., a sinusoidal waveform.

In some examples, ICD 16 may be configured to provide either single-chamber pacing and sensing or multiple-chamber pacing and sensing. When providing multiple-chamber pacing and sensing, the blanking period for at least one of the chambers may be different that the blanking period for at least a different one of the chambers. In examples such as this, processor 150 may control charging so that charging of INS 26 occurs only during at least one of the chamber's blanking period. Additionally, in some examples, the charging signal may interfere with sensing of only some of the chambers in a multiple-chamber pacing and sensing device, e.g., because of the relative positioning between the sense electrodes and charging device 46. Processor 90 of ICD 16 may then switch to a single-chamber pacing and sensing mode using a chamber with which the charging signal does not interfere while charging device 46 is delivering the charging signal.

In some examples, in order to help reduce interference with the detection of cardiac events by ICD 16, processor 150 may control charging module 160 to generate the charging signal in a plurality of bursts, where the number of consecutive bursts are less than a number of intervals to detect that define an arrhythmia episode. For example, as described above, processor 90 may identify cardiac rhythms having an R-R interval or a P-P interval less than a threshold interval as an arrhythmia event, and require a certain number of arrhythmia events to be detected in order to detect an arrhythmia episode. Thus, if charging module 160 generates a charging signal comprising a plurality of sets of bursts separated in time, where each set includes bursts includes a number of bursts that is less than the number required for processor 90 (FIG. 5) of ICD 16 to detect an arrhythmia episode that triggers therapy delivery, processor 90 may not identify the voltage induced by the charging signal as a cardiac event, even if sensing module 96 of ICD 16 detects the induced voltage. The threshold number of bursts may be any suitable number, such as greater than three, or less than three.

In some examples, in combination with processor 150 controlling charging module 160 to generate a charging signal in a plurality of bursts, processor 150 may communicate an instruction to processor 90 of ICD 16 to increase the threshold number of events above which processor 90 identifies an arrhythmia episode that triggers some response. For example, processor 90 may increase the threshold from three arrhythmia events to five arrhythmia events for a period of time. Processor 90 of ICD 16 may occasionally or periodically reduce the threshold to the original threshold (e.g., three events) to confirm that an arrhythmia episode is not occurring.

In some examples, processor 150 may control charging module 160 to generate a charging signal that includes encoded information, which may allow processor 150 to communicate with at least one of processor 90 of ICD 16 and processor 110 of INS 26. Example techniques for encoding information in an electrical signal are described in commonly-assigned U.S. patent application Ser. No. 12/363,215 to Krause et al., entitled "COMMUNICATION BETWEEN IMPLANTABLE MEDICAL DEVICES," and filed on Jan. 30, 2009, the entire content of which is incorporated herein by reference. Similar techniques may be applied by processor 150 to encode information in a charging signal.

In some examples, processor 150 may control charging module 160 to generate a single signal that comprises a power sufficient to charge power source 122 of INS 26, and which is modulated to encode information for communication with at least one of processor 110 of INS 26 and processor 90 of ICD 16. In other examples, processor 150 may control charging module 160 to generate a first signal that comprises a power sufficient to charge power source 122 of INS 26 and a second signal that includes encoded information for communication with at least one of processor 90 of ICD 16 and processor 110 of INS 26. In these examples, the second signal may comprise a lower power than the first signal. In addition, the first and second signals may comprise different frequencies or modulations (e.g., frequency or amplitude modulation), and may be transmitted substantially simultaneously or at different times.

At least one of processor 90 of ICD 16 and processor 110 of INS 26 may be configured to decode the information encoded in the charging signal. Processor 150 may control charging module 160 to encode information in the charging signal by varying the value of one or more charging signal parameters, such as frequency, amplitude, bandwidth, burst pattern, or burst duration in a known manner, such that processor 90 or processor 110 may sense the charging signals and extract information therefrom based on the known charging signal parameter values.

For example, processor 150 may control charging module 160 to encode information in the charging signal indicating to processor 90 ICD 16 that charging device 46 is initiating charging power source 122 of INS 26. In some examples, the encoded information may include one or more operating parameters of charging device 46, such as, for example, an amplitude, frequency, bandwidth, burst pattern, or burst duration of the charging signal generated by charging module 160.

In some examples, processor 150 may control charging module 160 to generate a charging signal in a plurality of bursts and may encode information in a charging signal by varying signal parameters on a burst-by-burst basis. For example, charging module 160 may generate the charging signal as a series of bursts and vary one or more signal parameters for each of the bursts. In some examples, the charging signal in a particular burst may be generated using the same charging signal parameter values. Using this technique, processor 150 may encode information in the charging signal by associating particular burst shapes with information, where a burst shape may be defined by the charging signal parameter values used to generate the charging signal. For example, different burst shapes may be associated with specific instructions for ICD 16 or INS 26 or with different alphanumeric indicators, such as letters or numbers, and a plurality of burst shapes (symbols) may be arranged to form words or other indicators that are assigned a unique meaning or, more specifically unique information relating to the operation of charging device 46, INS 26, or ICD 16.

In some examples, the alphanumeric indicator encoded in the charging signal from charging device 46 may be associated with an instruction stored in memory 92 of ICD 16 or memory 112 of INS 26. Thus, upon extracting the alphanumeric indicator from the sensed charging signal from charging device 46, ICD 16 or INS 26 may reference memory 92 or 112, respectively, to determine what information was encoded in the stimulation signal or whether the information included a particular instruction. For example, ICD 16 or INS 26 may reference memory 92 or 122, respectively, to determine a modification to an operating parameter or operating mode associated with the alphanumeric indicator. As described in further detail below, the modification may include, for example, a modification to a sensing parameter of sensing module 96, such as a filter used to sense cardiac signals, a threshold used to sense cardiac signals, or the like.

In another example, processor 150 may encode information in the charging signal by generating a charging signal having one or more burst shapes that are associated with information, such as one or more alphanumeric indicators. A particular arrangement of multiple bursts may be associated with one or more alphanumeric indicators or with a specific instruction for processor 90 of ICD 16 or processor 110 of INS 26. This may be referred to as burst pattern encoding because information is encoded using different "patterns" of burst shapes, where a burst pattern includes more than one burst.

As another example, processor 150 may encode information in the charging signal by varying one or more charging signal parameter values on a substantially continuous basis, e.g., as charging module 160 continues to generate the charging signal. This technique may provide for a more robust charging technique compared to the burst pattern encoding technique because portions of the charging signal within a single burst may be generated according to different sets of parameters, e.g., information encoded in the charging signal may change within a single burst. Additionally, this technique may allow information to be encoded in a substantially continuous charging signal, e.g., a charging signal that is not generated in discontinuous bursts.

Processor 150 may encode information in the charging signal by associating particular charging signal shapes with an alphanumeric identifier or patterns in charging signal shapes with alphanumeric identifiers, and may arrange the alphanumeric identifiers to form words or other indicators that have a unique predetermined meaning. Processor 90 of ICD 16 or processor 110 of INS 26 may decode the charging signal using the same coding scheme with which processor 150 encoded the stimulation signal. In other examples, processor 150 may encode information in the stimulation signal by associating particular charging signal shapes with respective instructions for ICD 16 or INS 26, such as an instruction relating to a modification to a sensing parameter. In this manner, processor 150 may be configured to encode information in charging signals using well known techniques in the art of telecommunication.

In other examples, processor 150 may communicate with at least one of processor 90 of ICD 16 and processor 110 of INS 26, but without encoding information in the charging signal. For example, processor 150 may communicate with at least one of processor 90 of ICD 16 and processor 110 of INS 26 by generating a charging signal without encoded information to charge power source 122 of INS 26. At least one of processor 90 of ICD 16 and processor 110 of INS 26 may modify an operating parameter or operating mode when sensing module 96 of ICD 16 or sensing module 116 of INS 26 detects the charging signal. For example, processor 90 may withhold therapy for the time when charging device 46 is charging power source 122, or may modify one or more of the operating parameters described below.

Processor 90 of ICD 16 and processor 110 of INS 26 can detect the delivery of a charging signal by charging device 46 using any suitable technique. In some examples, processor 90 or processor 110 may monitor a noise level of an electrical signal detected by the respective sensing module 96, 116 to determine charging device 46 is actively delivering a charging signal. For example, processor 90 or processor 110 may generate a baseline noise level (also referred to as a reference noise level) at a time when charging module 160 of charging device 46 is not delivering a charging signal and compare noise measurements of a sensed signal to this baseline (or reference) noise level. The baseline noise level may be stored in memory 92 (FIG. 4) of ICD 16, memory 112 of INS 26, or another device (e.g., programmer 24). A technique for determining a baseline noise level is described below. If a characteristic of an electrical signal sensed by sensing module 96 or 116 differs from a characteristic of the baseline signal by a threshold value, processor 90 or 110 may determine that charging device 46 is delivering a charging signal. The threshold value may be an amplitude value or a power level (or energy level) in one or more frequency bands. The amplitude value may be, for example, an absolute amplitude value or a root mean square amplitude value.

In some examples, processor 90 or processor 110 may determine whether the noise level of a sensed electrical exceeds a threshold level, thereby indicating the delivery of a charging signal by charging device 46, by determining a difference between one or more signal characteristics of the baseline electrical signal and the sensed electrical signal. In some examples, the signal characteristic may comprise a current or a voltage amplitude of the signal waveforms. For example, processor 90 or processor 110 may determine a first value indicative of the difference in the amplitude of the baseline electrical signal and a sensing threshold of the respective sensing module 96 or sensing module 116. The amplitude may be a mean or median amplitude (e.g., a peak-to-peak amplitude), a highest amplitude (e.g., a peak-to-peak amplitude), a root means square (RMS) amplitude, an amplitude that is equal to a certain percentage (e.g., about 95%) of the highest amplitude, and the like.

Processor 90 may also determine a second value indicative of the difference in the amplitude of the electrical signal sensed by the sensing module 96, 116 and the sensing threshold of the respective sensing module 96, 116. The amplitude may be a mean or median amplitude, a highest amplitude, a RMS amplitude, an amplitude that is equal to a certain percentage (e.g., about 95%) of the highest amplitude, and the like. Processor 90 may determine a difference between the first and second values. If the difference is greater than or equal to a stored threshold value, processor 90 or 110 may determine that charging device 46 is delivering a charging signal.

As another example, the signal characteristic may comprise a power level within a particular frequency band of an electrical signal. Processor 90 or 110 may determine a first value indicative of the difference in energy levels in the selected frequency band of the baseline electrical signal and a stored energy level, and a second value indicative of the difference in energy levels in the selected frequency band of the sensed electrical signal and the stored energy level. If the difference between the first and second values is greater than or equal to a stored threshold value, processor 90 or 110 may determine that charging device 46 is delivering a charging signal.

In some examples, processor 150 may communicate with processor 90 of ICD 16, and may receive an indication from processor 90 that noise induced by the charging signal, for example, is not detected, is below a threshold level, comprises a frequency band that is substantially filtered, or otherwise does not substantially interfere with operation of ICD. In some examples, processor 90 of ICD 16 may determine that the noise induced by the charging signal delivered by charging module 160 is excessive if a characteristic of an electrical cardiac signal sensed by the ICD 16 while a charging signal is being delivered by charging module 160 differs from a characteristic of a baseline signal by a threshold value. The threshold value may be an amplitude value or a power level (or energy level) in one or more frequency bands. The amplitude value may be, for example, an absolute amplitude value or a root mean square amplitude value.

In some examples, sensing module 96 (FIG. 5) of ICD 16 may sense an electrical signal sensed while charging device 46 is not actively delivering any charging signals. This electrical signal may represent a baseline artifact level present in the cardiac signal sensed by ICD 16. Artifacts from sources other than the charging signals delivered by charging device 46 may be present in the signal sensed by ICD 16, such as from electromagnetic interference from electronics or electrical outlets in the patient's surroundings. The baseline electrical signal may indicate these other artifacts present in the signal sensed by ICD 16.

In some examples, processor 90 of ICD 16 senses a baseline electrical signal via a selected sensing channel of sensing module 96 (FIG. 5) of ICD 16. In some examples, sensing module 96 may include a plurality of sensing channels, which may each include an amplifier. For example, sensing module 96 may include a sensing channel including an R-wave amplifier to sense R-waves within right ventricle 32 of heart 14 (FIG. 3), a sensing channel including an R-wave amplifier to sense R-waves within left ventricle 36 of heart 14 (FIG. 3), a sensing channel including a P-wave amplifier to sense P-waves within right atrium 30 of heart 14 (FIG. 3), and/or a sensing channel including a wide band amplifier in order to generate an EGM representing the electrical activity of heart 14.

After processor 90 determines the baseline electrical signal, processor 90 may transmit a signal to processor 150 of charging device 46 to cause processor 150 of charging device 46 to control charging module 160 to being delivering charging signals to recharge INS 26. After charging module 160 commences the delivery of charging signals, processor 90 of ICD 16 may control sensing module 96 to sense an electrical signal, which may be sensed via the selected sensing channel if sensing module 96 includes a plurality of sensing channels. This electrical signal that is sensed during the delivery of charging signal by charging device 46 may be referred to as a "second electrical signal" to distinguish it from the baseline electrical signal.

Processor 90 of ICD 16 or a processor of another device (e.g., programmer 24) may determine the charging signal artifact on the selected sensing channel of ICD 16 based on the baseline electrical signal and the second electrical signal that was sensed while charging device 46 was actively delivering charging signals to charge INS 26. In some examples, the charging signal artifact that is present on more than one sensing channel of sensing module 96 of ICD 16 can be determined. In addition, in some examples, processor 90 of ICD 16 may sense the charging signal artifact present in the signal sensed via one or more selected sensing channels during a quiet segment of the cardiac cycle. The quiet segment of a cardiac cycle may be when the intrinsic electrical signal of heart 14 is least active, such as during the S-T segment of a sinus rhythm of heart 14.

In some examples, processor 90 may determine whether the noise exceeds a threshold level by determining a difference between one or more signal characteristics of the baseline electrical signal and the second electrical signal. In some examples, the signal characteristic may comprise a current or a voltage amplitude of the signal waveforms. For example, processor 90 may determine a difference in the amplitude of the baseline electrical signal and a sensing threshold of sensing module 96. This value may be referred to as the "first value" for ease of description. The amplitude may be a mean or median amplitude (e.g., a peak-to-peak amplitude), a highest amplitude (e.g., a peak-to-peak amplitude), a root means square (RMS) amplitude, an amplitude that is equal to a certain percentage (e.g., about 95%) of the highest amplitude, and the like. A sensing threshold may indicate a threshold amplitude value above which processor 90 characterizes a sensed electrical signal as an electrical cardiac signal.

Processor 90 may also determine a second value indicative of the difference in the amplitude of the second electrical signal and a sensing threshold of sensing module 96. The amplitude may be a mean or median amplitude, a highest amplitude, a RMS amplitude, an amplitude that is equal to a certain percentage (e.g., about 95%) of the highest amplitude, and the like. In order to determine the charging signal artifact (e.g., noise) on the selected sensing channel, processor 90 may determine a difference between the first and second values. If the difference is greater than or equal to a stored threshold value, which may be based on the sensing threshold amplitude of ICD 16, processor 90 may determine that interference between charging device 46 and ICD 16 due to the delivery of a charging signal by charging device 46 is unacceptable. On the other hand, if the difference between the first and second values is less than the stored threshold value, processor 90 may determine that the interference between charging device 46 and ICD 16 due to the delivery of a charging signal by charging device 46 is within acceptable ranges. In this way, processor 90 may evaluate the extent of the interference between charging device 46 and ICD 16 due to the delivery of a charging signal by charging device 46. The threshold value may be, for example, selected by a clinician and stored by programmer 24, ICD 16, INS 26 or another device.

As another example, the signal characteristic may comprise a power level within a particular frequency band of an electrical signal. Processor 90 may determine the charging signal artifact (e.g., noise) by determining a first value indicative of the difference in energy levels in the selected frequency band of the baseline electrical signal and a stored energy level, and a second value indicative of the difference in energy levels in the selected frequency band of the second electrical signal and the stored energy level. The difference between the first and second values may be indicative of noise on a sensing channel of ICD 16 due to the delivery of a charging signal by charging device 46.

Upon determining that the noise induced by the charging signal is below a threshold level, processor 150 then may control charging module 160 to cease generating the charging signal in bursts and begin generating a substantially continuous charging signal. In other examples, programmer 24 may determine whether the interference between ICD 16 and charging device 46 during the recharging of INS 26 exceeds an acceptable level, e.g., using the techniques described above with respect to processor 90 of ICD 16.

When processor 150 receives an indication from processor 90 of ICD 16 that the charging signal is substantially interfering with operation of ICD 16, e.g., because the level of noise exceeds a threshold level, and ICD 16 cannot sufficiently mitigate the interference, processor 150 may, for example, cease the delivery of the charging signal and, in some examples, alert a user interacting with charging device 46. The alert may comprise, for example, a visual alert (e.g., a warning light or alphanumeric message), an auditory alert (e.g., a beep, buzz, or other sound), a somatosensory alert (e.g., vibration) or another suitable alert. In various examples, the alert may be delivered by ICD 16, INS 26, programmer 24, or charging device 46. For example, ICD 16 or INS 26 may deliver an auditory or tactile alert, such as vibration, while programmer 24 or charging device 46 may deliver a tactile, auditory, or visual alert. The alert may indicate that INS 26 was not fully charged and/or clinician intervention may be desirable because of the interference between charging device 46 and ICD 16.

In other examples, when processor 150 receives the indication that the charging signal is interfering with operation of ICD 16, processor 150 may control charging module 160 to modify one or more parameters of the charging signal in an attempt to mitigate interference with operation of ICD 16. For example, processor 150 may control charging module 160 to modify a current or voltage amplitude, a slew rate, frequency value, a pulse rate, a duty cycle, a phase, a pulse width, a pulse rate, or frequency bandwidth of the charging signal, as described above.

Processor 150 may, in some examples, communicate with at least one of processor 110 of INS 26 and processor 90 of ICD 16 to request an indication that charging of INS 26 may begin prior to causing charging module 160 to initiate the generation and delivery of the charging signal. For example, processor 150 may request an indication of whether a second IMD (e.g., ICD 16) is present in patient 12, whether INS 26 is compatible with charging device 46, whether ICD 16 is configured to utilize at least one of the interference mitigation techniques described herein, or the like. Processor 110 of INS 26 or processor 90 of ICD 16 may generate and transmit a response to processor 150, which may indicate that processor 110 may or may not initiate charging of INS 26, or which may include at least one operating parameter of INS 26 or ICD 16. Processor 150 may then interpret the indication received from the processor 110 of INS 26 or processor 90 of ICD 16 and cause charging module 160 to initiate generation of a charging signal, if appropriate, or may generate an alert to a user. The alert may indicate that charging may be initiated or that charging is not recommended, as indicated by the communication from the processor 110 of INS 26 or processor 90 of ICD 16.

In other examples, processor 90 of ICD 16, upon detecting a charging signal, may generate and transmit an indication to processor 150 that ICD 16 is implanted within patient 12. In some examples, processor 150 may generate a more conservative (e.g., lower amplitude) charging signal so as to mitigate interference operation with ICD 16. In some examples, INS 26 may store in memory 112 an indication that ICD 16 is implanted in patient 12, and upon detecting the presence of charging device 46, may generate and transmit an indication to processor 150 that ICD 16 is present.

In some examples, processor 90 of ICD 16 may detect noise or interference above a threshold level in a sensed signal, which may be due to a charging signal generated by charging module 160 under control of processor 150. The noise or interference level may be determined, e.g., using the techniques described above with respect to determining if a characteristic of an electrical cardiac signal sensed by the ICD 16 while a charging signal is being delivered by charging module 160 differs from a characteristic of a baseline signal by a threshold value. For example, to verify that the noise or interference is indeed due to the charging signal, processor 90 of ICD 16 may generate and transmit an instruction to processor 150 to cause charging module 160 to cease generation of a charging signal. Processor 90 of ICD 16 may continue to monitor the sensed signal to determine if ceasing generation of the charging signal by charging module 160 changes the sensed signal (e.g., reduces the noise or interference in the sensed signal). Thereafter, processor 90 of ICD 16 then may generate and transmit an instruction to processor 150 to initiate generation of a charging signal. Processor 90 of ICD 16 may continue to monitor the sensed signal.

When the sensed signal does not show noise or interference above a threshold level (e.g., sufficient to interfere with operation of ICD 16), processor 90 of ICD 16 may determine that the previously detected noise or interference was not due to the charging signal generated by charging module 160. Processor 90 of ICD 16 then may do nothing (e.g., allow charging device 46 to continue to generate a charging signal) or may generate and transmit an indication to processor 150 that generation of the charging signal is not interfering with operation of ICD 16. On the other hand, when the sensed signal does show noise or interference above a threshold level, processor 90 of ICD 16 may determine that the noise or interference is due to the charging signal generated by charging 160. Processor 90 of ICD 16 may then implement one or more of the mitigation techniques described herein, such as generating and transmitting an instruction to processor 150 to control charging module 160 to modify generation of the charging signal, modifying an operating parameter of ICD 16, or the like.

In some examples, in order to help minimize interference with the sensing of cardiac events by ICD 16, processor 150 may control charging module 160 to generate a charging signal only during a blanking period of ICD 16, which refers to a period of time in which ICD 16 is not detecting a cardiac signal, or is not responsive to detected cardiac parameters (e.g., R-waves, P-waves, R-R intervals or P-P intervals) in the cardiac signal. For example, as described above, processor 150 may control charging module 160 to generate a stimulation signal in a plurality of bursts, whereby each burst may include one or more charging pulses. In some examples, charging module 160 may generate the bursts to correspond with the blanking periods such that recharge energy is only delivered during periods of time in which ICD 16 is not detecting a cardiac signal or is not responsive to detected cardiac parameters.

In some examples, parameters regarding the blanking period of ICD 16 may be stored in memory of charging device 46. The parameters may include, for example, the duration of the blanking period, the frequency with which the blanking period is implemented, and the like. Charging device 46 and ICD 16 may synchronize clocks, synchronize to paced events, synchronize to P-waves, R-waves, or both, or use other techniques for coordinating the delivering of charging bursts by charging module 160 with the blanking periods. In other examples, processor 150 may communicate with processor 90 of ICD 16 to retrieve parameters of the blanking period, and may control charging module 160 to generate a charging signal with a corresponding burst pattern.

As shown in FIG. 8, charging module 160 may be coupled to a charging antenna 162, which may comprise, for example, a loop or coiled antenna. In some examples, charging antenna 162 may comprise an internal antenna housed within a housing of charging module 46, while in other examples, charging antenna 162 may comprise an external antenna coupled to charging device 26. In either case, charging antenna 162 may be configured to be placed proximate to a charging antenna 124 of INS 26 (FIG. 6).

Charging device 46 may communicate wirelessly with one or both of ICD 16 and INS 26 separate from information encoded in a charging signal, such as using RF communication or proximal inductive interaction. This wireless communication is possible through the use of telemetry module 156, which may be coupled to an internal antenna or an external antenna, such as telemetry antenna 161. An external antenna that is coupled to charging device 46 may correspond to the programming head that may be placed over ICD 16 or INS 24, as described above with reference to FIG. 1, or may comprise charging antenna 162. In some examples, the same physical antenna may be used as telemetry antenna 161 and charging antenna 162. Telemetry module 156 may be similar to telemetry module 98 (FIG. 5) of ICD 16 or telemetry module 120 (FIG. 6) of INS 26. In some examples, telemetry antenna 161 and charging antenna 162 may be provided by a common antenna. However, as shown in FIG. 8, separate antennas are also contemplated.

Telemetry module 156 may also be configured to communicate with another computing device via wireless communication techniques, or direct communication through a wired connection. Examples of local wireless communication techniques that may be employed to facilitate communication between charging device 46 and another computing device include RF communication according to the 802.11 or Bluetooth specification sets, infrared communication, e.g., according to the IrDA standard, or other standard or proprietary telemetry protocols. In this manner, other external devices may be capable of communicating with charging device 46 without needing to establish a secure wireless connection.

Power source 158 delivers operating power to the components of charging device 46. Power source 158 may include a battery and a power generation circuit to produce the operating power and the power for providing to charging module 160. In some examples, the battery may be rechargeable to allow extended operation. Recharging of power source 158 may be accomplished by electrically coupling power source 158 to a cradle or plug that is connected to an alternating current (AC) outlet. In addition or alternatively, recharging may be accomplished through proximal inductive interaction between an external charger and an inductive charging coil within charging device 46. In other embodiments, traditional batteries (e.g., nickel cadmium or lithium ion batteries) may be used. In addition, charging device 46 may be directly coupled to an alternating current outlet to power charging device 46. Power source 158 may include circuitry to monitor power remaining within a battery. In this manner, user interface 154 may provide a current battery level indicator or low battery level indicator when the battery needs to be replaced or recharged. In some cases, power source 158 may be capable of estimating the remaining time of operation using the current battery.

Figure 12:
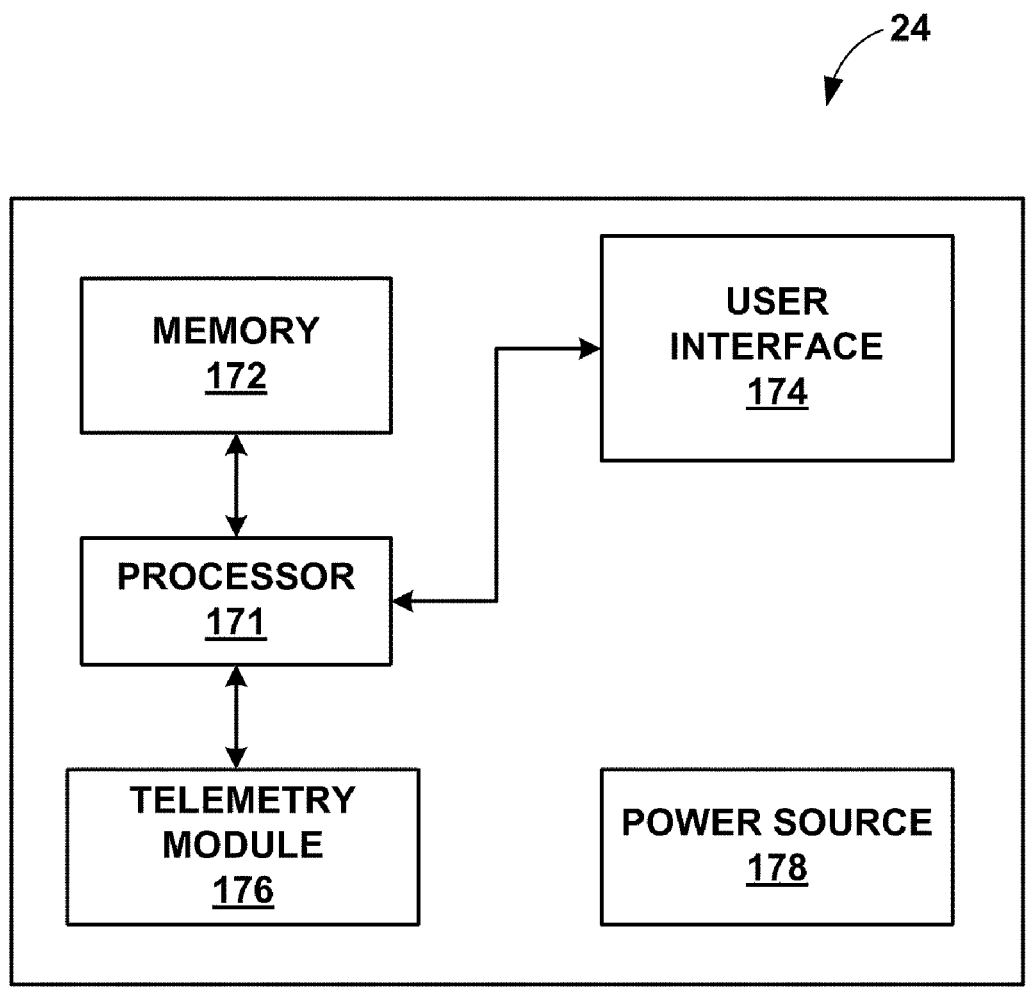
FIG. 12 is a functional block diagram of an example medical device programmer.

FIG. 12 is a functional block diagram of an example programmer 24. As shown in FIG. 12, programmer 24 includes processor 171, memory 172, user interface 174, telemetry module 176, and power source 178. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The user may interact with programmer 24 via user interface 174, which may include display to present graphical user interface to a user, and a keypad or another mechanism for receiving input from a user.

In some examples, a user may utilize programmer 24 to retrieve and view or analyze signals sensed by at least one of ICD 16 and INS 26. The signals sensed by the at least one of ICD 16 and INS 26 may show differences when charging device 46 is generating a charging signal and when charging device 46 is not generating a charging signal. The user may compare the sensed signal from exemplary time periods to observe the effects of the charging signal on signals sensed by the at least one of ICD 16 and INS 26.

Processor 171 can take the form one or more microprocessors, DSPs, ASICs, FPGAs, programmable logic circuitry, or the like, and the functions attributed to processor 171 herein may be embodied as hardware, firmware, software or any combination thereof. Memory 172 may store instructions that cause processor 171 to provide the functionality ascribed to programmer 24 herein, and information used by processor 171 to provide the functionality ascribed to programmer 24 herein. Memory 172 may include any fixed or removable magnetic, optical, or electrical media, such as RAM, ROM, CD-ROM, hard or floppy magnetic disks, EEPROM, or the like. Memory 172 may also include a removable memory portion that may be used to provide memory updates or increases in memory capacities. A removable memory may also allow patient data to be easily transferred to another computing device, or to be removed before programmer 24 is used to program therapy for another patient. Memory 172 may also store information that controls therapy delivery by ICD 16 and INS 26, such as stimulation parameter values.

Programmer 24 may communicate wirelessly with ICD 16 and INS 26, such as using RF communication or proximal inductive interaction. This wireless communication is possible through the use of telemetry module 176, which may be coupled to an internal antenna or an external antenna. An external antenna that is coupled to programmer 24 may correspond to the programming head that may be placed over ICD 16 or INS 24, as described above with reference to FIG. 1. Telemetry module 176 may be similar to telemetry module 98 of ICD 16 (FIG. 5) or telemetry module 120 of INS 26 (FIG. 6).

Telemetry module 176 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 178 delivers operating power to the components of programmer 24. Power source 178 may include a battery and a power generation circuit to produce the operating power. In some examples, the battery may be rechargeable to allow extended operation. Recharging may be accomplished by electrically coupling power source 178 to a cradle or plug that is connected to an AC outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 178 may include circuitry to monitor power remaining within a battery. In this manner, user interface 174 may provide a current battery level indicator or low battery level indicator when the battery needs to be replaced or recharged. In some cases, power source 178 may be capable of estimating the remaining time of operation using the current battery.

Figure 13:
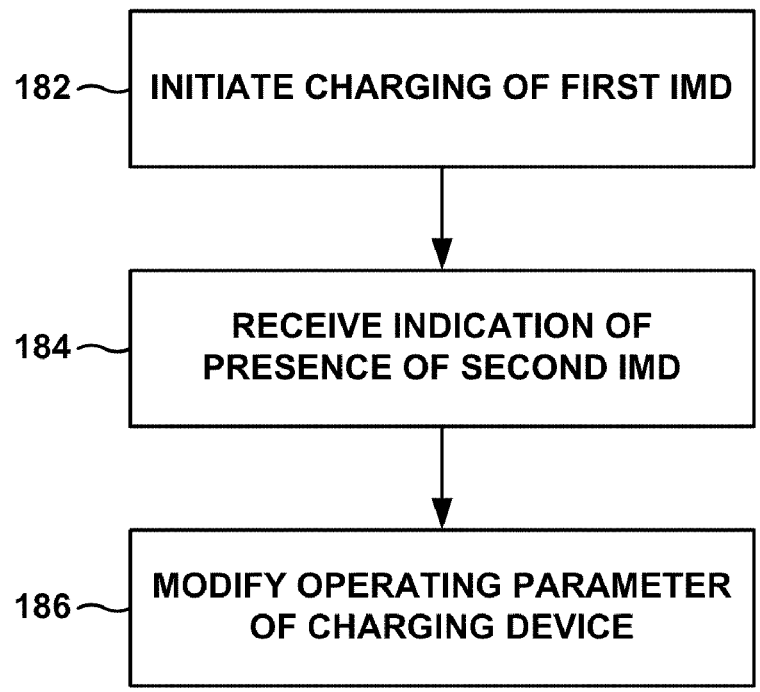
FIG. 13 is a flow diagram of an example technique a charging device may implement to charge an IMD.

FIG. 13 is a flow diagram illustrating an example technique with which charging device 46 may charge an IMD that is implanted in patient 12. Processor 150 (FIG. 8) of charging device 46 may initiate charging of a first IMD implanted in patient 12 (182). As described above, in some examples the first IMD may comprise an INS 26. In other examples, the first IMD may comprise an ICD 16, an implantable monitoring device, an implantable drug delivery device, or another implantable device that provides therapy to patient 12 or monitors a physiological parameter of patient 12. For ease of description, the first IMD will be referred to as INS 26 throughout the description of FIG. 13.

Processor 150 may initiate charging of INS 26 in response to an input from a user, such as patient 12, a technician, or a clinician. For example, the user may input one or more commands via user interface 154 (FIG. 8) of charging device 46. The command may comprise, for example, an instruction to begin charging, which can be as simple as powering-up charging device 46 or may be more specific, such as selecting a specific function of charging device 46. The user commands may include further instructions, such as instructions regarding parameters of the charging signal generated by charging module 160. The parameters may include, for example, amplitude, frequency value, frequency bandwidth, burst duration, burst rate, or the like. As another example, processor 150 may automatically initiate (e.g., without user intervention) charging of INS 26 in response to detecting the presence of INS 26. In some examples, processor 150 may receive an indication of the presence of INS 26 via telemetry module 156 (FIG. 8) of charging device 46.

Processor 150 may control charging module 160 (FIG. 8) of charging device 46 to begin generating and delivering a charging signal to charge INS 26 upon receiving the instruction to initiate charging from the user, or upon automatically receiving the indication of the presence of INS 26 via telemetry module 156. In some examples, processor 150 may control charging module 160 to generate the charging signal as a plurality of charging bursts separated by periods in which charging module 160 does not generate a charging signal. In other examples, processor 150 may control charging module 160 to generate a substantially continuous charging signal. Processor 150 may continue to instruct charging module 160 to generate the charging signal in this manner until processor 150 receives an indication from INS 26 that INS 26 is configured to be charged by charging device 46. This may help charging device 46 identify INS 26, which allows processor 150 verify that charging device 46 is configured to charge INS 26.

Processor 150 may receive an indication of the presence of a second IMD, which will be referred to hereafter ICD 16, implanted in patient 12 (184), where the second IMD is not the target device to be charged by charging device 46. For example, processor 90 of ICD 16 may detect presence of charging device 46, generate the indication, and communicate the indication to processor 150 via the respective telemetry modules 98 (FIG. 5) and 156 (FIG. 8). In some examples, processor 90 may detect the operation of charging device 46 by detecting, via sensing module 96 (FIG. 5), an increased noise level due to an induced voltage in the conductors of one or more of leads 18, 20, 22.

In other examples, processor 90 may detect the presence of charging device 46 through communication between processor 90 and processor 150 via the respective telemetry modules 98 and 156. For example, processor 150 of charging device 46 may transmit a general identification signal to ICD 16 via telemetry module 156, e.g., prior to delivering a first charging signal to INS 26. Processor 90 may detect the identification signal via telemetry module 98, where the signal may be associated with an indication that charging device 46 is near the vicinity of ICD 16, e.g., within a certain radius (e.g., one meter to five meters). Processor 90 of ICD 16 may also identify the presence of charging device 46 based on a signal received from INS 26.

Regardless of the manner in which processor 90 of ICD 16 detects the presence and/or operation of charging device 46, processor 90 may generate the indication of the presence of ICD 16 and communicate the indication of the presence of ICD 16 to processor 150 of charging device 46. In some examples, processor 90 may generate the indication of the presence of ICD 16 and communicate the indication of the presence of ICD 16 to processor 110 of INS 26, which may be an intermediary telemetry link between ICD 16 and charging device 46. Processor 110 of INS 26 then may communicate the indication of the presence of ICD 16 to processor 150 of charging module device 46. In some examples, programmer 24 or another external computing device may provide the intermediary telemetry link between ICD 16 and charging device 46 in addition to or instead of INS 26.

In response to receiving the indication of the presence of ICD 16, processor 150 of charging device 46 modifies an operating parameter of charging device 46 (186). For example, processor 150 may modify an operating parameter of charging device 46 based on one or more operating parameters (e.g., sensing parameters) of ICD 16 that are stored in memory 152. Sensing parameters of ICD 16 that may be stored include, for example, a threshold amplitude above which processor 90 of ICD 16 identifies a feature of a detected cardiac signal as being a cardiac parameter, such as an R-wave or P-wave or a sensing threshold with which processor 90 identifies electrical cardiac signals. Other sensing parameters of ICD 16 include the number of intervals to detect an arrhythmia episode or a total duration of an arrhythmia episode processor 90 of ICD 16 is programmed to identify.

The sensing parameters of ICD 16 may also include an interval range of identified cardiac parameters (e.g., R-waves) that processor 90 interprets as representing a cardiac rhythm. For example, processor 90 may identify a first range of frequencies of a cardiac parameter, e.g., R-waves, which represent a normal or acceptable cardiac rhythm. This first range of frequency values may be defined by R-R or P-P intervals of a normal sinus rhythm of patient 12. Processor 90 may also identify a second range of frequencies of the cardiac parameter, which is greater than the first range of frequencies, as a cardiac rhythm representing tachycardia. The second range of frequency values may be defined by R-R or P-P intervals that define tachycardia events. Processor 90 may also identify a third range of frequencies of the cardiac parameter, which is greater than both the first range and the second range of frequencies, as a cardiac rhythm representing fibrillation. The third range of frequency values may be defined by R-R or P-P intervals that define fibrillation events. In some examples, processor 90 may identify frequencies below the first range and above the third range as not representing a cardiac rhythm.

In some examples, the sensing parameters of ICD 16 stored in memory 152 of charging device 46 may also include a blanking period duration or blanking rate of sensing module 96. The blanking period refers to a period of time after delivery of stimulation when sensing module 96 is not sensing cardiac signals, or the period in which processor 90 or signal generator 94 is not responsive to detected cardiac signals. Thus, when ICD 16 is delivering, for example, pacing pulses to heart 14, the blanking period may occur at a consistent rate and may last a consistent length of time.

The sensing parameters of ICD 16 stored in memory 152 of charging device 46 may also include a frequency or range of frequencies that are attenuated or substantially removed by a filter applied by ICD 16 (e.g., by processor 90). For example, processor 90 may include a bandstop filter that attenuates a range of frequencies, essentially at least partially removing these frequencies from the detected signal. In some examples, the bandstop filter may be non-adjustable, while in other examples the bandstop filter may be adjustable. When the bandstop filter is adjustable, the bandstop filter may be controlled by processor 90 of ICD 16 to attenuate a certain range of frequencies. As other examples, processor 90 of ICD 16 may include a high pass filter and/or a low pass filter, which may attenuate a low frequency signal and a high frequency signal, respectively. Processor 90 may also comprise circuitry or logic that attenuates or removes a signature signal or an artifact of a signature signal from a sensed electrical signal. Memory 152 of charging device 46 may also store information relating to the filters applied by processor 90 of ICD 16.

In some examples, processor 150 may modify an operating parameter of charging module 160 (186) based on the operating parameters of ICD 16 stored in memory 152. The operating parameter of charging module 160 may include, for example, a parameter of the charging signal generated by charging module 160. For example, processor 150 may control charging module 160 to generate a charging signal with a predetermined signature, which ICD 16 (e.g., based on an applied filter or cardiac signal sensing threshold) may be configured to or controlled to attenuate or substantially remove a signal artifact attributable to the signature charging signal produced by charging module 160. In further examples, processor 150 may control charging module 160 to generate a charging signal with an amplitude that does not induce, in conductors of leads 18, 20, 22 coupled to ICD 16 (FIG. 1), a voltage that has an amplitude above a threshold value stored in memory 152.

Processor 150 also may control charging module 160 to generate a charging signal comprising a specific frequency value or frequency bandwidth. As previously described, in some examples, processor 150 controls charging module 160 to generate a charging signal comprising a frequency value that is greater than a maximum frequency that processor 90 of ICD 16 identifies as representing a cardiac signal, e.g., a maximum frequency that is sensed by sensing module 96 of ICD 16 (FIG. 5). In other examples, processor 150 controls charging module 160 to generate a charging signal having a frequency less that a minimum frequency that sensing module 96 of ICD 16 identifies as representing a fibrillation or tachyarrhythmia, e.g., less than approximately 2.5 Hz. In addition, in other examples, processor 150 controls charging module 160 to generate a charging signal having a frequency that is attenuated by a filter in processor 90 or is outside of a frequency band which sensing module 96 a identifies a cardiac signal or a frequency less than the frequency of R-waves or P-waves that processor 90 identifies as an arrhythmia episode.

In other examples, processor 150 may control charging module 160 to generate a charging signal comprising a spread spectrum energy distribution or wide band energy distribution that results in no one frequency having an amplitude which induces a voltage in conductors within leads 18, 20, 22 above the threshold value stored in memory 152. In some examples, processor 150 may control charging module 160 to generate a charging signal in a plurality of bursts that correspond to blanking periods of ICD 16. In some examples, processor 150 may control charging module 160 to generate a charging signal including two or more of the above features, such as frequency and amplitude, or amplitude and frequency bandwidth.

In other examples, memory 152 of charging device 46 may not store operating parameters of ICD 16. In some examples, processor 150 may modify an operating parameter of charging device 46 by selecting a particular charging program stored in memory 152. A charging program may define values for one or more parameters of the charging signal, such as, for example, an amplitude, frequency value, frequency bandwidth, burst duration, or burst rate of the charging signal. Processor 150 may select the charging program based on, for example, the indication of the presence of ICD 16. For example, the indication of the presence of ICD 16 may include an identifier of the type or model of ICD 16 that is implanted in patient 12. The charging programs may define charging signal parameters selected in order to mitigate or eliminate interference between a charging signal generated by charging module and operation of the identified ICD 16.

In still other examples, processor 150 of charging device 46 may receive values for one or more signal parameters from processor 90 of ICD 16 and may modify an operating parameter of charging device 46 based on these parameters. For example, processor 90 may communicate one or more of the ICD operating parameters (e.g., sensing parameters) described above as being stored in memory 152 of charging device 46 to charging device 46 using wireless communication. The operating parameters of ICD 16 may include, for instance, a signature signal or signal artifact that processor 90 is configured to attenuate or remove, a threshold amplitude above which processor 90 identifies a cardiac parameter of a cardiac signal, one or more frequencies or frequency ranges that may be attenuated by a filter in processor 90 or sensing module 96, one or more frequency range that sensing module 96 identifies as representing a cardiac rhythm, or the like. Processor 150 then may modify an operating parameter of charging device 46, e.g., by controlling charging module 160 to generate a charging signal that mitigates interference with operation of ICD 16, such as, by conforming to the parameter communicated by processor 90 of ICD 16.

In some examples, after modifying an operating parameter, processor 150 of charging device 46 delivers test charging signals to INS 26, e.g., for a predetermined duration of time. Processor 90 of ICD 16 may determine whether the noise from the delivery of the test charging signals exceeds a threshold level using the techniques described above with respect to FIG. 8. If processor 90 of ICD 16 determines that the crosstalk exceeds an acceptable level, processor 90 may transmit a signal to charging device 46 that causes processor 150 to further adjust one or more operating parameters, which may or may not be the same operating parameters previously modified (186). The charging operating parameter modification may continue until processor 90 of ICD 16 no longer indicates that the crosstalk exceeds an acceptable level.

In some examples, processor 90 of ICD 16 modifies an operating parameter of charging device 46 in response to receiving an indication of a presence or operation of charging device 46. In addition, in some examples, processor 90 modifies an operating parameter of ICD 16 in response to receiving an indication of a presence or operation of charging device 46.

Figure 14:
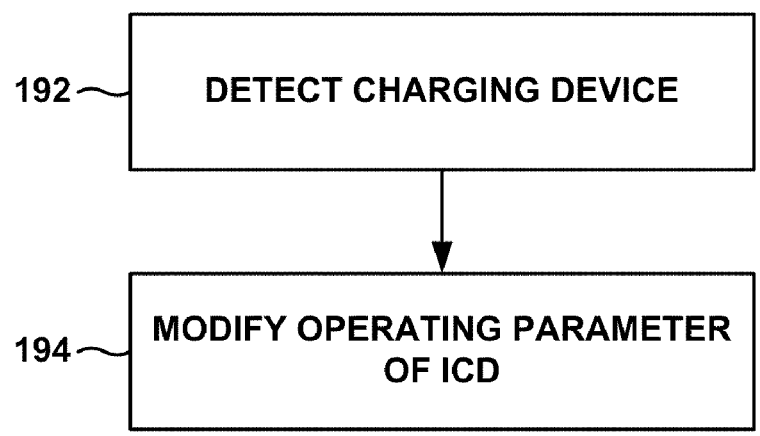
FIG. 14 is a flow diagram of another example technique a charging device may implement to charge an IMD.

FIG. 14 is a flow diagram illustrating an example technique with which processor 90 of ICD 16 may modify an operating parameter of ICD 16, which may be, for example, a sensing parameter with which sensing module 96 (FIG. 5) senses electrical cardiac signals. Processor 90 may detect the presence or operation of charging device 46 (192). As described above, in some examples, processor 90 detects the presence and operation of charging device 46 by detecting via, sensing module 96 (FIG. 5), an increased noise level due to an induced voltage in conductors of one or more of leads 18, 20, 22. In other examples, processor 90 may detect the presence of charging device 46 based on a signal received from charging device 46. For example, processor 150 (FIG. 8) of charging device 46 may transmit a general identification signal to ICD 16 via telemetry module 156 (FIG. 8) of charging device 46. In some examples, charging device 46 may transmit the identification signal prior to the delivery of any charging signals to INS 26. Processor 90 may receive the identification signal via telemetry module 98 (FIG. 5) and interpret the signal as indicating the presence of charging device 46, e.g., within a particular radius (e.g., one meter to about five meters).

Regardless of the manner in which processor 90 detects the presence or operation of charging device 46, processor 90 may modify an operating parameter of ICD 16 based on the detection of the presence of charging device 46 or the delivery of a charging signal by charging device 46 (194). For example, processor 90 may modify one or more sensing parameters of sensing module 96 or stimulation parameters of stimulation module 94. As indicated above, in some examples, in addition to initiating the modification to a sensing parameter or another ICD parameter, processor 90 may initiate the modification to a charging parameter of charging device 46. For example, processor 90 of ICD 16 may communicate an instruction to processor 150 of charging device 46 to modify the charging parameters of charging device 46.

In some examples, processor 90 of ICD 16 modifies an operating parameter of ICD 16 by at least modifying the values of one or more sensing parameters with sensing module 96 senses cardiac signals or with which processor 90 identifies cardiac signals or cardiac parameters of the cardiac signals. For example, processor 90 may increase a sensing threshold with which processor 90 identifies cardiac signals in order to decrease the influence of electrical noise on sensing cardiac signals, where the noise may be caused by an induced voltage from the charging signal delivered by charging device 46. In some examples, processor 90 may periodically reduce the threshold amplitude to confirm that the increased threshold is not resulting in under-sensing of cardiac signals or cardiac events. Processor 90 may also increase a threshold amplitude with which processor 90 identifies a cardiac parameter of the sensed signal, such as, for example, an R-wave or a P-wave.

As another example of how processor 90 may modify a sensing parameter of ICD 16, processor 90 may attenuate, substantially remove, or ignore an artifact in a signal sensed by sensing module 96 based on a known signature of a charging signal generated by charging module 160 of charging device. The signature or signature artifact of the charging signal may be characterized by a signal envelope that traces the outline of the charging signal for a given period of time. In some examples, processor 90 may apply one or more filters that are configured to filter out the charging signal generated and delivered by charging device 46.

In some examples, sensing module 96 may comprise two or more channels or electrode vectors (e.g., defined by two or more electrodes 50, 52, 54, 56, 58, 60, 68, 72, 74, 76, shown in FIG. 4) with which electrical signals may be sensed. One or more of the sensing channels may include electrical components that process a sensed signal to attenuate or substantially remove the signature or signature artifact of the charging signal. For example, the signal path may include resistors, inductors, or capacitors arranged to form a filter, such as a high pass filter, low pass filter, band pass filter, band stop filter, or a combination of two or more of these filters. Processor 90 may apply different filters by controlling the channel with which sensing module 96 senses electrical signals. In other examples, processor 90 may mathematically manipulate a digital representation of the detected electrical cardiac signal (e.g., digital signal processing) to attenuate or remove the signature or signature artifact of the charging signal. In still other examples, processor 90 or sensing module 96 may apply any technique known in the art to attenuate or remove the signature or signature artifact of the charging signal. For example, processor or sensing module 96 may apply a rate stability criterion, a wavelet criterion, or a P-R stability criterion to mitigate the effect of the artifact of the charging signal on detection of the cardiac signal.

In other examples, processor 90 may modify an operating parameter of ICD 16 by modifying a duration of a blanking period of sensing module 96. As described above, the blanking period refers to the period of time after signal generator 94 delivers stimulation to heart 14 or after a sensed cardiac signal during which sensing module 96 does not actively sense electrical signals, or during which signal generator 94 is not responsive to detected cardiac events. Processor 90 may increase the duration of the blanking period to increase the length of time during which charging module 160 may generate a charging signal that may not be detected by sensing module 96. In some examples, processor 90 may periodically decrease the blanking period duration to confirm that patient 12 is not experiencing an arrhythmia, such as tachycardia or fibrillation.

In some examples, processor 90 may be configured to provide either single-chamber pacing and sensing or multiple-chamber pacing and sensing. When providing multiple-chamber pacing and sensing, the blanking period for at least one of the chambers may be different that the blanking period for at least a different one of the chambers. In some examples, processor 90 may independently adjust a blanking period for each of the chambers.

In some examples, processor 90 may temporarily switch ICD 16 from a multiple-chamber pacing and sensing mode to a single-chamber pacing and sensing mode when processor 90 determines that the charging signal is interfering with sensing of electrical cardiac signals (e.g., an EGM) within some, but not all, chambers of heart 14. The processor of ICD 16 may then return ICD 16 to a multiple-chamber pacing and sensing mode periodically to determine whether the charging signal is still interfering with sensing within other chambers of heart 14. Once processor 90 determines that the charging signal is no longer interfering with sensing within the other chambers, processor 90 may return stimulation generator 94 and sensing module 96 to a multiple-chamber pacing and sensing mode.

As previously described, in some examples, processor 90 modifies a sensing parameter by increasing the number of intervals to detect, with which the processor of ICD 16 identifies an arrhythmia episode that triggers some response (e.g., delivery of a defibrillation shock). For example, the processor of ICD 16 may increase the number of intervals to detect from three arrhythmia events to five arrhythmia events for a period of time. The processor of ICD 16 may occasionally or periodically reduce the threshold to the original threshold (e.g., three events) to confirm that an arrhythmia episode is not occurring.

In addition to or instead of increasing the number of intervals to detect an arrhythmia episode, processor 90 of ICD 16 may adjust an arrhythmia event detection algorithm with which the processor detects an arrhythmia event or episode. For example, processor 90 may periodically modify the arrhythmia event detection interval thresholds for determining the R-R or P-P interval that indicates an arrhythmia event. For example, processor 90 may increase the threshold (e.g., from 300 ms to 500 ms) while charging device 46 is delivering charging signals to INS 26, to reduce the possibility that processor 90 mischaracterizes the charging signals as an electrical cardiac signal that indicates the presence of an arrhythmia event. After temporarily increasing the event detection intervals, processor 90 may increase the event detection interval (e.g., while charging device 46 suspends the delivery of charging signals), in order to confirm that processor 90 is not missing the detection of any tachyarrhythmia events.

In addition, processor 90 may also increase the number of intervals to detect, with which the processor of ICD 16 identifies an arrhythmia episode that triggers some response (e.g., delivery of a defibrillation shock). For example, the processor of ICD 16 may increase the number of intervals to detect from three arrhythmia events to five arrhythmia events for a period of time. The processor of ICD 16 may occasionally or periodically reduce the threshold to the original threshold (e.g., three events) to confirm that an arrhythmia episode is not occurring.

In some examples, processor 90 may enable a rate stability criterion. A rate stability criterion requires R-R intervals to be relatively consistent (e.g., stable) before interpreting the R-R interval as an arrhythmia. This may help avoid detecting irregularly conducted atrial fibrillation. In many examples, noise appears as an irregular signal in a sensed cardiac signal, so a rate stability criterion may mitigate the effect of noise on detection of heart arrhythmias.

In some examples, processor 90 may utilize a wavelet criterion to mitigate the effect of noise on detection of heart arrhythmias. A wavelet criterion requires the morphology of a cardiac signal detected by EGM to change before interpreting cardiac signal parameters as representing a true arrhythmia. Because noise may appear as an irregular signal in the sensed cardiac signal, implementation of a wavelet criterion to detect an arrhythmia may also be used mitigate the effect of noise on detection of a true heart arrhythmia. For example, as described with respect to FIG. 5, processor 90 apply a wavelet template to a sensed cardiac signal when charging device 46 is delivering a charging signal to INS 26 to determine a wavelet score indicative of a similarity between the wavelet template and the sensed cardiac signal when charging device 46 is delivering a charging signal to INS 26. For example, processor 90 may cross-correlate the wavelet template and the sensed cardiac signal to determine the wavelet score indicative of similarity between the template and the sensed cardiac signal. When the wavelet score indicates that the wavelet template and the sensed cardiac signal are not sufficiently similar (e.g., the wavelet score based on cross-correlation between the wavelet template and the sensed cardiac signal is less than a threshold value), processor 90 may determine that the generation of the charging signal by charging device 46 is interfering with operation of ICD 16, and may cause processor 150 of charging device 46 to cease charging of INS 26, modify at least one charging parameter, or the like.

In other examples, as described in further detail with respect to FIG. 5, processor 90 may implement a P-R logic criterion while charging device 46 charges INS 26 to attempt to mitigate the effect of noise on detection of heart arrhythmias. For example, if a P-R logic criterion implemented by processor 90 returns a result that indicates a tachycardia or fibrillation event may be occurring, processor 90 may compare a P-R logic result determined when charging device 46 was not charging INS 26 to a P-R logic result determined when charging device 46 was actively delivering charging signals to INS 26. When the first P-R logic result is different than the second P-R logic result, processor 90 may generate and transmit an instruction to a processor 150 of charging device 46 (FIG. 8) that causes the charging device 46 to cease charging of INS 26, modify at least one charging parameter used to generate the charging signal, or the like.

As another example, as described with respect to FIG. 5, processor 90 may apply a P-R logic criterion that is designed to distinguish noise induced by charging of INS 26 by charging device 46 from true a ventricular tachycardia rhythm or a true ventricular fibrillation rhythm. For example, processor 90 may utilize at least one of an AV interval pattern, a VA interval pattern, an expected range of a ventricular-ventricular interval, an expected range of an AV interval, atrial fibrillation evidence, evidence of potential far-field R-wave sensing, atrial-ventricular dissociation, or ventricular-ventricular regularity to determine whether a sensed cardiac signal includes events that are caused by noise rather than true atrial or ventricular events.

In still other examples, processor 90 modifies an operating parameter of ICD 16 by controlling sensing module 96 to interrupt or suspend operation of sensing module 96 for a period of time. For example, processor 90 may control sensing module 96 to suspend operation for a period of time that spans a plurality of cardiac cycles, during which charging module 160 may deliver a charging signal to charge INS 26. Processor 90 then may restart operation of sensing module 96 to monitor cardiac signals.

As previously indicated, in some examples, processor 90 may monitor a noise level of a cardiac signal detected by sensing module 96 to determine whether a charging signal generated by charging module 160 (FIG. 8) of charging device 46 is interfering with operation of sensing module 96 (FIG. 5) of ICD 16. For example, processor 90 may generate a reference noise level at a time when charging module 160 is not generating a charging signal and compare noise measurements collected when charging module 160 is generating a charging signal to this reference noise level. The reference noise level may be stored in memory 92 (FIG. 4) or another device (e.g., programmer 24). In some example, when processor 90 determines that the noise level is interfering with operation of sensing module 96, processor 90 may generate an interference indication and communicate the interference indication to processor 150 (FIG. 8) of charging device 46 via the respective telemetry modules 98 (FIG. 5) and 156 (FIG. 8). In some examples, processor 150 of charging device 46 may suspend the delivery of the charging signal upon receiving the interference indication from ICD 16. In other examples, processor 150 may control charging module 160 to modify one or more parameters of the charging signal in an attempt to mitigate interference with operation of sensing module 96, as described above with respect to FIG. 13.

Figure 15:
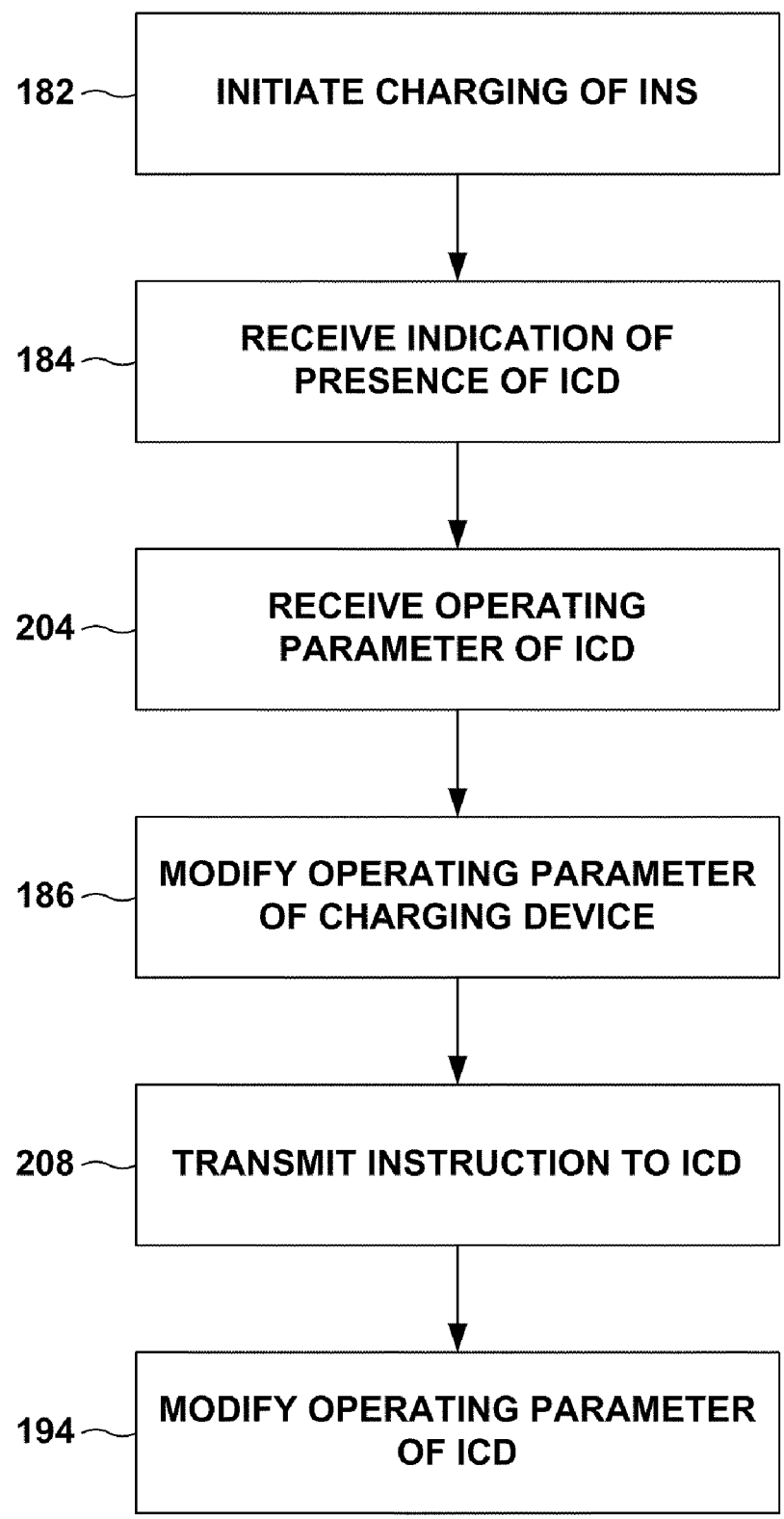
FIG. 15 is a flow diagram of another example technique a charging device may implement to charge an IMD.

In other examples, such as the technique illustrated in FIG. 15, both the operating parameters of charging device 46 and ICD 16 may be modified while charging device 46 is delivering a charging signal to charge power source 122 (FIG. 6) of INS 26 in order to mitigate interference with sensing of cardiac signals by ICD 16. In the technique shown in FIG. 15, processor 150 of charging device 46 may initiate charging of INS 26 (182), as described with respect to FIG. 13. For example, processor 150 may initiate charging of INS 26 in response to an instruction from a user, such as patient 12, a technician, or a clinician, in response to detecting the presence of INS 26 or in response to being powered-up (e.g., turned on) or other activation of the charging features of charging device 46.

Processor 150 of charging device 46 may receive an indication of the presence of ICD 16 (184), as described with respect to FIG. 13. While FIG. 15 illustrates this step as occurring after processor 150 initiates charging of INS 26, in other examples, processor 150 may receive the indication of the presence of ICD 16 prior to initiating charging of INS 26. In addition to receiving an indication of the presence of ICD 16, processor 150 of charging device 46 may receive a signal indicating an operating parameter of ICD 16 from processor 90 of ICD 16 (204). For example, as described above in further detail, the operating parameter may comprise a sensing threshold value with which processor 90 identifies a cardiac signal, a threshold value with which processor 90 identifies a cardiac parameter from a detected cardiac signal, a duration of a blanking period, and a rate of the blanking period, a frequency or frequency bandwidth that a filter of ICD 16 is configured to attenuate or substantially remove from an electrical signal sensed by sensing module 96, R-R or P-P intervals with which processor 90 detects a cardiac arrhythmia, and the like.

In response to receiving the operating parameter, processor 150 of charging device 46 may modify an operating parameter of charging device 46, e.g., charging module 160 (186), as described above with respect to FIG. 13. For example, processor 150 may control charging module 160 to generate a charging signal comprising a signature waveform or a charging signal comprising a predetermined amplitude. In other examples, processor 150 may control charging module 160 to generate a charging signal comprising a specific frequency value or frequency bandwidth, or a charging signal comprising bursts corresponding to the blanking period duration and rate.

Processor 150 may communicate an instruction to processor 90 of ICD 16 via the respective telemetry modules 156 (FIG. 8) and 98 (FIG. 5) (208). Processor 90 then may modify an operating parameter of ICD 16 in response to the instruction (194). In some examples, processor 90 may modify the operating parameter of ICD 16 in a manner compatible with or complementary to the manner in which processor 150 modifies an operating parameter of charging device 46.

For example, processor 150 may control charging module 160 to generate a charging signal comprising a narrow band energy spectrum centered around a certain frequency. Processor 90 then may control an adjustable bandstop filter to attenuate or substantially remove the noise induced by the charging signal. Other examples of complementary modification to operating parameters of charging device 46 and ICD 16 are also contemplated. For example, processor 150 may control charging module 160 to generate a charging signal comprising a signature waveform, and processor 90 may apply a filter based on the known charging signal signature to remove a signal artifact due to the signature charging signal.

While the preceding description has been described primarily with reference to a therapy system including an ICD 16, INS 26, programmer 24, and charging device 46, the techniques described herein may be applicable to other therapy systems, or other systems including two or more IMDs, an IMD including two or more therapy or patient monitoring modules, or systems including multiple IMDs, one of which includes two or more modules. For example, the techniques described herein may be applicable to systems including an implantable monitoring device or an IMD including a monitoring module. As another example, the techniques described herein may be applicable to systems including an implantable drug delivery device or an IMD including a drug delivery module. Other combinations of implantable device will be obvious to one of skill in the art, and fall within the scope of this disclosure.

The techniques described in this disclosure, including those attributed to ICD 16, charging device 46, programmer 24, INS 26, or other devices, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following example claims.

The invention claimed is:

1. A system comprising:
 a first therapy module configured to be implanted within a patient;
 a second therapy module configured to be implanted within the patient;
 a charging device configured to charge the first therapy module; and
 a processor configured to receive an indication of a presence of the second therapy module and modify, based on the indication, an operating parameter of the charging device to reduce interference with operation of the second therapy module, wherein the operating parameter comprises a parameter with which the charging device generates or delivers a charging signal to the first therapy module.

2. The system of claim 1, wherein the charging device comprises the processor.

3. The system of claim 1, further comprising a medical device programmer that comprises the processor.

4. The system of claim 1, wherein one of the first or second therapy modules comprises the processor.

5. The system of claim 1, further comprising a first implantable medical device (IMD) comprising a first outer housing enclosing the first therapy module and a second IMD comprising a second outer housing enclosing the second therapy module, wherein the first and second outer housings are physically separate from each other and separately implantable within the patient.

6. The system of claim 1, further comprising an implantable medical device comprising an outer housing, wherein the outer housing encloses the first therapy module and the second therapy module.

7. The system of claim 1, wherein the first therapy module comprises an electrical stimulation module configured to deliver electrical stimulation to at least one of a tissue site proximate a nerve, a nonmyocardial tissue site, or a nonvascular cardiac tissue site, and the second therapy module comprises a cardiac therapy module that is configured to deliver at least one of pacing, cardioversion or defibrillation therapy to a heart of the patient.

8. The system of claim 1, wherein the second therapy module comprises an electrical stimulation module configured to deliver electrical stimulation to at least one of a tissue site proximate a nerve, a nonmyocardial tissue site, or a nonvascular cardiac tissue site, and the first therapy module comprises a cardiac therapy module that is configured to deliver at least one of pacing, cardioversion or defibrillation therapy to a heart of the patient.

9. The system of claim 1, wherein the indication comprises a first indication, wherein the processor is configured to modify the operating parameter of the charging device by at least controlling the charging device to cease charging the first therapy module in response to a second indication that the charging is interfering with operation of the second therapy module.

10. The system of claim 9, wherein the second therapy module is configured to determine whether the charging of the first therapy module by the charging device is interfering with operation of the second therapy module and generate the second indication.

11. The system of claim 9, wherein the second therapy module is configured to determine whether the charging of the first therapy module by the charging device is interfering with operation of the second therapy module by at least:
sensing a first electrical signal while the charging device is not delivering a charging signal to the first therapy module;
comparing a first signal characteristic of the first electrical signal to a threshold to determine a first value;
sensing a second electrical signal while the charging device is delivering the charging signal to the first therapy module;
comparing a second signal characteristic of the second electrical signal to a threshold to determine a second value; and
determining a difference between the first value and the second value.

12. The system of claim 1, wherein the second therapy module is configured to deliver therapy to the patient, and wherein the processor is configured to further modify the operating parameter of the charging device to prompt the second therapy module to adjust therapy delivery while the charging device charges the first therapy module.

13. The system of claim 1, wherein the second therapy module is configured to detect electrical cardiac activity of the patient, and wherein the processor further is configured to further modify the operating parameter of the charging device to prompt the second therapy module to adjust a detection threshold for detecting the electrical cardiac activity of the patient while the charging device charges the first therapy module.

14. The system of claim 1, wherein the processor is configured to modify the operating parameter of the charging device by at least controlling the charging device to generate and deliver a charging signal comprising a plurality of bursts of pulses to charge the first therapy module.

15. The system of claim 14, wherein the plurality of bursts comprises a first set of bursts and a second set of bursts separated by a predetermined duration of time that is greater than or equal to an arrhythmia event detection interval with which the second therapy module detects an arrhythmia event of the patient.

16. The system of claim 1, wherein the processor is configured to modify the operating parameter of the charging device by at least controlling the charging device to generate a charging signal that comprises a frequency greater than a threshold frequency.

17. The system of claim 16, wherein the threshold frequency corresponds to an arrhythmia event detection interval with which the second therapy module detects an arrhythmia event.

18. The system of claim 16, wherein the frequency is about 100 hertz to about 100 megahertz.

19. The system of claim 1, wherein the processor is configured to modify the operating parameter of the charging device by at least controlling the charging device to generate a charging signal that comprises a frequency less than a threshold frequency.

20. The system of claim 19, wherein the threshold frequency comprises a frequency band with which the second therapy module characterizes a sensed signal as a nonphysiologic signal.

21. The system of claim 1, wherein the second therapy module comprises a filter that is configured to attenuate a frequency or remove the frequency from a sensed signal, and wherein the processor is configured to modify the operating parameter of the charging device to generate a charging signal that comprises the frequency.

22. The system of claim 1, wherein the processor is configured to modify the operating parameter of the charging device to deliver a charging signal to the first therapy module during a blanking period of the second therapy module.

23. The system of claim 1, wherein the processor is configured to modify the operating parameter of the charging device to generate a charging signal that comprises a spread spectrum energy or wide band energy distribution.

24. The system of claim 1, further comprising a lead electrically connected to the second therapy module, the lead comprising an electrical conductor electrically connected to an electrode, wherein the second therapy module is configured to sense an electrical signal via the electrode and identify the electrical signal as a cardiac signal if a first amplitude of the electrical signal is greater than or equal to a sensing threshold, and wherein the processor is configured to modify the operating parameter of the charging device to generate a charging signal that induces, in the electrical conductor, a voltage comprising a second amplitude less than the first amplitude.

25. The system of claim 1, further comprising a lead electrically connected to the second therapy module, the lead comprising an electrical conductor electrically connected to an electrode, wherein the second therapy module is configured to sense a cardiac signal via the electrode, and wherein the processor is configured to modify the operating parameter of the charging device to generate a charging signal that induces, in the electrical conductor, a voltage that does not affect processing of the cardiac signal by the second therapy module.

26. The system of claim 1, further comprising a lead electrically connected to the second therapy module, the lead comprising an electrical conductor electrically connected to an electrode, wherein the second therapy module is configured to sense a cardiac signal via the electrode, and wherein the processor is configured to modify the operating parameter of the charging device to generate a charging signal that induces, in the electrical conductor, a voltage that does not cause the cardiac signal to be sufficiently dissimilar to a wavelet template to indicate charging of the first therapy module by the charging device interferes with operation of the second therapy module.

27. The system of claim 1, further comprising a lead electrically connected to the second therapy module, the lead comprising an electrical conductor electrically connected to an electrode, wherein the second therapy module is configured to sense a cardiac signal via the electrode, and wherein the processor is configured to modify the operating parameter of the charging device to generate a charging signal that induces, in the electrical conductor, a voltage that does not produce a P-R logic result of the cardiac signal that indicates charging of the first therapy module by the charging device interferes with operation of the second therapy module.

28. The system of claim 1, wherein the processor is configured to modify the operating parameter of the charging device by at least controlling the charging device to deliver a first charging signal comprising a first amplitude followed by a plurality of charging signals each comprising amplitudes less than the first amplitude.

29. A method comprising:
receiving an indication of a presence of a first therapy module implanted in a patient; and
modifying, by a processor and based on the indication, an operating parameter of a charging device that charges a second therapy module implanted in the patient, wherein the operating parameter comprises a parameter with which the charging device generates or delivers a charging signal to the second therapy module.

30. The method of claim 29, wherein the first therapy module is enclosed in a first outer housing and the second therapy module is enclosed in a second outer housing, wherein the first and second outer housings are physically separate from each other and separately implantable within the patient.

31. The method of claim 29, wherein the first therapy module comprises an electrical stimulation module configured to deliver electrical stimulation to at least one of a tissue site proximate a nerve, a nonmyocardial tissue site, or a nonvascular cardiac tissue site, and the second therapy module comprises a cardiac therapy module that is configured to deliver at least one of pacing, cardioversion or defibrillation therapy to a heart of the patient.

32. The method of claim 29, wherein the indication comprises a first indication, the method further comprising receiving a second indication that indicates a delivery of a charging signal to the second therapy module is interfering with operation of the first therapy module, wherein modifying the operating parameter of the charging device comprises controlling the charging device to cease the delivery of the charging signal to the second therapy module based on the first and second indications.

33. The method of claim 29, wherein the first therapy module is configured to deliver therapy to the patient, the method further comprising prompting the first therapy module to adjust therapy delivery while the charging device charges the second therapy module.

34. The method of claim 29, wherein modifying the operating parameter of the charging device based on the indication comprises controlling the charging device to generate and deliver a charging signal comprising a plurality of bursts of pulses to charge the second therapy module.

35. The method of claim 34, wherein the plurality of bursts comprises a first set of bursts and a second set of bursts separated by a predetermined duration of time that is greater than or equal to an arrhythmia event detection interval with which the first therapy module detects an arrhythmia event of the patient.

36. The method of claim 29, wherein modifying the operating parameter of the charging device based on the indication comprises controlling the charging device to generate a charging signal that comprises a frequency greater than a threshold frequency.

37. The method of claim 36, wherein controlling the charging device to generate a charging signal that comprises a frequency greater than a threshold frequency comprises controlling the charging device to generate a charging signal that comprises a frequency of about 100 hertz to about 100 megahertz.

38. The method of claim 29, wherein modifying the operating parameter of the charging device based on the indication comprises controlling the charging device to generate a charging signal that comprises a frequency lower than a threshold frequency.

39. The method of claim 29, wherein the first therapy module comprises a filter that attenuates a frequency or removes the frequency from a sensed signal, and wherein modifying the operating parameter of the charging device comprises controlling the charging device to generate a charging signal that comprises the frequency.

40. The method of claim 29, wherein modifying the operating parameter of the charging device based on the indication comprises controlling the charging device to deliver a charging signal to the second therapy module during a blanking period of the first therapy module.

41. The method of claim 29, wherein modifying the operating parameter of the charging device based on the indication comprises controlling the charging device to generate a charging signal comprising a spread spectrum energy or wide band energy distribution.

42. The method of claim 29, wherein the first therapy module is electrically connected to a lead comprising an electrical conductor electrically connected to an electrode, and the second therapy module is configured to sense an electrical signal via the electrode and identify the electrical signal as a cardiac signal if a first amplitude of the electrical signal is greater than or equal to a sensing threshold, and wherein modifying the operating parameter of the charging device based on the indication comprises controlling the charging device to generate a charging signal that induces, in the electrical conductor, a voltage comprising a second amplitude that is less than the first amplitude.

43. The method of claim 29, wherein the first therapy module is electrically connected to a lead comprising an electrical conductor electrically connected to an electrode, and the second therapy module is configured to sense a cardiac signal via the electrode, and wherein modifying the operating parameter of the charging device based on the indication comprises controlling the charging device to generate a charging signal that induces, in the electrical conductor, a voltage that does affect processing of the cardiac signal by the second therapy module.

44. The method of claim 29, wherein the modifying the operating parameter of the charging device based on the indication comprises controlling the charging device to deliver a first charging signal comprising a first amplitude followed by a plurality of charging signals each comprising amplitudes less than the first amplitude.

45. A system comprising:
a charging module configured to generate a charging signal to charge a first therapy module implanted in a patient; and
a processor configured to receive an indication of a presence of a second therapy module in the patient and modify an operating parameter of the charging module to reduce interference with operation of the second therapy module based on the indication, wherein the operating parameter comprises a parameter with which the charging device generates or delivers a charging signal to the first therapy module.

46. The system of claim 45, wherein the processor is configured to modify the operating parameter of the charging module by at least modifying at least one of a duty cycle, a pulse width, a slew rate, a phase, a frequency bandwidth, a frequency value, a burst duration, a burst rate, a current amplitude, or a voltage amplitude of the charging signal delivered to the first therapy module.

47. A system comprising:
means for charging a first therapy module implanted within a patient;
means for receiving an indication of a presence of a second therapy module implanted in the patient; and
means for modifying, based on the indication, an operating parameter of the means for charging to reduce interference with operation of the therapy module, wherein the operating parameter comprises a parameter with which the charging device generates or delivers a charging signal to the first therapy module.

48. The system of claim 47, wherein the means for charging generates a charging signal and the means for modifying the operating parameter is configured to modify at least one of a duty cycle, a slew rate, a phase, a frequency bandwidth, a frequency value, a burst duration, a burst rate, a current amplitude, or a voltage amplitude of the charging signal.

49. A computer readable medium comprising instructions that cause a programmable processor to:
receive an indication of a presence of a first therapy module implanted in a patient; and
based on the indication, modify an operating parameter of a charging device that charges a second therapy module implanted in the patient, wherein the operating parameter comprises a parameter with which the charging device generates or delivers a charging signal to the first therapy module.

50. The computer readable medium of claim 49, wherein the instructions comprise instructions that cause the programmable processor to modify at least one of a pulse width, a duty cycle, a slew rate, a phase, a frequency bandwidth, a frequency value, a burst duration, a burst rate, a current amplitude, or a voltage amplitude of the charging signal with which the charging device charges the second therapy module.

* * * * *